(12) United States Patent
Schwartz Mittelman et al.

(10) Patent No.: US 9,109,223 B2
(45) Date of Patent: Aug. 18, 2015

(54) METHODS FOR GENERATING AND SCREENING FUSION PROTEIN LIBRARIES AND USES THEREOF

(75) Inventors: Adrian Schwartz Mittelman, Winnipeg (CA); Jeannick Cizeau, Winnipeg (CA); Nicholas Ronald Glover, Oakville (CA); Glen Christopher MacDonald, Winnipeg (CA)

(73) Assignee: Viventia Bio, Inc. (CA)

( * ) Notice: Subject to any disclaimer, the term of this patent is extended or adjusted under 35 U.S.C. 154(b) by 1637 days.

(21) Appl. No.: 12/097,419

(22) PCT Filed: Dec. 22, 2006

(86) PCT No.: PCT/CA2006/002113
§ 371 (c)(1),
(2), (4) Date: Nov. 10, 2008

(87) PCT Pub. No.: WO2007/071061
PCT Pub. Date: Jun. 28, 2007

(65) Prior Publication Data
US 2009/0075878 A1    Mar. 19, 2009

Related U.S. Application Data

(60) Provisional application No. 60/752,871, filed on Dec. 23, 2005.

(51) Int. Cl.
*C40B 30/04* (2006.01)
*C12N 15/10* (2006.01)
(Continued)

(52) U.S. Cl.
CPC ............ *C12N 15/1034* (2013.01); *C07K 16/30* (2013.01); *C12N 15/1086* (2013.01); *C12P 21/02* (2013.01); *C40B 30/04* (2013.01); *G01N 33/5014* (2013.01); *C07K 2316/95* (2013.01); *C07K 2317/21* (2013.01); *C07K 2317/55* (2013.01); *C07K 2317/56* (2013.01);
(Continued)

(58) Field of Classification Search
None
See application file for complete search history.

(56) References Cited

U.S. PATENT DOCUMENTS

| | | | |
|---|---|---|---|
| 6,406,863 B1 * | 6/2002 | Zhu et al. | 435/7.1 |
| 2003/0044772 A1 * | 3/2003 | Watkins et al. | 435/5 |

(Continued)

FOREIGN PATENT DOCUMENTS

| | | |
|---|---|---|
| WO | WO 99/06834 A2 | 2/1999 |
| WO | WO 01/88110 A1 | 11/2001 |

(Continued)

OTHER PUBLICATIONS

Ho et al. (In vitro antibody evolution targeting germline hot spots to increase activity of an anti-CD22 immunotoxin, 2005, vol. 280, pp. 607-617, published on-line Oct. 18, 2004).*

(Continued)

*Primary Examiner* — Christian Boesen
(74) *Attorney, Agent, or Firm* — Cooley LLP

(57) ABSTRACT

The invention provides methods for generating fusion protein libraries, such as immunotoxin libraries. The invention also relates to libraries of recombinant cells encoding nucleic acid sequences comprising fusion proteins. In addition, the invention relates to the libraries themselves and the use of the libraries to screen for fusion proteins that are specific for target cells, such as cancer cells. Further, the invention relates to methods of improving fusion proteins and to the improved fusion proteins.

11 Claims, 11 Drawing Sheets

(51) Int. Cl.
 C07K 16/30 (2006.01)
 C12P 21/02 (2006.01)
 G01N 33/50 (2006.01)
(52) U.S. Cl.
 CPC ....... C07K2317/565 (2013.01); C07K 2317/92 (2013.01); C07K 2319/00 (2013.01); C07K 2319/55 (2013.01)

(56) References Cited

U.S. PATENT DOCUMENTS

2003/0064435 A1* 4/2003 Weiner et al. ................ 435/69.1
2005/0238642 A1* 10/2005 Baker et al. ................. 424/141.1
2005/0260213 A1 11/2005 Koenig et al.

FOREIGN PATENT DOCUMENTS

| WO | 02/00729 | A2 | 1/2002 |
| WO | WO 2004/096271 | * | 11/2004 |
| WO | WO 2004/096271 | A1 | 11/2004 |
| WO | 2005/063817 | A2 | 7/2005 |
| WO | WO 2005/062977 | * | 7/2005 |
| WO | WO 2005/062977 | A2 | 7/2005 |
| WO | WO 2005/090579 | A1 | 9/2005 |
| WO | 2005/092917 | A1 | 10/2005 |
| WO | 2005/121341 | A1 | 12/2005 |

OTHER PUBLICATIONS

Webster's (accessed from http://machaut.uchicago.edu/?action=search&resource=Webster%27s&word=Plurality&quicksearch=on on Nov. 10, 2011, 1 page).*
Wikipedia (accessed from http://en.wikipedia.org/wiki/Claim_(patent) on Nov. 10, 2011, 7 pages).*
Clackson, T. et al. "Making antibody fragments using phage display libraries". Nature, 1991, vol. 352, No. 6336, p. 624-628.
McHeyzer-Williams, M., "B-cell signalling mechanism and activation" In: Fundamental immunol, 5th ed. Paul, WE (ed), Lippincott Williams & Wilkins, Baltimore, 2003, p. 195-225.
Yang, W.P. et al. "CDR walking mutagenesis for the affinity maturation of a potent human anti-HIV-1 antibody into the picomolar range" J Mol Biol 1995 vol. 254, No. 3, p. 392-403.
Salvatore, G., et al., "Clinical Cancer Research: Improved cytoxic activity toward cell lines and fresh leukemia cells of a mutant anti-CD22 immunotoxin obtained by antibody phage display". Clin Cancer Res 2002; 8:995-1002.0Published online Apr. 1, 2002.
Messmann, R., et al. "A Phase I Study of Combination Therapy With Immunotoxins IGG-HD37-Deglycosylated Ricin a Chain (DGA) and IGG-RFB4-DGA (Combotox) in Patients With Refractory CD19(+), CD22(+) B Cell Lymphoma", Clinical Cancer Research, The American Association for Cancer Research, US, vol. 6, No. 4, Apr. 1, 2000, p. 1302-1313.
Kasman, L M, et al., Phage display of a biologically active *Bacillus thuringiensis* toxin, Applied and Environmental Microbiology, American Society for Microbiology, US, vol. 64., No. 8, Jan. 1, 1998, pp. 2995-3003.

Ho, M et al., In vitro antibody evolution targeting germline hot spots to increase activity of an anti-CD22 immunotoxin, Journal of Biological Chemistry, American Society for Biochemistry and Molecular Biology, Inc., vol. 280, No. 1, Jan. 7, 2005, pp. 607-617.

Art Branch: "Gene Library [Definition]", Retrieved from the Internet: URL:http://www.medicaldictionaryweb.com/Gene+Library-definition/ [retrieved on Sep. 23, 2011].

Art Branch: "Peptide Library [Definition]", Retrieved from the Internet: URL:http://www.medicaldictionaryweb.com/Peptide+Library-definition/ [retrieved on Dec. 19, 2011].

Kreitman, R.J., "Recombinant toxins in haematologic malignancies and solid tumours", Expert Opinion on Investigational Drugs, 1998, vol. 7, No. 9, pp. 1405-1427.

Di Paolo, C., et al., "A recombinant immunotoxin derived from a humanized epithelial cell adhesion molecule-specific single-chain antibody fragment has potent and selective antitumor activity", Clinical Cancer Research, 2003, vol. 9, No. 7, pp. 2837-2848.

Ho et al., In Vitro Antibody Evolution Targeting Germline Hot Spots to Increase Activity of an Anti-CD22 Immunotoxin, *The Journal of Biological Chemistry* (Jan. 7, 2005), 280(1):607-617.

* cited by examiner

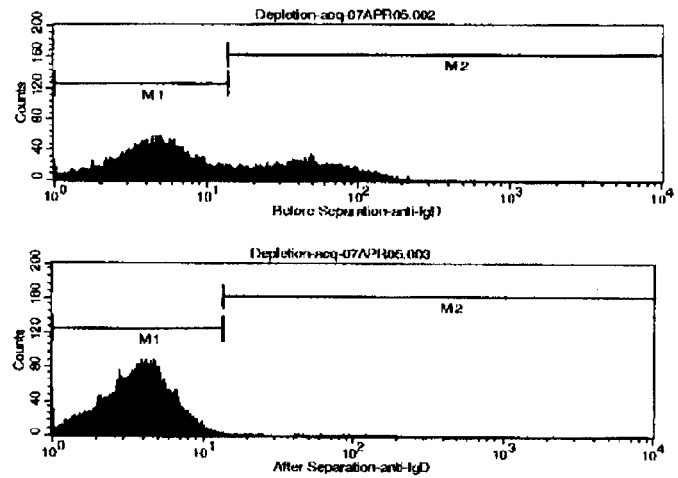

Figure 1: Depletion of B cells. The mixture of cells extracted from lymph node were labeled with Anti-IgD-FITC conjugate prior (upper graph) and after depletion (lower graph). The gating of live cells identified two populations, M1 and M2 which represent unlabeled and labeled cells, respectively.

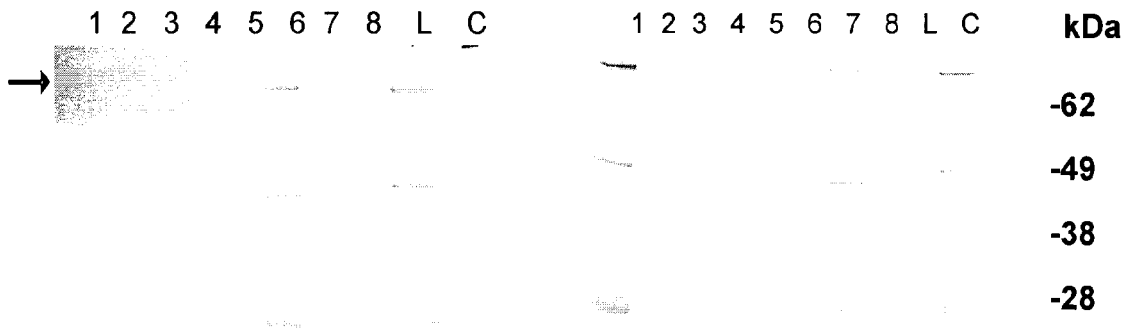

Figure 2: Western blot analysis of induced clones of the immune library. The supernatant, 16 µL, of 15 independent clones grown and induced in 96 well plate was loaded under non-reducing conditions on a SDS–PAGE gel and immunoblotted with an anti-human Kappa light chain-HRP antibody (1/1000). L and C correspond to the ladder and the induced supernatant of VB6-845-FAB-ETA$_{(252\text{-}608)}$, respectively. The arrow indicates the full-length protein migrating approximately at 75 kDa.

Flow cytometry analysis of affinity matured VL clone of VB6-011ETA$_{(252-608)}$ on MDA-435S cells. N1= supernatant from untransfected E-coli, 3302= Ecoli vector with not insert, 845 VB6-845 ETA$_{(252-608)}$ positive control, WT= original VB6-011 ETA$_{(252-608)}$, VL-1 to VL-4 VB6-011 ETA$_{(252-608)}$ with affinity matured light chains.

FIGURE 8

ELISA for CSA binding of affinity matured light chain VB6-011 ETA$_{(252-608)}$-VL2 compared with wild type and controls.

Flow cytometery of Affinity matured light and heavy chains clones for VB6-011. PBS negative control, VB3-011 wild type parent antibody, VL-2 VB6-011 ETA$_{(252-608)}$ wild type heavy chain with affinity matured light chain, N-1 supernatent from uninduced VL-2 clone, 20A10, 2D3, 11F11 and 8E8 various clones with affinity matured light and heavy chains.

FIGURE 10

Sequence of affinity matured VB6-011 2D3

V_H 011-2D3

QVQLVESGGGVVQPGRSLGLSCAASGFPFRAFAMHWVRQALGKGLEWVAVI SYDGMCKSYADSVKGRFTISRDTSKNTVYLKMNSLKTEDTAVYYCARDQTLL GDYDHYYMMDVWGKRTTVTVSS

V_L 011-2D3

DIVLTQSPGTLSLSPGERATLSCRALKAVWLEYLAWYQQKPGQAPRLLIYGAS TRATGMPDRFSGSGSGTDFTLTISRLEPEDFAVYYCLPCGGAPQTPQITFGGG TKVEIKR

Flow Cytometery for binding of optimized affinity matured VB6-011 2D3 boug compared with parental VB6-011 and positive control VB6-845.

METHODS FOR GENERATING AND SCREENING FUSION PROTEIN LIBRARIES AND USES THEREOF

CROSS REFERENCE TO RELATED APPLICATIONS

This application is a §371 U.S. national phase application of, International Application No. PCT/CA2006/002113, filed Dec. 22, 2006, which claims priority to U.S. Provisional Application No. 60/752,871, filed Dec. 23, 2005, each of which are incorporated by reference herein in its entirety.

FIELD OF THE INVENTION

The invention relates to methods for generating fusion protein libraries, in particular immunotoxin libraries. The invention also relates to the libraries themselves and the use of the libraries to screen for fusion proteins that are specific for target cells, such as cancer cells. In addition, the invention relates to methods of affinity maturation of immunotoxins and to the resulting immunotoxins.

BACKGROUND OF THE INVENTION

Fusion proteins which comprise a protein that binds to a target cell linked to a protein that has a desired effector function have many applications. When the effector protein is a detection reagent such fusion proteins can be used in detecting or diagnosing conditions associated with the target cell or a protein expressed on the target cell. When the effector protein is a therapeutic such fusion proteins can be used to deliver the therapeutic to the target cell. Examples of therapeutic fusion proteins include immunotoxins that comprise a cancer specific ligand linked to a toxin that can kill the cancer cell.

A number of immunotoxins have been tested in recent years (Kreitman R J (1999) Immunotoxins in cancer therapy. Curr Opin Immunol 11:570-578; Kreitman R J (2000) Immunotoxins. Expert Opin Pharmacother 1:1117-1129; Wahl R L (1994) Experimental radioimmunotherapy. A brief overview. Cancer 73:989-992; Grossbard M L, Fidias P (1995) Prospects for immunotoxin therapy of non-Hodgkin's lymphoma. Clin Immunol Immunopathol 76:107-114; Jurcic J G, Caron P C, Scheinberg D A (1995) Monoclonal antibody therapy of leukemia and lymphoma. Adv Pharmacol 33:287-314; Lewis J P, DeNardo G L, DeNardo S J (1995) Radioimmunotherapy of lymphoma: a U C Davis experience. Hybridoma 14:115-120; Uckun F M, Reaman G H (1995) Immunotoxins for treatment of leukemia and lymphoma. Leuk Lymphoma 18:195-201; Kreitman R J, Wilson W H, Bergeron K, Raggio M, Stetler-Stevenson M, FitzGerald D J, Pastan I (2001) Efficacy of the anti-CD22 recombinant immunotoxin BL22 in chemotherapy-resistant hairy-cell leukemia. N Engl J Med 345:241-247). Most antibodies tested to date have been raised against known cancer markers in the form of mouse monoclonal antibodies, sometimes "humanized" through molecular engineering. Unfortunately, their targets are usually also present on subset of normal cells thus still causing some non-specific effect. Furthermore, these antibodies are basically mouse proteins that are being seen by the human patient's immune system as foreign proteins. The ensuing immune reaction and antibody response can result in a loss of efficacy or in side-effects.

Two strategies are routinely used to enhance the binding affinity of an antibody. One approach utilizes the resolution of the crystal structure of the Ab-Ag complex to identify the key residues involved in the antigen binding (Davies D. R., Cohen G. H. 1996. Interactions of protein antigens with antibodies. Proc Natl Acad. Sci. USA. 93:7-12). Subsequently, those residues can be mutated to enhance the interaction. However, this approach cannot be used if the antigen is not known. The other approach mimics an in vivo antigen stimulation that drives the affinity maturation of immunoglobulin produced by B cells. During the maturation of the immune response, the variable regions of the immunoglobulins are subjected to somatic mutations (Mc Heyzer-Williams M. 2003. B-cell signaling mechanism and activation. Fundamental Immunology, Fifth edition, pp: 195-225). This process, highly specific for the immune system, is characterized by the introduction of point mutations at a very high rate. It occurs only within the DNA fragments encoding the variable regions and excludes the conserved domains. The B cells expressing the somatically mutated variant antibody are then subjected to an antigen-mediated selection resulting in the selection of higher affinity immunoglobulin. In order to replicate this phenomenon in vitro, several approaches have been used to introduce mutations either by random or targeted processes. The random mutations can be introduced using error-prone PCR, chain shuffling or mutator *E. coli* strains (Clackson T. Hoogenboom N. R., Griffiths A. D. and Winter G. 1991 Making antibody fragments using phage display libraries. Nature 352:624-628; Hawkins R. E., Russell S. J. and Winter G. 1992. Selection of phage antibodies by binding affinity. Mimicking affinity maturation. J. Mol. Biol. 226:889-896; Low N., Holliger P. and Winter G. 1996. Mimicking somatic hypermutation: affinity maturation of antibodies displayed on bacteriophage using a bacterial mutator strain. J Mol. Biol. 260:359-368). This strategy leads to the creation of large libraries in which reactive clones are selected with a display technology such as ribosome, phage or yeast (Min L. 2000. Applications of display technology in protein analysis. Nat. Biotechnol. 18:1251-1256).

The targeted mutations of the CDRs, especially CDR3 of the light and heavy chains, have been shown to be an effective technique for increasing antibody affinity. Blocks of 3 to 4 amino acids of the CDR3 or specific regions called "hot-spots" are targeted for mutagenesis. Yang et al reported an increase of 420 fold of an anti-HIV gp120 Fab fragment by mutating four CDR residues (Yang W. P., Green K., Pinz-Sweeney S., Briones A. T., Burton D. R. and Barbas C. F. III. 1995. CDR walking mutagenesis for the affinity maturation of a potent human anti-HIV-1 antibody into picomolar range. J. Mol. Biol. 254:392-403). One mutation in the $V_L$ CDR3 combined with three mutations in the $V_H$ CDR3 of the C6.5 scFv yielded a 1230 fold increased affinity (Schier R., McCall A., Adams G. P., Marshall K. W., Merrit H., Yin M., Crawford R. S., Weiner L. M., Marks C. and Marks J. D. 1996. Isolation of picomolar affinity anti-c-erbB-2 single-chain Fv by molecular evolution of the complementary determining regions in the center of the antibody binding site. J. Mol. Biol. 263:551-567). By targeting the mutations of 3 to 4 amino acids, small libraries of $2\times10^5$ clones are sufficient to cover all possible combinations. The size of the library is suitable for a direct screening approach where the antibody fragment could be expressed as a soluble protein and tested for functionality.

There is a need for improved methods of identifying fusion proteins that bind specifically to target cells. In particular, there is a need for better methods to improve the screening and efficacy of immunotoxins.

SUMMARY OF THE INVENTION

The present inventors have developed novel libraries of recombinant cells comprising nucleic acid sequences encoding fusion proteins, libraries of fusion proteins, methods of making the libraries and uses of the libraries. The fusion proteins comprise 1) a ligand protein that can bind to a target molecule and 2) an effector molecule that can detect, effect the target and/or treat a target cell containing the target molecule. Creating libraries of fusion proteins that can be used to detect or treat a disease greatly facilitates the screening and selection of useful fusion proteins. In particular, screening can be conducted on complete fusion proteins rather than on each part of the fusion protein separately.

In a preferred embodiment, the fusion protein is an immunotoxin. Preparing an immunotoxin library is advantageous as it allows the screening of complete immunotoxins for efficacy in tumor cell binding and/or killing. Previously, a tumor specific antibody would be screened for tumor cell binding and useful antibodies would then be used to prepare an immunotoxin. The immunotoxin would then need to be screened for tumor cell killing. Therefore, an immunotoxin library greatly facilitates the selection of therapeutically useful immunotoxins and allows for methods to be automated and adapted to high throughput approaches.

Accordingly, one aspect of the invention is a method of generating a library of recombinant cells, wherein each recombinant cell comprises nucleic acid sequences encoding a fusion protein, comprising the steps of:
 (a) constructing a library of vectors, wherein each vector encodes a fusion protein and comprises 1) a nucleic acid sequence that encodes a ligand protein that binds to a target molecule linked to 2) a nucleic acid sequence encoding an effector molecule; and
 (b) transforming host cells with the library of vectors to produce a library of recombinant cells.

The invention also includes libraries of recombinant cells generated using the methods of the invention.

Another aspect of the invention is a method of generating a library of fusion proteins, comprising the steps:
 (a) constructing a library of vectors, wherein each vector encodes a fusion protein and comprises 1) a nucleic acid sequence that encodes a ligand protein that binds to a target molecule linked to 2) a nucleic acid sequence encoding an effector molecule;
 (b) transforming host cells with the library of vectors to produce a library of recombinant cells;
 (c) cloning the transformed host cells; and
 (d) expressing a library of fusion proteins, wherein the fusion protein is a soluble protein expressed by the host cells.

The invention also includes libraries of fusion proteins generated using the methods of the invention. In particular, the invention includes libraries of immunotoxins, comprising a plurality of heavy chain variable regions and a plurality of light chain variable regions derived from B cells from a subject, and wherein each immunotoxin in the library has one heavy chain variable region and one light chain variable region, and the light chain variable region or the heavy chain variable region is linked to a cytotoxin.

A further aspect of the invention is a method of screening a library of fusion proteins for binding to a target molecule, comprising the steps of:
 (a) providing a library of fusion proteins of the invention;
 (b) contacting the fusion proteins with a target molecule; and
 (c) determining the binding of one or more fusion proteins to the target molecule.

Another aspect of the invention is a method of screening a library of fusion proteins for cytotoxicity to a target cell containing the target molecule, comprising the steps of:
 (a) providing a library of fusion proteins of the invention;
 (b) contacting the fusion proteins with a target cell; and
 (c) determining the cytotoxicity of one or more fusion proteins to the target cell.

The invention also includes the fusion proteins that can be used to detect, treat or prevent a disease, such as cancer, identified through the methods of the invention. In addition, the invention includes methods of treating or preventing a disease, such as cancer, using the fusion proteins of the invention and to the uses of the fusion proteins to treat or prevent a disease, such as cancer.

An additional aspect of the invention is a method of making improved fusion proteins to prevent or treat a disease, such as cancer. In one embodiment, the improved fusion proteins has improved binding and/or improved cytotoxicity to a target molecule or target cell.

Accordingly, one embodiment of the invention is a method of making an improved fusion protein, comprising the steps:
 (a) providing a nucleic acid sequence encoding a ligand protein that can bind a target molecule;
 (b) introducing at least one point mutation in the nucleic acid sequence encoding the ligand protein to generate a library of nucleic acid sequences encoding a variant ligand protein;
 (c) constructing a library of vectors, wherein each vector encodes a fusion protein and comprises 1) one of the variant ligand protein nucleic acid sequences made in step (b) and linked to 2) a nucleic acid sequence encoding an effector molecule;
 (d) transforming host cells with the library of vectors to produce a library of recombinant cells;
 (e) cloning the transformed host cells;
 (f) expressing a library of fusion proteins, wherein the fusion protein is a soluble protein expressed by the host cells; and
 (g) screening the library of fusion proteins for improved activity as compared to a non-modified fusion protein, wherein improved activity is indicative of an improved fusion protein.

In another embodiment, the method is for making an improved immunotoxin and comprises the steps:
 (a) providing a nucleic acid sequence of a light chain variable region and a heavy chain region variable of an antibody or immunotoxin;
 (b) introducing at least one point mutation in the nucleic acid sequence encoding the light chain variable region and/or the heavy chain variable region to generate a library of nucleic acid sequences encoding variant light chain and/or heavy chain variable regions;
 (c) constructing a library of vectors, wherein each vector encodes an immunotoxin and comprises one of the variant light chain variable region nucleic acid sequences and/or one of the variant heavy chain variable region nucleic acid sequences, and wherein the variant light chain variable region nucleic acid sequence and/or the variant heavy chain variable region nucleic acid sequence is operatively linked to a nucleic acid sequence encoding a cytotoxin;
 (d) transforming host cells with the library of vectors to produce a library of recombinant cells;
 (e) cloning the transformed host cells;
 (f) expressing a library of immunotoxins, wherein the immunotoxin is a soluble protein expressed by the host cells; and
 (g) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

A person skilled in the art will appreciate that targeted mutations of the heavy chain and/or light chain variable regions can be used to create the library, for example, in the hot spots in the light chain and/or heavy chain variable regions. In the case of receptor ligand mutations to the receptor binding domain or in the case of proteins that form complexes, mutations in the dimerization motif can be done.

In one embodiment, the method of making an improved immunotoxin, comprises the steps:
  (a) providing a nucleic acid sequence of a light chain variable region and a heavy chain region variable of an antibody or immunotoxin;
  (b) identifying the hot spots in the light chain variable region;
  (c) introducing at least one point mutation in the nucleic acid sequence encoding the light chain variable region at the hot spots to generate a library of nucleic acid sequences encoding variant light chain variable regions;
  (d) constructing a library of vectors, wherein each vector encodes an immunotoxin and comprises one of the variant light chain variable region nucleic acid sequences made in step (c) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;
  (e) transforming host cells with the library of vectors to produce a library of recombinant cells;
  (f) cloning the transformed host cells;
  (g) expressing a library of immunotoxins, wherein the immunotoxin is a soluble protein expressed by the host cells; and
  (h) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

In another embodiment, the method comprises the steps:
  (a) providing a nucleic acid sequence of a light chain variable region and a heavy chain region variable of an antibody or immunotoxin;
  (b) identifying the hot spots in the heavy chain variable region;
  (c) introducing at least one point mutation in the nucleic acid sequence encoding the heavy chain variable region at the hot spots to generate a library of nucleic acid sequences encoding variant heavy chain variable regions;
  (d) constructing a library of vectors, wherein each vector encodes an immunotoxin and comprises one of the variant heavy chain variable region nucleic acid sequences made in step (c) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;
  (e) transforming host cells with the library of vectors to produce a library of recombinant cells;
  (f) cloning the transformed host cells;
  (g) expressing a library of immunotoxins, wherein the immunotoxin is a soluble protein expressed by the host cells; and
  (h) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

The invention also includes variations to the above methods, for example, the methods can combine mutating both the heavy chain variable region and the light chain variable region. In one embodiment, the heavy chain variable regions and light chain variable regions can be mutated and screened sequentially. In another embodiment, the heavy chain variable regions and light chain variable regions can be mutated and screened at the same time.

Accordingly, another embodiment of the invention is a method of making an improved immunotoxin, comprising the steps:
  (a) providing a nucleic acid sequence of a light chain variable region and a heavy chain region variable of an antibody or immunotoxin;
  (b) introducing at least one point mutation in the nucleic acid sequence encoding the light chain variable region to generate a library of nucleic acid sequences encoding variant light chain variable regions;
  (c) constructing a library of vectors, wherein each vector encodes an immunotoxin and comprises one of the variant light chain variable region nucleic acid sequences made in step (b) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;
  (d) transforming host cells with the library of vectors to produce a library of recombinant cells;
  (e) cloning the transformed host cells;
  (f) expressing a library of immunotoxins, wherein the immunotoxin is a soluble protein expressed by the host cells;
  (g) screening the library of immunotoxins for improved binding and/or cytotoxicity to a target cell as compared to the non-modified antibody or immunotoxin of step (a), wherein improved binding and/or cytotoxicity to the target cell as compared to the non-modified antibody or immunotoxin is indicative of an improved immunotoxin;
  (h) introducing at least one point mutation in the nucleic acid sequence encoding the heavy chain variable region to generate a library of nucleic acid sequences encoding variant heavy chain variable regions;
  (i) constructing a library of vectors, wherein each vector encodes an immunotoxin and comprises one of the variant heavy chain variable region nucleic acid sequences made in step (h) and/or the variant light chain variable region nucleic acid sequence of the improved immunotoxin identified in step (h), and wherein the variant heavy chain variable region nucleic acid sequence or the variant light chain variable region nucleic acid sequence is operatively linked to a nucleic acid sequence encoding a cytotoxin;
  (j) transforming host cells with the library of vectors to produce a library of recombinant cells;
  (k) cloning the transformed host cells;

(l) expressing a library of immunotoxins, wherein the immunotoxin is a soluble protein expressed by the host cells; and (m) screening the library of immunotoxins for improved binding and/or improved cytotoxicity to a target cell as compared to the non-modified antibody or immunotoxin, wherein improved binding and/or improved cytotoxicity to the target cell as compared to the non-modified antibody or immunotoxin is indicative of an improved immunotoxin.

Further the invention includes a method of making an improved immunotoxin, comprising the steps:

(a) providing a nucleic acid sequence of a light chain variable region and a heavy chain region variable of an antibody or immunotoxin;

(b) introducing at least one point mutation in the nucleic acid sequence encoding the heavy chain variable region to generate a library of nucleic acid sequences encoding variant heavy chain variable regions;

(c) constructing a library of vectors, wherein each vector encodes an immunotoxin and comprises one of the variant heavy chain variable region nucleic acid sequences made in step (b) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;

(d) transforming host cells with the library of vectors to produce a library of recombinant cells;

(e) cloning the transformed host cells;

(f) expressing a library of immunotoxins, wherein the immunotoxin is a soluble protein expressed by the host cells;

(g) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin;

(h) introducing at least one point mutation in the nucleic acid sequence encoding the light chain variable region to generate a library of nucleic acid sequences encoding variant light chain variable regions;

(i) constructing a library of vectors, wherein each vector encodes an immunotoxin and comprises one of the variant light chain variable region nucleic acid sequences made in step (h) and/or the variant heavy chain variable region nucleic acid sequence of the improved immunotoxin identified in step (g), and wherein the variant light chain variable region nucleic acid sequence or the variant heavy chain variable region nucleic acid sequence is operatively linked to a nucleic acid sequence encoding a cytotoxin;

(j) transforming host cells with the library of vectors to produce a library of recombinant cells;

(k) cloning the transformed host cells;

(l) expressing a library of immunotoxins, wherein the immunotoxin is a soluble protein expressed by the host cells; and (m) screening the library of immunotoxins for improved binding and/or improved cytotoxicity to a target cell as compared to the non-modified antibody or immunotoxin, wherein improved binding to the target cell and/or improved cytotoxicity to the target cell as compared to the non-modified antibody or immunotoxin is indicative of an improved immunotoxin.

Accordingly, another embodiment of the invention is a method of making an improved immunotoxin, comprising the steps:

(a) providing a nucleic acid sequence of a light chain variable region and a heavy chain region variable of an antibody or immunotoxin;

(b) identifying the hot spots in the light chain variable region;

(c) introducing at least one point mutation in the nucleic acid sequence encoding the light chain variable region at the hot spots to generate a library of nucleic acid sequences encoding variant light chain variable regions;

(d) constructing a library of vectors, wherein each vector encodes an immunotoxin and comprises one of the variant light chain variable region nucleic acid sequences made in step (c) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;

(e) transforming host cells with the library of vectors to produce a library of recombinant cells;

(f) cloning the transformed host cells;

(g) expressing a library of immunotoxins, wherein the immunotoxin is a soluble protein expressed by the host cells;

(h) screening the library of immunotoxins for improved binding and/or cytotoxicity to a target cell as compared to the non-modified antibody or immunotoxin of step (a), wherein improved binding and/or cytotoxicity to the target cell as compared to the non-modified antibody or immunotoxin is indicative of an improved immunotoxin;

(i) identifying the hot spots in the heavy chain variable region;

(j) introducing at least one point mutation in the nucleic acid sequence encoding the heavy chain variable region at the hot spots to generate a library of nucleic acid sequences encoding variant heavy chain variable regions;

(k) constructing a library of vectors, wherein each vector encodes an immunotoxin and comprises one of the variant heavy chain variable region nucleic acid sequences made in step (j) and/or the variant light chain variable region nucleic acid sequence of the improved immunotoxin identified in step (h), and wherein the variant heavy chain variable region nucleic acid sequence or the variant light chain variable region nucleic acid sequence is operatively linked to a nucleic acid sequence encoding a cytotoxin;

(l) transforming host cells with the library of vectors to produce a library of recombinant cells;

(m) cloning the transformed host cells;

(n) expressing a library of immunotoxins, wherein the immunotoxin is a soluble protein expressed by the host cells; and (o) screening the library of immunotoxins for improved binding and/or improved cytotoxicity to a target cell as compared to the non-modified antibody or immunotoxin, wherein improved binding and/or improved cytotoxicity to the target cell as compared to the non-modified antibody or immunotoxin is indicative of an improved immunotoxin.

Further the invention includes a method of making an improved immunotoxin, comprising the steps:
  (a) providing a nucleic acid sequence of a light chain variable region and a heavy chain region variable of an antibody or immunotoxin;
  (b) identifying the hot spots in the heavy chain variable region;
  (c) introducing at least one point mutation in the nucleic acid sequence encoding the heavy chain variable region at the hot spots to generate a library of nucleic acid sequences encoding variant heavy chain variable regions;
  (d) constructing a library of vectors, wherein each vector encodes an immunotoxin and comprises one of the variant heavy chain variable region nucleic acid sequences made in step (c) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;
  (e) transforming host cells with the library of vectors to produce a library of recombinant cells;
  (f) cloning the transformed host cells;
  (g) expressing a library of immunotoxins, wherein the immunotoxin is a soluble protein expressed by the host cells;
  (h) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin;
  (i) identifying the hot spots in the light chain variable region;
  (j) introducing at least one point mutation in the nucleic acid sequence encoding the light chain variable region at the hot spots to generate a library of nucleic acid sequences encoding variant light chain variable regions;
  (k) constructing a library of vectors, wherein each vector encodes an immunotoxin and comprises one of the variant light chain variable region nucleic acid sequences made in step (j) and/or the variant heavy chain variable region nucleic acid sequence of the improved immunotoxin identified in step (h), and wherein the variant light chain variable region nucleic acid sequence or the variant heavy chain variable region nucleic acid sequence is operatively linked to a nucleic acid sequence encoding a cytotoxin;
  (l) transforming host cells with the library of vectors to produce a library of recombinant cells;
  (m) cloning the transformed host cells;
  (n) expressing a library of immunotoxins, wherein the immunotoxin is a soluble protein expressed by the host cells; and
  (o) screening the library of immunotoxins for improved binding and/or improved cytotoxicity to a target cell as compared to the non-modified antibody or immunotoxin, wherein improved binding to the target cell and/or improved cytotoxicity to the target cell as compared to the non-modified antibody or immunotoxin is indicative of an improved immunotoxin.

The invention also includes the improved immunotoxins. In addition, the invention includes the use of the improved immunotoxins to treat or prevent a disease, such as cancer, and methods of treating or preventing a disease, such as cancer, using the improved immunotoxins of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 is a flow diagram of the depletion of immatured B cells from the patient B-cell population. The mixture of cells extracted from lymph node were labeled with Anti-IgD-FITC conjugate prior (upper graph) and after depletion (lower graph). The gating of live cells identified two populations, M1 and M2 which represent unlabeled and labeled cells, respectively. The removal of labeled cells indicates the removal of immatured B-cells.

FIG. 2 is a Western blot analysis of induced clones of the immune library. The supernatant, 16 µL, of 15 independent clones grown and induced in 96 well plate was loaded under non-reducing conditions on a SDS-PAGE gel and immunoblotted with an anti-human Kappa light chain-HRP antibody (1/1000). L and C correspond to the ladder and the induced supernatant of VB6-845-FAB-ETA$_{(252-608)}$, respectively. The arrow indicates the full-length antibody migrating approximately at 75 kDa is expressed by the clones.

FIG. 8 is an ELISA for recognition of the chrondroitin sulfate A by affinity matured light chain VB6-011-ETA$_{(252-608)}$-VL2 compared with wild type and controls.

FIG. 10 is the amino acid Sequence of the affinity matured VB6-011 clone 2D3 (SEQ ID NOS:1 and 2).

Figure 3:
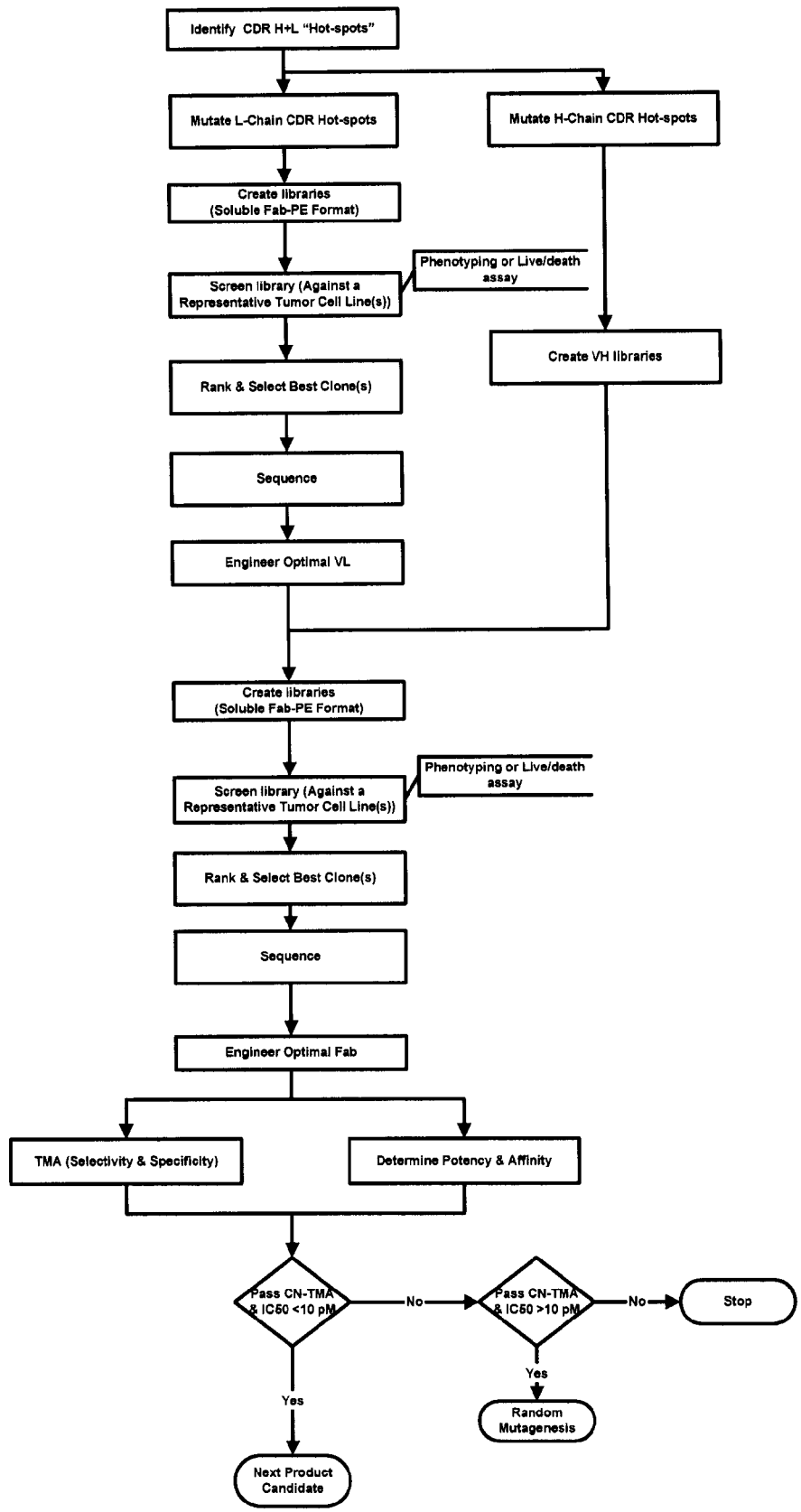
FIG. 3 is an affinity maturation algorithm.

DETAILED DESCRIPTION OF THE INVENTION (A) Definitions

The term "amino acid" includes all of the naturally occurring amino acids as well as modified amino acids.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

The term "B cell or B lymphocyte" as used herein refers to a lymphocyte that provides humoral immunity. A "mature B cell" refers to a B cell that has been stimulated by an antigen and has matured into a plasma cell that produces antibodies specific for the antigen.

The term "disease" as used herein refers to any medical condition or disorder that results in recognizable signs and/or symptoms. In a preferred, embodiment the disease is cancer.

The term "fusion protein" as used herein means a recombinant protein comprising 1) a ligand protein that binds to a target cell linked to 2) an effector molecule.

The phrase "effective amount" as used herein means an amount effective, at dosages and for periods of time necessary to achieve the desired result. Effective amounts of a fusion protein may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "effector molecule" as used herein means any molecule that one wishes to link to a ligand protein including, without limitation, therapeutic proteins, diagnostic proteins and proteins or fragments thereof that are useful in assisting the linking of the ligand protein to an effector molecule.

The term "immunotoxin" as used herein means a fusion protein comprising a light chain variable region and/or a heavy chain variable region, wherein either the light chain variable region or the heavy chain variable region is linked to a cytotoxin.

The term "hot-spots" as used herein refers to the specific nucleotide sequences in the light chain and heavy chain variable region where somatic hypermutation takes place in vivo. In one embodiment, the hot-spot includes the tetranucleotide, RGYW, in which R can be either A or G, Y can be C or T and W can be either A or T. In another embodiment, the hot-spot includes the nucleotides AGY.

The term "library" as used herein refers to a collection of different, but related items. For example, a "library of recombinant cells" as used herein refers to a collection of different recombinant cells. In a preferred embodiment, each recombinant cell comprises nucleic acid sequences encoding a fusion protein. In another example, a "library of nucleic acid sequences" refers to a collection of different nucleic acid sequences. In a preferred embodiment, the each nucleic acid sequence in the library encodes the light chain variable regions and/or heavy chain variable regions of an antibody. The phrase "a library of vectors" as used herein refers to a collection of different vectors. In a preferred embodiment, the each vector comprises a nucleic acid sequence that encodes a ligand protein operatively linked to a nucleic acid molecule that encodes an effector molecule. A "library of fusion proteins" as used herein refers to a collection of different fusion proteins. In one embodiment, the library of immunotoxins comprises light chain variable regions and/or heavy chain variable regions that have been mutated for use in affinity maturation.

The term "modified bouganin" as used here means a modified bouganin that has a reduced propensity to activate an immune response as described in International Publication NO. WO/2005/090579 and United States Publication No. 2005/0238642. In one example, the modified bouganin has the amino acid sequence:

(SEQ ID NO: 88)
YNTVSFNLGEAYEYPTFIQDLRNELAKGTPVCQLPVTLQTIADDKRFVL

VDITTTSKKTVKVAIDVTDVYVVGYQDKWDGKDRAVFLDKVPTVATSK

LFPGVTNRVTLTFDGSYQKLVNAAKADRKALELGVNKLEFSIEAIHGKTI

NGQEAAKFFLIVIQMVSEAARFKYIETEVVDRGLYGSFKPNFKVLNLEN

NWGDISDAIHKSSPQCTTINPALQLISPSNDPWVVNKVSQISPDMGILK

FKSSK.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The term includes either double stranded or single stranded DNA or RNA.

The term "subject" as used herein refers to any member of the animal kingdom that has B cells. In a preferred embodiment, the subject is a mammal. In a more preferred embodiment, the subject is a human being.

The term "target molecule" as used herein means a molecule that binds to a ligand protein of the invention. The molecule may be an antigen on a target cell or an isolated antigen including an immobilized antigen.

The term "target cell" as used herein refers to any cell that has a target molecule that binds a ligand protein of the invention. In one embodiment the cell is a cancer cell.

The phrase "treating cancer" as used herein refers to inhibiting cancer cell replication, inhibiting cancer spread (metastasis), inhibiting tumor growth, reducing cancer cell number or tumor growth, decreasing the malignant grade of a cancer (e.g., increased differentiation), or improving cancer-related symptoms.

(B) Libraries of Recombinant Cells and Fusion Proteins

As mentioned previously, preparing a library of cells expressing fusion proteins is advantageous as it facilitates the screening of fusion proteins for therapeutic or diagnostic utility. Some of the advantages of the present invention include, without limitation, the following:
1. Screening with a fusion protein rather than a ligand protein is efficient as it avoids the step of having to first screen the ligand before preparing the fusion protein.
2. Improves the selection of ligand proteins such as antibodies whose binding and internalization characteristics are not compromised in a fusion protein format.
3. May allow for the screening of unpurified supernatants as the effector molecule is effective even when not purified.
4. Allows for the selection of fusion proteins that bind to unknown antigens on target cells. In such a case, the effector molecule can be a toxin and the screening parameters can be cell death.

Accordingly, one aspect of the invention is a method of generating a library of recombinant cells, wherein each recombinant cell comprises nucleic acid sequences encoding a fusion protein, comprising the steps of:
 (a) constructing a library of vectors, wherein each vector encodes a fusion protein and comprises 1) a nucleic acid sequence that encodes a ligand protein that binds to a target molecule linked to 2) a nucleic acid sequence encoding an effector molecule; and
 (b) transforming host cells with the library of vectors to produce a library of recombinant cells.

The ligand protein can be any protein that can bind a target molecule including, without limitation, antibodies, antibody fragments, receptor binding proteins, transcription factors and complex forming proteins.

In a preferred embodiment, the ligand is an antibody or antibody fragment. Antibody fragments that may be used include Fab, Fab', F(ab')$_2$, scFv and dsFv fragments from recombinant sources. The antibody or fragment may be from any species including mice, rats, rabbits, hamsters and humans. Chimeric antibody derivatives, i.e., antibody molecules that combine a non-human animal variable region and a human constant region are also contemplated within the scope of the invention. Chimeric antibody molecules can include, for example, humanized antibodies which comprise the antigen binding domain from an antibody of a mouse, rat, or other species, with human constant regions.

The ligand portion of the fusion protein may be immunoglobulin derived, i.e., can be traced to a starting molecule that is an immunoglobulin (or antibody). For example, the ligand may be produced by modification of an immunoglobulin scaffold using standard techniques known in the art. In another, non-limiting example, immunoglobulin domains (e.g., variable heavy and/or light chains) may be linked to a non-immunoglobulin scaffold.

The ligand portion of the immunotoxin need not be immunoglobulin based. For example, the ligand may comprise an Affibody®, or variant thereof, that specifically binds to target cells. Such non-immunoglobulin polypeptide ligands can be designed to bind to a target tumor associated molecule. Moreover, non-immunoglobulin polypeptide ligands can be engineered to a desired affinity or avidity, and can be designed to tolerate a variety of physical conditions, including extreme pH ranges and relatively high temperature. The design of a non-immunoglobulin polypeptide with a relatively long half-life at physiological conditions (e.g., 37° C. in the presence of peptidases) can be advantageous. Furthermore, such molecules, or variants thereof, may demonstrate good solubility, small size, proper folding and can be expressed in readily available, low-cost bacterial systems, and thus manufactured in commercially reasonable quantities. The ability to design a non-immunoglobulin polypeptide is within the skill of the ordinary artisan. See, e.g., U.S. Pat. Nos. 5,831,012 and 6,534,628 for techniques generally adaptable to design, manufacture, and select desired binding partners.

The ligand may be a protein that binds an epitope on the target cell. Examples of epitope-binding polypeptides include, without limitation, ligands comprising a fibronectin type III domain (see, e.g., International Publication Nos. WO 01/64942, WO 00/34784, WO 02/32925). Protein A-based affinity libraries have also been used to identify epitope-binding polypeptides (see, e.g., U.S. Pat. Nos. 5,831,012 and 6,534,628) and such libraries may be useful in accordance with the present invention to select polypeptides that selectively bind to target cells.

Other types of binding molecules are known in the art including, without limitation, binding molecules based on assembly of repeat protein domains (see, e.g., Forrer et al., 2003, "A novel strategy to design binding molecules harnessing the modular nature of repeat proteins." FEBS Lett. 539: 2-6; Kohl et al., 2003, "Designed to be stable: crystal structure of a consensus ankyrin repeat protein." Proc Natl Acad Sci USA. 100:1700-1705). Libraries of randomly assembled repeat domains may be useful in accordance with the present invention to select ligands that selectively bind to target cells.

Several non-immunoglobulin based, epitope-binding polypeptides and methods for making and using such polypeptides are known in the art (see, e.g., Eklund et al., 2002, "Anti-idiotypic protein domains selected from Protein A-based affibody libraries." Prot. Struct. Funct. Gen. 48:454-462; Gunneriusson et al., 1999, "Affinity maturation of a Taq DNA polymerase specific affibody by helix shuffling." Prot. Eng. 12:873-878; Hansson et al., 1999, "An in vitro selected binding protein (affibody) shows conformation-dependent recognition of the respiratory syncytial virus (RSV) G protein." Immunotechnol. 4: 237-252; Henning et al., 2002, "Genetic modification of adenovirus 5 tropism by a novel class of ligands based on a three-helix bundle scaffold derived from staphylococcal protein A." Human Gene Therapy 13:1427-1439; Högbom et al., 2003, "Structural basis for recognition by an in vitro evolved affibody. Proc Natl Acad Sci USA. 100(6):3191-3196; Nord et al., 1997, "Binding proteins selected from combinatorial libraries of an -helical bacterial receptor domain." Nature Biotechnol. 15:772-777; Nord et al., 2000, "Ligands selected from combinatorial libraries of protein A for use in affinity capture of apolipoprotein A-1M and Taq DNA polymerase." J. Biotechnol. 80:45-54; Nord et al., 1995, "A combinatorial library of an alpha-helical bacterial receptor domain." Prot. Eng. 8:601-608; Nord et al., 2001, "Recombinant human factor VII-specific affinity ligands selected from phage-displayed combinatorial libraries of protein A." Eur. J. Biochem. 268:1-10; Nygren et al., 1997, "Scaffolds for engineering novel binding sites in proteins." Curr. Opin. Struct. Biol. 7:463-469; Rönnmark et al., 2002, "Human immunoglobin A (IgA)-specific ligands from combinatorial engineering of protein A." Eur. J. Biochem. 269:2647-2655; Rönnmark et al., 2002, "Construction and characterization of affibody-Fc chimeras produced in *Escherichia coli*." J. Immunol. Meth. 261:199-211; Wahlberg et al., 2003, "An affibody in complex with a target protein: structure and coupled folding." Proc Natl Acad Sci USA. 100(6):3185-3190; Gotz et al., 2002, "Ultrafast electron transfer in the complex between fluorescein and a cognate engineered lipocalin protein, a so-called anticalin." Biochemistry. 41:4156-4164; Skerra, 2001, "Anticalins: a new class of engineered ligand-binding proteins with antibody-like properties." J Biotechnol. 2001 74:257-275; Skerra, 2000, "Lipocalins as a scaffold." Biochim Biophys Acta. 1482:337-350; Skerra et al., 2000, "Engineered protein scaffolds for molecular recognition." J Mol Recognit. 13:167-187; Schlehuber et al., 2000, "A novel type of receptor protein, based on the lipocalin scaffold, with specificity for digoxigenin." J Mol Biol. 297:1105-1120; Beste et al., 1999, "Small antibody-like proteins with prescribed ligand specificities derived from the lipocalin fold." Proc Natl Acad Sci USA. 96:1898-1903; PCT International Publication No. WO97/45538 entitled "Novel Synthetic Protein Structural Templates For The Generation, Screening And Evolution Of Functional Molecular Surfaces" (relating to production of libraries of peptide sequences in the framework of a structural template derived from Pleckstrin-Homology (PH) domains).

The effector molecule is preferably any protein that has a desired effect on the target molecule or cell. Examples of effector molecules include, without limitation, proteins that are useful in the detection or treatment of the target molecule or cell.

Diagnostic proteins can be any protein that can detect the target molecule in a suitable assay. Examples of diagnostic proteins include, without limitation, fluorescent proteins such as luciferase or green fluorescent protein. Assaying for their presence can be done using known techniques such as microscopy or scanning fluorescent plate readers with appropriate filter.

Therapeutic proteins can be any protein that has a desired therapeutic effect on the target cell. Examples of therapeutic proteins include, without limitation, toxins, cytokines, growth hormones, enzymes, tumor suppressors, transcriptional regulators and nucleotide binding proteins.

In addition to diagnostic and therapeutic molecules, additional residues can be added to the end of the ligand proteins such as cysteines with reactive groups or recombinant polypeptides (Kaufmann and Weberskirch, 2006, Flennicken et al 2005; U.S. Pat. No. 6,747,135 Nolan et al.) for easy chemical modifications for the addition of radioactive isotopes, fluorescent markers or anti-cancer drugs. The added residues can be selected based on the requirements of the chemistry for the intended marker to be added. Assays would include as above for the fluorescent, or scintillation counting for the radioactive or cell growth/cell death assays (MTT, FMAT, BrDu incorporation) for anti-cancer drugs.

One aspect of the invention is a method of generating a library of recombinant cells, wherein each recombinant cell comprises nucleic acid sequences encoding an immunotoxin, comprising the steps of:

(a) constructing a library of vectors, wherein each vector encodes an immunotoxin and comprises one light chain variable region nucleic acid sequence and/or one heavy chain variable region nucleic acid sequence from the library of nucleic acid sequences, and wherein the light chain variable region nucleic acid sequence or the heavy chain variable region nucleic acid sequence is operatively linked to a nucleic acid sequence encoding a cytotoxin; and (b) transforming host cells with the library of vectors to produce a library of recombinant cells.

The nucleic acid sequences encoding the light chain and/or heavy chain variable regions can be obtained from a suitable source such as from B cells. The source of the B cells can be from a subject that has a disease or a subject that does not have a disease. In a preferred embodiment, the B cells are from a subject that has a disease, such as cancer.

In one embodiment, the source of the B cells is from a subject who has any type of cancer. In one embodiment, the cancer includes, without limitation, stomach cancer, colon cancer, prostate cancer, cervical cancer, skin cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, endometrial cancer, plasmacytoma, lymphoma, or melanoma.

The B cells can be isolated from a sample from a subject. The sample can be any fluid, cell or tissue sample from a subject that contains B cells. In one embodiment, the sample is lymph node tissue, lymphatic fluid, or whole blood.

In another embodiment of the invention, mature B cells are used as a source to create the library.

A person skilled in the art will appreciate that a number of methods can be used to isolate mature B cells from a sample from a subject. For example, the mature B cells can be isolated from the sample using negative selection of unwanted cells or positive selection of the cells of interest. In one embodiment of the invention, B cells are selected for using an antibody specific for CD19. In another embodiment of the invention, naïve B cells are removed from the sample using an antibody specific for IgD. In a further embodiment, mature B cells are selected for using an antibody specific for CD38.

In order to ensure that there are ample numbers of B cells for use in the method of the invention. The B cells can be quantified. For example, if mature B cells are used, then an antibody specific for CD38, which is a surface marker strongly expressed by mature B cells, can be used. In a preferred embodiment, more than $10^6$ B cells are used in the method of the invention. It is possible to pool the B cells from more than one subject to ensure an adequate starting number of B cells for use in the method of the invention.

In the method of the invention, a library of vectors is constructed wherein each vector encodes an immunotoxin and comprises one light chain variable region nucleic acid sequence and/or one heavy chain variable region nucleic acid sequence from the library of nucleic acid sequences. A person skilled in the art will appreciate that the light chain variable region nucleic acid sequence can be on the same vector or a different vector than the heavy chain variable region nucleic acid sequence.

The immunotoxins comprise a light chain variable region and a heavy chain variable region, wherein either the light chain variable region or the heavy chain variable region is operatively linked to a therapeutic agent, such as a cytotoxin that is either cytotoxic, cytostatic or otherwise prevents or reduces the ability of the cells to divide and/or metastasize. Operatively linked is intended to mean that the light chain variable region or heavy chain variable region is linked to the cytotoxin in a manner which preserves the function of the light chain variable region or heavy chain variable region, and the cytotoxin. The cytotoxin may be operatively linked directly or indirectly to the light chain variable region or heavy chain variable region.

In one embodiment, the cytotoxin is a polypeptide having ribosome-inactivating activity including, without limitation, gelonin, bouganin, saporin, ricin, ricin A chain, bryodin, diphtheria toxin, restrictocin, *Pseudomonas* exotoxin A and variants thereof. When the cytotoxin is a ribosome-inactivating protein, the immunotoxin must be internalized upon binding to the cancer cell in order for the protein to be cytotoxic to the cells. Accordingly, in an embodiment of the invention, immunotoxin can be internalized by the cell.

In one embodiment of the invention, the toxin is bouganin or *Pseudomonas* exotoxin A, and variants thereof. In another embodiment, the toxin is modified bouganin or a truncated form of *Pseudomonas* exotoxin A that lack the cell binding domain. In a further embodiment the toxin is a bouganin substantially devoid of T-cell epitopes or a truncated form of *Pseudomonas* exotoxin A that consists of amino acids 252-608 and an endoplasmic reticulum retention sequence.

In a preferred embodiment, the therapeutic agent is a cytotoxin that is very toxic so that only limited quantities of the immunotoxin is needed to detect cytotoxicity against a cell in the screening methods of the invention. For example, in preferred embodiment *Pseudomonas* exotoxin A is used, more preferably a variant of the *Pseudomonas* exotoxin A that has disabled cell binding domain or that lacks the cell binding domain. In a further embodiment the toxin is a truncated form of *Pseudomonas* exotoxin A that consists of amino acids 252-608.

Recombinant methods are used in the method of the invention. For example recombinant methods can be used to isolate nucleic acid sequences encoding the light chain variable regions and heavy chain variable regions, and can be used to create a library of vectors, wherein each vector encodes an immunotoxin and comprises one light chain variable region nucleic acid sequence and one heavy chain variable region nucleic acid sequence, and either the light chain variable region nucleic acid sequence or the heavy chain variable region nucleic acid sequence is operatively linked to a nucleic acid sequence encoding a cytotoxin. In addition, recombinant methods can be used to generate the library of recombinant cells using the library of vectors.

Recombinant methods can also be used to generate the library of fusion proteins of the invention. For example, the recombinant cells of the invention can be cloned and then the fusion proteins encoded by the cells can be expressed. In a preferred, embodiment the fusion protein is expressed as a soluble protein.

The nucleic acid molecules of the present invention may be incorporated in a known manner into an appropriate expression vector which ensures good expression of the fusion proteins. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule used in the method of the invention and the necessary regulatory sequences for the transcription and translation of the fusion protein.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with the nucleic acid sequences used in the method of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the proteins of the invention may be expressed in prokaryotic cells, such as *Escherichia coli* (Zhang et al., Science 303(5656): 371-3 (2004)). In addition, a *Pseudomonas* based expression system, such as *Pseudomonas fluorescens*, can be used (US Patent Application Publication No. US 2005/0186666, Schneider, Jane C et al.).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Ito et al., J. Bacteriology 153:163 (1983), and Cullen et al. (Bio/Technology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., Mol. Cell Biol. 3:2156-2165 (1983)) and the pVL series (Luckow, V. A., and Summers, M. D., Virology 170:31-39 (1989)). Some baculovirus-insect cell expression systems suitable for expression of the recombinant proteins of the invention are described in PCT/US/02442.

Multiple vectors per recombinant cells can be inefficient and may cause degeneracy of the library, and thus is preferably avoided. Accordingly, in a preferred embodiment, the majority of the recombinant cells in the library of recombinant cells of the invention contain one vector from the library of vectors per recombinant cell, and the light chain and heavy chain variable regions are in the same vector. If the light chain and heavy chain variable regions are on separate vectors, then preferably, the majority of the recombinant cells in the library of recombinant cells of the invention contain two vectors from the library of vectors per recombinant cell, wherein one vector comprises nucleic acid sequences encoding the heavy chain variable region and the other vector comprises nucleic acid sequences encoding the light chain variable region. A person skilled in the art will appreciate that routine testing can be done to optimize the ratio of vectors per host cell for the transformation process, and that this ratio will vary depending on the DNA, host cell and method of transformation used.

The library of recombinant cells can be used to generate a library of fusion proteins. In one embodiment, a library of immunotoxins is generated according to the methods of the invention. In another embodiment, the invention includes libraries of immunotoxins, comprising a plurality of heavy chain variable regions and a plurality of light chain variable regions derived from B cells from a subject, and wherein each immunotoxin in the library has one heavy chain variable region and one light chain variable region, and the light chain variable region or the heavy chain variable region is linked to a nucleic acid sequence encoding a cytotoxin.

Another aspect of the invention is a method of screening a library of fusion proteins for binding to a target molecule, comprising the steps of:
(a) providing a library of fusion proteins of the invention;
(b) contacting the fusion proteins with a target molecule; and
(c) determining the binding of one or more fusion proteins to the target molecule.

The binding of the fusion protein to the target molecule can be determined using techniques known in the art including, without limitation, flow cytometry, fluorometric microvolume assay technology (FMAT) or enzyme-linked immunosorbent assay (ELISA).

The library of fusion proteins can also be screened for activity or function of the effector molecule. For example, when the effector molecule is a toxic molecule, the fusion protein can be screened for target cell killing. Another aspect of the invention is a method of screening a library of fusion proteins for cytotoxicity to a target cell, comprising the steps of:
(a) providing a library of fusion proteins of the invention;
(b) contacting the fusion proteins with a target cell; and
(c) determining the cytotoxicity of one or more fusion proteins to the target cell.

The cytotoxicity of the fusion protein to the target cell can be determined using techniques known in the art including, without limitation, the chromium-51 release assay, the MTS assay, annexin V apoptosis assay or cell proliferation assay such as BrDu incorporation ELISAS.

Other suitable assays can be developed depending on the nature of the effector molecule. For molecules that induce cell growth, cell growth or proliferation assays may be used. For diagnostic molecules, such as fluorescent proteins, these may be detected using known assays.

The target cell can be any cell that is bound by the fusion protein. The target generally expresses a target molecule or antigen that is recognized by the ligand portion of the fusion protein, for example, a disease associated antigen. In a preferred embodiment of the invention, the target cell is a diseased cell that expresses a disease associated antigen, in more a preferred embodiment the target cell is a cancer cell. In one embodiment, the cancer includes, without limitation, stomach cancer, colon cancer, prostate cancer, cervical cancer, skin cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, endometrial cancer, plasmacytoma, lymphoma, or melanoma.

The suitable controls can be used in the above methods to determine whether the fusion protein has a specific effect on the target cell including binding and/or killing the target cell. The control can be any cell that is known not to express the antigen of interest. For example, if the target cell is a cancer cell, then the control can be a non-cancerous cell.

Once a particular fusion protein has been selected, it is possible to replace the effector molecule with another effector molecule.

The invention includes the fusion proteins identified using the screening methods of the invention, and the use of the fusion proteins to prevent or treat a disease, such as cancer, or methods of treating or preventing a disease, such as cancer, by administering the fusion proteins of the invention.

The invention also includes the immunotoxins identified using the screening methods of the invention, and the use of the immunotoxins to prevent or treat a disease, such as cancer, or methods of treating or preventing a disease, such as cancer, by administering the immunotoxins of the invention.

(C) Affinity Maturation

Another aspect of the invention is a method of improving fusion proteins. The inventors have developed a novel method of using affinity maturation to improve binding and/or cytotoxicity of an immunotoxin using the libraries of the invention. The method of the invention encompasses the step of mutating the nucleotide sequences encoding the binding region of the fusion protein immunotoxin.

Conducting affinity maturation on a fusion protein such as an immunotoxin rather than just the binding ligand is advantageous and facilitates the preparation of improved fusion proteins. Prior to the present invention, for the preparation of immunotoxins, one would affinity mature the antibody and then prepare an immunotoxin with the affinity matured antibody. The present invention facilitates the method as it avoids the extra step of screening the antibody or binding ligand prior to the preparation of the fusion protein. In addition, mutating the fusion protein itself is more efficient as it avoids the selection of ligands that may work well on their own but not in a fusion protein such as an immunotoxin. Further, as mentioned previously, the methods of the present invention do not require prior knowledge of the target antigen and allows the use of unpurified supernatants.

In one embodiment, the ligand protein is mutated. Accordingly, the invention includes a method of making an improved fusion protein, comprising the steps:
(a) providing a nucleic acid sequence that encodes a ligand that binds to a target molecule;
(b) introducing at least one point mutation in the nucleic acid sequence encoding the ligand to generate a library of nucleic acid sequences encoding variant ligand proteins;
(c) constructing a library of vectors, wherein each vector encodes a fusion protein and comprises one of the variant ligand nucleic acid sequences made in step (b) linked to a nucleic acid sequence encoding an effector molecule;
(d) transforming host cells with the library of vectors to produce a library of recombinant cells;
(e) cloning the transformed host cells;
(f) expressing a library of fusion proteins, wherein the fusion protein is soluble protein expressed by the host cells; and
(g) screening the library of fusion proteins for improved activity as compared to a non-modified fusion protein, wherein improved activity as compared to the non-modified fusion protein is indicative of an improved fusion protein.

Improved activity of the fusion protein includes, without limitation, improved binding of the fusion protein to the target molecule and/or improved function of the effector molecule.

As mentioned previously, the effector function tested depends on the effector molecule used in the fusion protein. For effector molecules that induce cell growth, cell growth or proliferation assays may be used. For effector molecules that inhibit cell growth, cell growth assays may be used as previously described.

In a specific embodiment, the light chain variable region or the heavy chain variable region are randomly mutated in the method of the invention. In a preferred embodiment, the complementarity determining regions are randomly mutated in the method of the invention. In a more preferred embodiment, the hot-spots in the light chain and/or the heavy chain are randomly mutated in the method of the invention.

In one embodiment of the invention, the light chain variable region is mutated in the method of the invention.

Accordingly, the invention includes a method of making an improved immunotoxin, comprises the steps:
- (a) providing a nucleic acid sequence of a light chain variable region and a heavy chain region variable of an antibody or immunotoxin;
- (b) introducing at least one point mutation in the nucleic acid sequence encoding the light chain variable region to generate a library of nucleic acid sequences encoding variant light chain variable regions;
- (c) constructing a library of vectors, wherein each vector encodes an immunotoxin and comprises one of the variant light chain variable region nucleic acid sequences made in step (b) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;
(d) transforming host cells with the library of vectors to produce a library of recombinant cells;
(e) cloning the transformed host cells;
(f) expressing a library of immunotoxins, wherein the immunotoxin is a soluble protein expressed by the host cells; and
(g) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

In another embodiment, the method of making an improved immunotoxin, comprises the steps:

(a) providing a nucleic acid sequence of a light chain variable region and a heavy chain region variable of an antibody or immunotoxin;
(b) identifying the hot spots in the light chain variable region;
(c) introducing at least one point mutation in the nucleic acid sequence encoding the light chain variable region at the hot spots to generate a library of nucleic acid sequences encoding variant light chain variable regions;
(d) constructing a library of vectors, wherein each vector encodes an immunotoxin and comprises one of the variant light chain variable region nucleic acid sequences made in step (c) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;
(e) transforming host cells with the library of vectors to produce a library of recombinant cells;
(f) cloning the transformed host cells;
(g) expressing a library of immunotoxins, wherein the immunotoxin is a soluble protein expressed by the host cells; and
(h) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

In another embodiment of the invention, the heavy chain variable region is mutated in the method of the invention. Accordingly, in another embodiment, the method comprises the steps:

(a) providing a nucleic acid sequence of a light chain variable region and a heavy chain region variable of an antibody or immunotoxin;
(b) introducing at least one point mutation in the nucleic acid sequence encoding the heavy chain variable region to generate a library of nucleic acid sequences encoding variant heavy chain variable regions;
(c) constructing a library of vectors, wherein each vector encodes an immunotoxin and comprises one of the variant heavy chain variable region nucleic acid sequences made in step (b) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;
(d) transforming host cells with the library of vectors to produce a library of recombinant cells;
(e) cloning the transformed host cells;
(f) expressing a library of immunotoxins, wherein the immunotoxin is a soluble protein expressed by the host cells; and
(g) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

Another embodiment of the invention is a method comprising the steps:

(a) providing a nucleic acid sequence of a light chain variable region and a heavy chain region variable of an antibody or immunotoxin;
(b) identifying the hot spots in the heavy chain variable region;
(c) introducing at least one point mutation in the nucleic acid sequence encoding the heavy chain variable region at the hot spots to generate a library of nucleic acid sequences encoding variant heavy chain variable regions;
(d) constructing a library of vectors, wherein each vector encodes an immunotoxin and comprises one of the variant heavy chain variable region nucleic acid sequences made in step (c) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;
(e) transforming host cells with the library of vectors to produce a library of recombinant cells;
(f) cloning the transformed host cells;
(g) expressing a library of immunotoxins, wherein the immunotoxin is a soluble protein expressed by the host cells; and
(h) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin.

The invention also includes variations to the above methods, for example, the method can combine mutating both the heavy chain variable region and the light chain variable region. In one embodiment, the heavy chain variable regions and light chain variable regions can be mutated and screened sequentially. In another embodiment, the heavy chain variable regions and light chain variable regions can be mutated and screened at the same time.

Accordingly, another embodiment of the invention is a method of making an improved immunotoxin, comprising the steps:
(a) providing a nucleic acid sequence of a light chain variable region and a heavy chain region variable of an antibody or immunotoxin;
(b) introducing at least one point mutation in the nucleic acid sequence encoding the light chain variable region to generate a library of nucleic acid sequences encoding variant light chain variable regions;
(c) constructing a library of vectors, wherein each vector encodes an immunotoxin and comprises one of the variant light chain variable region nucleic acid sequences made in step (b) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;
(d) transforming host cells with the library of vectors to produce a library of recombinant cells;
(e) cloning the transformed host cells;
(f) expressing a library of immunotoxins, wherein the immunotoxin is a soluble protein expressed by the host cells;
(g) screening the library of immunotoxins for improved binding and/or cytotoxicity to a target cell as compared to the non-modified antibody or immunotoxin of step (a), wherein improved binding and/or cytotoxicity to the target cell as compared to the non-modified antibody or immunotoxin is indicative of an improved immunotoxin;
(h) introducing at least one point mutation in the nucleic acid sequence encoding the heavy chain variable region to generate a library of nucleic acid sequences encoding variant heavy chain variable regions;
(i) constructing a library of vectors, wherein each vector encodes an immunotoxin and comprises one of the variant heavy chain variable region nucleic acid sequences made in step (h) and/or the variant light chain variable region nucleic acid sequence of the improved immunotoxin identified in step (g), and wherein the variant heavy chain variable region nucleic acid sequence or the variant light chain variable region nucleic acid sequence is operatively linked to a nucleic acid sequence encoding a cytotoxin;
(j) transforming host cells with the library of vectors to produce a library of recombinant cells;
(k) cloning the transformed host cells;
(l) expressing a library of immunotoxins, wherein the immunotoxin is a soluble protein expressed by the host cells; and
(m) screening the library of immunotoxins for improved binding and/or improved cytotoxicity to a target cell as compared to the non-modified antibody or immunotoxin, wherein improved binding and/or improved cytotoxicity to the target cell as compared to the non-modified antibody or immunotoxin is indicative of an improved immunotoxin.

Further the invention includes a method of making an improved immunotoxin, comprising the steps:
(a) providing a nucleic acid sequence of a light chain variable region and a heavy chain region variable of an antibody or immunotoxin;
(b) introducing at least one point mutation in the nucleic acid sequence encoding the heavy chain variable region to generate a library of nucleic acid sequences encoding variant heavy chain variable regions;
(c) constructing a library of vectors, wherein each vector encodes an immunotoxin and comprises one of the variant heavy chain variable region nucleic acid sequences made in step (b) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;
(d) transforming host cells with the library of vectors to produce a library of recombinant cells;
(e) cloning the transformed host cells;
(f) expressing a library of immunotoxins, wherein the immunotoxin is a soluble protein expressed by the host cells;
(g) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin;
(h) introducing at least one point mutation in the nucleic acid sequence encoding the light chain variable region to generate a library of nucleic acid sequences encoding variant light chain variable regions;
(i) constructing a library of vectors, wherein each vector encodes an immunotoxin and comprises one of the variant light chain variable region nucleic acid sequences made in step (h) and/or the variant heavy chain variable region nucleic acid sequence of the improved immunotoxin identified in step (g), and wherein the variant light chain variable region nucleic acid sequence or the variant heavy chain variable region nucleic acid sequence is operatively linked to a nucleic acid sequence encoding a cytotoxin;
(j) transforming host cells with the library of vectors to produce a library of recombinant cells;
(k) cloning the transformed host cells;
(l) expressing a library of immunotoxins, wherein the immunotoxin is a soluble protein expressed by the host cells; and
(m) screening the library of immunotoxins for improved binding and/or improved cytotoxicity to a target cell as compared to the non-modified antibody or immunotoxin, wherein improved binding to the target cell and/or improved cytotoxicity to the target cell as compared to the non-modified antibody or immunotoxin is indicative of an improved immunotoxin.

Accordingly, another embodiment of the invention is a method of making an improved immunotoxin, comprising the steps:
(a) providing a nucleic acid sequence of a light chain variable region and a heavy chain region variable of an antibody or immunotoxin;

(b) identifying the hot spots in the light chain variable region;
(c) introducing at least one point mutation in the nucleic acid sequence encoding the light chain variable region at the hot spots to generate a library of nucleic acid sequences encoding variant light chain variable regions;
(d) constructing a library of vectors, wherein each vector encodes an immunotoxin and comprises one of the variant light chain variable region nucleic acid sequences made in step (c) and/or one heavy chain variable region nucleic acid sequence from step (a), and wherein the variant light chain variable region nucleic acid sequence or the heavy chain variable region nucleic acid sequence is operatively linked to a nucleic acid sequence encoding a cytotoxin;

(e) transforming host cells with the library of vectors to produce a library of recombinant cells;

(f) cloning the transformed host cells;

(g) expressing a library of immunotoxins, wherein the immunotoxin is a soluble protein expressed by the host cells;

(h) screening the library of immunotoxins for improved binding and/or cytotoxicity to a target cell as compared to the non-modified antibody or immunotoxin of step (a), wherein improved binding and/or cytotoxicity to the target cell as compared to the non-modified antibody or immunotoxin is indicative of an improved immunotoxin;

(i) identifying the hot spots in the heavy chain variable region;

(j) introducing at least one point mutation in the nucleic acid sequence encoding the heavy chain variable region at the hot spots to generate a library of nucleic acid sequences encoding variant heavy chain variable regions;

(k) constructing a library of vectors, wherein each vector encodes an immunotoxin and comprises one of the variant heavy chain variable region nucleic acid sequences made in step (j) and/or the variant light chain variable region nucleic acid sequence of the improved immunotoxin identified in step (h), and wherein the variant heavy chain variable region nucleic acid sequence or the variant light chain variable region nucleic acid sequence is operatively linked to a nucleic acid sequence encoding a cytotoxin;

(l) transforming host cells with the library of vectors to produce a library of recombinant cells;

(m) cloning the transformed host cells;

(n) expressing a library of immunotoxins, wherein the immunotoxin is a soluble protein expressed by the host cells; and (o) screening the library of immunotoxins for improved binding and/or improved cytotoxicity to a target cell as compared to the non-modified antibody or immunotoxin, wherein improved binding and/or improved cytotoxicity to the target cell as compared to the non-modified antibody or immunotoxin is indicative of an improved immunotoxin.

Further the invention includes a method of making an improved immunotoxin, comprising the steps:

(a) providing a nucleic acid sequence of a light chain variable region and a heavy chain region variable of an antibody or immunotoxin;

(b) identifying the hot spots in the heavy chain variable region;

(c) introducing at least one point mutation in the nucleic acid sequence encoding the heavy chain variable region at the hot spots to generate a library of nucleic acid sequences encoding variant heavy chain variable regions;

(d) constructing a library of vectors, wherein each vector encodes an immunotoxin and comprises one of the variant heavy chain variable region nucleic acid sequences made in step (c) and/or one light chain variable region nucleic acid sequence from step (a), and wherein the variant heavy chain variable region nucleic acid sequence or the light chain variable region nucleic acid sequence is operatively linked to a nucleic acid sequence encoding a cytotoxin;

(e) transforming host cells with the library of vectors to produce a library of recombinant cells;

(f) cloning the transformed host cells;

(g) expressing a library of immunotoxins, wherein the immunotoxin is a soluble protein expressed by the host cells;

(h) screening the library of immunotoxins for improved binding and/or improved cytotoxicity to a target cell as compared to the non-modified antibody or immunotoxin of step (a), wherein improved binding and/or improved cytotoxicity to the target cell as compared to the non-modified antibody or immunotoxin is indicative of an improved immunotoxin;

(i) identifying the hot spots in the light chain variable region;

(j) introducing at least one point mutation in the nucleic acid sequence encoding the light chain variable region at the hot spots to generate a library of nucleic acid sequences encoding variant light chain variable regions;

(k) constructing a library of vectors, wherein each vector encodes an immunotoxin and comprises one of the variant light chain variable region nucleic acid sequences made in step (j) and/or the variant heavy chain variable region nucleic acid sequence of the improved immunotoxin identified in step (h), and wherein the variant light chain variable region nucleic acid sequence or the variant heavy chain variable region nucleic acid sequence is operatively linked to a nucleic acid sequence encoding a cytotoxin;

(l) transforming host cells with the library of vectors to produce a library of recombinant cells;

(m) cloning the transformed host cells;

(n) expressing a library of immunotoxins, wherein the immunotoxin is a soluble protein expressed by the host cells; and (o) screening the library of immunotoxins for improved binding and/or improved cytotoxicity to a target cell as compared to the non-modified antibody or immunotoxin, wherein improved binding to the target cell and/or improved cytotoxicity to the target cell as compared to the non-modified antibody or immunotoxin is indicative of an improved immunotoxin.

In a preferred embodiment, the light chain variable region is mutated and screened before the heavy chain variable region is mutated and screened.

Because it is statistically unlikely that all possible combinations can be screened within one round of mutation, the invention contemplates multiple rounds of mutations and screening. In one embodiment, all positive clones from the first round of screening are pooled, followed by mutating the variable domains into a secondary library for screening, which is likely to be significantly smaller than the primary library. For example, a reshuffling step can be done to create the second library for screening, wherein variable domains are randomly combined from the positive clones to create the second library.

A number of steps in the methods of the invention can be automated and are compatible with high throughput capabilities. For example, the steps of cloning the transformed host cells, expressing the library of immunotoxins and screening the library of immunotoxins can be automated.

Once an improved fusion protein or immunotoxin is prepared, it may be modified to replace the effector molecule with another effector molecule. For example, in the case of immunotoxins the toxin can be replaced with another toxin as described in Example 4.

(D) Improved Fusion Proteins and Uses Thereof

The invention also includes the improved fusion proteins made using the methods of the invention. In particular, as described in Example 4, the inventors have prepared an improved immunotoxin using the affinity maturation method of the invention. The sequence of one affinity matured antibody is shown in FIG. 10 (SEQ ID NOS:1 and 2). Accordingly, in one embodiment, the immunotoxin comprises a light chain variable region shown in SEQ ID NO:2 and/or a heavy chain variable region shown in SEQ ID NO:1.

The invention includes the use of the improved fusion proteins to treat or diagnose a disease and methods of treating or diagnosing a disease using the improved fusion proteins of the invention.

In one embodiment, the invention provides a method of treating or preventing cancer, comprising administering to a subject having or suspected of having cancer an effective amount of the fusion protein of the invention. In another embodiment, the invention provides the use of an effective amount of the fusion protein of the invention for the manufacture of a medicament for treating or preventing cancer. Furthermore, the invention provides the use of an effective amount of the fusion protein of the invention, further comprising the use of an additional cancer therapeutic agent for the manufacture of a medicament for simultaneous, separate or sequential treatment or prevention of cancer. The invention also provides the use of an effective amount of the fusion protein of the invention for treating or preventing cancer. Further, the invention provides the use of an effective amount of the fusion protein of the invention, further comprising the use of an additional cancer therapeutic agent for simultaneous, separate or sequential treatment or prevention of cancer.

In one embodiment of the invention, cancer includes, without limitation, stomach cancer, colon cancer, prostate cancer as well as cervical cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, pancreatic cancer, endometrial cancer, plasmacytoma, lymphoma, and melanoma.

The fusion proteins of the invention may be formulated into pharmaceutical compositions for administration to subjects in a biologically compatible form suitable for administration in vivo. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the recombinant protein of the invention to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present invention provides a pharmaceutical composition for treating or preventing cancer comprising a fusion protein of the invention, and a pharmaceutically acceptable carrier, diluent or excipient. In a preferred embodiment, the effector molecule of the fusion protein in the pharmaceutical composition is a cancer therapeutic agent, more preferably a toxin.

The pharmaceutical preparation comprising the fusion protein of the invention may be administered systemically. The pharmaceutical preparation may be administered directly to the cancer site. Depending on the route of administration, the fusion protein may be coated in a material to protect the compound from the action of enzymes, acids and other natural conditions that may inactivate the compound.

In accordance with one aspect of the present invention, the fusion protein is delivered to the patient by direct administration. The invention contemplates the pharmaceutical composition being administered in at least an amount sufficient to achieve the endpoint, and if necessary, comprises a pharmaceutically acceptable carrier.

The invention also provides methods for reducing the risk of post-surgical complications comprising administering an effective amount of the fusion protein of the invention before, during, or after surgery to treat cancer.

The compositions described herein can be prepared by known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, $20^{th}$ ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Fusion protein may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In various embodiments of the invention, the pharmaceutical composition is directly administered systemically or directly to the area of the tumor(s).

The pharmaceutical compositions may be used in methods for treating animals, including mammals, preferably humans, with cancer. The dosage and type of fusion protein to be administered will depend on a variety of factors which may be readily monitored in human subjects. Such factors include the etiology and severity (grade and stage) of the cancer.

Clinical outcomes of cancer treatments using the fusion proteins of the invention are readily discernable by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the fusion protein and another cancer therapeutic may be determined by comparative studies with patients undergoing monotherapy.

Another embodiment of the invention is a kit for treating or preventing cancer comprising an effective amount of the fusion protein of the invention, and directions for the use thereof to treat the cancer.

The following non-limiting examples are illustrative of the present invention:

EXAMPLES

Example 1

Immune Library Construction and Screening

The library is constructed using a soluble expression system. The amplification of the $V_H$ and $V_L C_L$ fragments are done by RT-PCR, using lymph node tissue isolated from cancer patients. Samples from normal subjects or from subjects suffering from other medical conditions may be desirable, depending on what type of antibody or cell surface target is to be identified. When the library is to be obtained from plasma cells, lymph node tissue is a suitable source of B cells, because it is the site for maturation of B cells into plasma cells, which actively secrete antibody, following exposure to antigen. An RT-PCR amplification of mRNA from plasma cells generates cDNA encoding the variable regions of antibodies which were raised in response to the tumor.

The chosen recombinant layout for the library screening is a VB6-variant pseudomonas exotoxin A ($ETA_{(252-608)}$) format which is an antibody fragment in the Fab format, linked to a truncated pseudomonas exotoxin A cytotoxin additionally modified to include a KDEL endoplasmic reticulum retention sequence. The Fab is a stable entity with a high degree of functionality. ETA provides suitable sensitivity for the level of expression generally observed with constructs of this type, will allow selection of internalized clones, is compatible with cytotoxic or cell proliferation assay such as MTS and Annexin V and is also suitable for normal and tumor tissue microarray (TMA).

1. Removal of Naïve B Cells from Patient Samples, Prior to Amplification

The process of B cell differentiation and maturation includes several stages (Molecular Immunology, Second Edition. Edited by Hames B. D. and Glover D. M. IRL Press). The early phase occurs in the bone marrow, where pre-B cells mature into virgin B cells, which present on their surface a very large non-antigen induced, basically random, repertoire of surface Ig. These cells migrate to the spleen and lymph nodes, where they are exposed to antigen and relevant clones are expanded, maturing finally into plasma cells.

One approach to obtain a smaller library that may be more efficiently screened is to amplify mRNA originating from plasma cells. These are the cells involved in active production of antibody, resulting from clonal expansion of antigen challenged B cells. Amplification of mRNA from the naïve B cell population which presents a non-antigen induced population of antibody on their surface results in a very large library that takes longer to screen and will likely generate much more irrelevant clones. Although it may be desirable at times to screen such a "non-induced" library, removal of naïve B cells from the samples that are going to be used as templates for amplification will yield a higher proportion of antigen-induced clones.

Naïve B cells express on their surface IgD, which can be used as a marker (Fundamental Immunology, Fifth Edition, W. E. Paul, Lippincott Williams & Wilkins publishers, p 126). This marker is lost when cells mature into activated B cells, followed by maturation into plasma cells. Therefore, removal of naïve B cells can be done by using biotinylated anti-IgD monoclonal antibodies available commercially, followed by a capture step. The efficacy of this step will be assessed by flow cytometry, using an anti-IgD antibody conjugated to FITC.

2. Assessment of the Pool Size of Available Plasma Cells, in the Patient samples Prior to the actual amplification step of a plasma cell library, the size of the library that is expected to be generated, is estimated by quantifying the pool size of available plasma cells in the clinical sample used as template. This can be done, for example, by using flow cytometry, with cells labeled with anti-CD38, as the primary antibody. CD38 is a surface marker strongly expressed by plasma cells (Harada H. H., Kawano M. M., Huang N., Harada Y., Iwato K., Tanabe O., Tanaka H., Sakai A., Asaoku H. and Kuramato A. 1993 "Phenotypic Difference of Normal Plasma Cells from Mature Myeloma Cells" *Blood* 81:2658-2663). Clinical samples yielding a large plasma cell population are the most useful. A final library size of $\geq 10^6$ colony forming units is desirable, thus a similarly sized pool of plasma cells in the sample to be used as template is desired. It is also possible to pool samples together from several cancer patients in order to get the desired number of plasma cells. If samples are pooled from several cancer patients, this will also minimize the chance of screening a library which doesn't contain antibodies resulting from an immune response to the tumor.

3. Amplification of $V_H$ and $V_LC_L$ Fragments from Patient Sample, Followed by Cloning Amplification of each light chain (κ and λ) and heavy chain (γ) is done by using RT-PCR, using extracted mRNA from clinical samples as template, with specific primers containing restriction sites at their 5' and 3' ends. The resulting fragments are randomly cloned into the Xoma vector using the appropriate restriction enzymes. Library size is important. It is desirable that there are ≥$10^6$ CFU (Colony Forming Units) for standard library screening protocols. To achieve this goal, several steps are performed:

Ligation of Amplified Material into Vectors:

This step is usually the bottleneck in library creation (Directed Evolution, Library Creation, Methods and Protocols. *Methods in Molecular Biology*, vol. 231, edited by Frances H Arnold and George Georgiu, 2003, Humana Press). Thus, a high efficiency ligation is needed, and careful optimization is required. Several ratios of digested insert/vector are tested. The ligation reaction is incubated at optimal conditions for library generation (Arnold and Georgiu, 2003). Efficiency of ligation is evaluated semi-quantitatively by agarose gel electrophoresis and quantitatively by electroporating into *E. coli* and plate counting the transformed colonies.

Transformation of Ligated DNA into *E. coli*:

Electroporation is an efficient and fast method of transformation. Parameters such as waveform, voltage and resistance can be readily optimized. For this protocol, commercially available electrocompetent cells are used.

Ratio of Ligated DNA/Electrocompetent Cells, During Electroporation:

It is desirable to use the minimal amount of DNA for each transformation, while still being able to get a suitably sized library, performing a reasonable number of individual electroporations.

The ratio of ligated DNA/electrocompetent cells is optimized until a clear and unambiguous sequence can be obtained for each sequenced colony. Then, it is possible to estimate the degree of degeneracy of the final library, if any, by comparing the sequence of approximately 20 different clones. (This does not apply to the previously mentioned re-plated colonies, where degeneracy is expected).

At this stage, the efficiency of the process is evaluated and it is determined whether a representative and suitably large library has been created.

4. Screening the Library

Screening the library can be done efficiently by using an automated colony picker, followed by inoculation of colonies into liquid growth media, contained in microwells. Efficient handling of liquid phase is done by the automated liquid handler. At that stage, it is important to determine the amount of cells that can be plated on each plate without causing over-crowding. The number of plates needed for efficient plating of a given size of library is determined. T shaped disposable sterile loops is used for plating.

The expected screening rate is $10^4$ clones/day. Therefore, screening a full sized library of $10^6$ CFU is expected to take 4-5 months. During the screening process, VB6-845ETA (252-608) is used as a positive control and pING3302 vector without insert as a negative control.

An important feature of the library construction and screening method relies in the ability to achieve random pairing of amplified variable regions, following cloning into the chosen vector, the pING3302 XOMA vector in this case. This enables the creation of an extremely diverse library, because of the possible number of combinations. It is extremely unlikely that all possible combinations can be screened within one round. Therefore, the positive clones which will be selected after one round are not likely to be the best achievable combinations of $V_H$ and $V_L$ domains. A re-shuffling step can be done to create and select the best combination of amplified domains. This will be achieved by pooling together all positive clones resulting from the first round of screening, followed by amplification and random cloning of the variable domains into a secondary library, which is likely to be significantly smaller than the primary library. A clone is considered positive if it yields a higher signal than the negative control, which is the minimum threshold value. If a large number of positives are obtained, clones are ranked and the best will be picked.

Screening is done in several stages. First, the entire library is screened for by FMAT assay for effective induction of apoptosis in a cell line matched by the type of cancer of the library origin. Clones selected as positive by the first round of FMAT are screened again through a second FMAT assay. Clones that remain positive through two rounds of FMAT screening on a selected positive cell line are then screened by FMAT against a positive cell line and a negative cell line selected as based on an unrelated cancer indication. Each clone passing the third round is then screened by flow cytometry binding against tumor cells, followed by screening against normal cells. Potency of the selected clones is determined by MTS and then finally potent clones are screened on Tumor Tissue Microarray (TMA). Clones which are not found to be potent by MTS test but that show high cancer selectivity can still be retained for a different development path such as cancer diagnostics or cancer antigen discovery.

Example 2

Colon Immune Library Construction

An immune library suitable for high throughput screening using an *E. coli* soluble display has been constructed. This method is based on RT-PCR amplification of the variable region of antibodies, using an enriched population of plasma B cells derived from the lymph nodes of colon cancer patients. The cDNA of the variable domains of the gamma and kappa chains were cloned randomly into the Xoma pING3302 vector as a Fab-ETA$_{(252-608)}$ construct and transformed in *E. coli* cells. The generated library, 2·$10^5$ clones, was validated by PCR amplification of each chain in 100% of the tested clones. In addition, the sequencing showed all clones have unique CDR loops ensuring that the diversity of the immune response is represented. In addition, upon induction with L-arabinose, suitable expression level was detected in the supernatant of clones grown in 96 well plates. Fusion with truncated *Pseudomonas* exotoxin A will allow selection of internalized clones via the measurement of apoptosis and will be suitable for TMA screening methods.

1. Enrichment in Plasma B Cells from Lymph Nodes from Colon Cancer Patients

The plasma B cells produce antibodies specific to antigen and are therefore the population of interest for the creation of the immune library. The anti-IgD antibody which binds to the IgD cell surface marker was used to deplete the naïve B cells. Three frozen lymph nodes, removed from colon cancer patients, were used as a source of plasma B cells. Frozen cells of the lymph nodes conserved in DMSO were thawed rapidly in a water bath set at 37° C. and diluted in 47 mL of DMEM +10% FBS. After centrifugation at 2000 RPM for 3 minutes, cells were washed with 20 mL of DMEM +10% FBS and re-suspended in 1 mL of the same medium. Anti-IgD mAb (250 ng) (1) and anti-THY-1 mAb (50 ng) (2), both antibodies conjugated to biotin, were used to deplete naïve B cells and T cells, respectively. After a period of 1.5 hours on ice, cells were centrifuged and re-suspended in 1 mL of fresh DMEM +10% FBS. An equal volume of magnetic beads coated with streptavidin (pre-washed three times with 1 mL of PBS buffer) was added to the cells for 1 hour incubation on ice with occasional mixing (3). At the end of the incubation period, naïve B cells and T cells linked to the beads were separated magnetically and the supernatant containing an enriched population of plasma B cells was collected and kept on ice.

In a separate experiment, efficiency of the depletion was assessed by flow cytometry using the anti-IgD biotinylated antibody prior to and after depletion. As shown in FIG. 1A, two populations, IgD negative (M1, 66.34%) and IgD positive (M2, 33.75%) were identified prior to depletion. After depletion, the percentage of IgD negative population increased from 66.34% to 99.35%, indicating that no cells were labeled after depletion.

2. mRNA Extraction and cDNA Synthesis

The mRNA of the plasma B cells was extracted using Oligotex™ kit (5) from a pool of $2.6 \cdot 10^6$ cells with 50% viability. Briefly, cells were centrifuged at 2000 rpm for 3 minutes at 4° C. and re-suspended in 600 μL of the lysis buffer. Cell lysate was then incubated with 17.5 μL of pre-heated Oligotex™ particles for 10 minutes at room temperature. The Oligotex™ particles were then washed with washing buffer and bound mRNA eluted in 50 μL elution buffer.

First strand cDNA was synthesized using SuperScriptIII™ reverse transcriptase kit following the provided instructions. Briefly, 8 μL of extracted mRNA, 1 μL of random hexamers mix and 1 μL of dNTPs were incubated at 65° C. for 5 minutes. A cDNA synthesis mix containing the following components; 2 μL of ×10 RT buffer, 4 μL of $MgCl_2$, 2 μL of DTT, 1 μL of RNAse Out and 1 μL of SuperScriptIII enzyme was added to the RNA/primer mixture and incubated for 10 minutes at 25° C. The first strand cDNA was synthesized at 50° C. for a period of 50 minutes. The reaction was then stopped at 85° C. for 5 minutes, chilled on ice and centrifuged. Following RNAse H treatment at 37° C. for 20 minutes, the cDNA was stored at −20° C.

3. Library Construction

In order to create the Fab-$ETA_{(252-608)}$ colon immune library, the PelB-$V_H$ and $V_L$-$C_L(\kappa)$ fragments were engineered by PCR followed by fusion with PelB leader sequence by a sub-cloning step ($V_H$) and randomly inserted into the EcoRI-ApaI-CH-$ETA_{(252-608)}$-PelB-SfiI-XhoI/3302 plasmid using the EcoRI/ApaI and SfiI/XhoI restriction sites, respectively. In order to capture most of the immune response occurring in the lymph node, a mixture of 5' primers corresponding to the different sub-classes of kappa and gamma chains were used in the PCR reactions. The 3' primer for the gamma and kappa chain was designed to anneal into the constant domain and at the 3' end of the chain, respectively. The $V_H$ and $V_L$-$C_L(\kappa)$ fragments were amplified by PCR using the cDNA extracted from the plasma B cells. The restriction sites required for the cloning of the $V_L$-$C_L(\kappa)$ fragments were contained in the primers. The amplified NcoI-$V_H$-ApaI fragment was fused downstream to the EcoRI-$ETA_{(252-608)}$IB-NcoI domain contained within the sub-clone vector. By doing this, a PelB-$V_H$ fragment with EcoRI/ApaI ends suitable for cloning was generated. The PCR amplified NcoI-$V_H$-ApaI fragment could not be cloned directly into the Universal Cloning Vector, EcoRI-ApaI-CH-$ETA_{(252-608)}$-PelB-SfiI-XhoI/3302, as the NcoI site is duplicated within this vector. However, this site has been removed from the sub-clone vector. Both fragments, PelB-$V_H$ and $V_L$-$C_L(\kappa)$, were ligated via the EcoRI/ApaI and SfiI/XhoI restriction sites in the EcoRI-ApaI-CH-$ETA_{(252-608)}$-PelB-SfiI-XhoI/3302 DNA plasmid and the ligation reaction was transformed into 10B cells. The number of transformants for the ligation of the light and heavy chain was $2 \cdot 10^5$ for both. In contrast, the same ligation reaction performed without inserts had less than 10% transformants compared to the previous. The final plasmid population containing the heavy and kappa chain randomly cloned as a Fab-$ETA_{(252-608)}$ was transformed in JM109, with a yield of approx. $0.5 \cdot 10^5$ clones per each individual electroporation, using 2 μL of supercoiled DNA purified from 10B cells (29).

PCR Amplification of $V_H$ and $V_L$-$C_L\kappa$ Domains:

a. PelB-$V_H$ Fragment

The PelB-$V_H$ fragment was assembled by a two step approach which involved PCR amplification of the $V_H$ domain followed by fusion to PelB leader sequence, by a sub-cloning step:

```
Gamma primer mixture
   1. 5' V_H:  CCAGCCATGGCGCAGRTGCAGCTGGTGCARTCTGG      (SEQ ID NO: 3)

2. 5' V_H:  CCAGCCATGGCGSAGGTCCAGCTGGTRCAGTCTGG      (SEQ ID NO: 4)

3. 5' V_H:  CCAGCCATGGCGCAGRTCACCTTGAAGGAGTCTGG      (SEQ ID NO: 5)

4. 5' V_H:  CCAGCCATGGCGSAGGTGCAGCTGGTGGAGTCTGG      (SEQ ID NO: 6)

5. 5' V_H:  CCAGCCATGGCGGAGGTGCAGCTGGTGGAGWCYGG      (SEQ ID NO: 7)

6. 5' V_H:  CCAGCCATGGCGCAGGTGCAGCTACAGCAGTGGGG      (SEQ ID NO: 8)

7. 5' V_H:  CCAGCCATGGCGCAGSTGCAGCTGCAGGAGTCSGG      (SEQ ID NO: 9)

8. 5' V_H:  CCAGCCATGGCGCAGGARGTGCAGCTGGTGCAGTCTGG   (SEQ ID NO: 10)

9. 5' V_H:  CCAGCCATGGCGCAGCAGGTACAGCTGCAGCAGTCAGG   (SEQ ID NO: 11)

10. 3' C_H:  TGCCAGGGGGAAGACCGATGGGCCCTTGGTGCTAG      (SEQ ID NO: 12)
```

Note: In order to isolate as many varieties as possible using a single primer, mixed bases are used for certain consensus primers: R=A+G, D=A+T+G, Y=C+T, H=A+C+T, V=A+C+G, K=T+G, S=C+G, W=A+T.

NcoI and ApaI restriction sites are in bold. All PCR reactions included a 50 μL reaction volume containing:

| 10X PCR buffer | 5 μL |
|---|---|
| 2 mM dNTPs | 5 μL |
| Primer 5' | 20 pmol |
| Primer 3' | 20 pmol |
| Taq DNA Polymerase, EasyA | 2.5 U |
| DNA | 10 μL |

The cycling conditions for PCR were: 95° C. for 1 minute, 62° C. for 1 minute, and 72° C. for 1 minute, for a total of 25 cycles followed by a final extension of 10 minutes at 72° C. The concentration of primer mixes represents the sum of concentrations of each individual primer. Construction of the fragment involved the following steps:

Step 1

The PCR reaction involved a mixture of primers 1 to 9 and primer 10, using the synthesized cDNA (10 μL) as template. This yielded a mixture of 450 bp $V_H$ fragments flanked at the 5' end by the NcoI site and at the 3' end by the ApaI site.

Step 2

A sub-cloning step was necessary in order to fuse the PelB leader sequence with the previously obtained $V_H$ fragment. A sub-clone vector was engineered as follows: An EcoRI-XhoI fragment was excised from Universal Cloning Vector, EcoRI-ApaI-$C_H$-ETA$_{(252-608)}$-PelB-SfiI-XhoI/3302 and inserted into similarly digested pSV-73 auxiliary plasmid. A SalI-XhoI fragment containing an unwanted NcoI restriction site was excised, followed by self-ligation of the vector, as SalI and XhoI have compatible ends. Approximately 100 ng of gel purified $V_H$ fragment and 200 ng of sub-clone vector were digested with ApaI (1.5 μL) in a total volume of 20 μL at 25° C. for 2 hours. Temperature was then elevated to 37° C. and NcoI was added (1.5 μL) with a further incubation of 2 hours. All digestion products were gel purified. The digested gamma heavy chain, 50 ng, was ligated overnight with 100 ng of digested plasmid in the presence of 2000 units of T4 DNA ligase at 16° C. The ligation reaction mixture was then purified using Zymo Research™ Concentrator kit and eluted to a final volume of 16 μL. EasyShock™ 10B electrocompetent cells were electroporated with 2 μL of the purified ligation reaction and resuspended in 1 mL of SOC medium. The efficiency of the ligation was assessed by plating 1/10 and 1/100 dilutions of transformation mixture onto a LB agar plate supplemented with Ampicillin (100 μg/mL). The plasmid was extracted from 1 mL overnight cultures. The extracted plasmid (900 ng) was digested with 1.5 μL of EcoRI in a total volume of 20 μL at 37° C. for 2 hours, purified with Zymo Research™ Concentrator kit and further digested with 1.5 μL of ApaI, in a total volume of 20 μL at 25° C. for 2 hours.

b. Kappa Light Chain

A PCR reaction was performed using primers 1 to 6 for the forward reaction and primer 7 for the reverse reaction to construct and amplify $V_L$-$C_L$(κ) fragments using the cDNA (10 μL) as a template. The SfiI and XhoI restriction sites (bolded) were added to facilitate the cloning of $V_L$-$C_L$(κ) into the EcoRI-ApaI-$C_H$-ETA$_{(252-608)}$-PelB-SfiI-XhoI/3302 plasmid. The Kappa light chain was include with the VI region for ease of cloning.

```
1. 5'V_L:  TCGCGGCCCAACCGGCCATGGCGCACCATCATCACCATCACGAC   (SEQ ID NO: 13)
           ATCCAGWTGACCCAGTCTCC 2. 5'V_L:  TCGCGGCCCAACCGGCCATGGCGCACCATCATCACCATCACGAT   (SEQ ID NO: 14)
           GTTGTGATGACTCAGTCTCC 3. 5'V_L:  TCGCGGCCCAACCGGCCATGGCGCACCATCATCACCATCACGAA   (SEQ ID NO: 15)
           ATTGTGWTGACRCAGTCTCC 4. 5'V_L:  TCGCGGCCCAACCGGCCATGGCGCACCATCATCACCATCACGAT   (SEQ ID NO: 16)
           ATTGTGATGACCCACACTCC 5. 5'V_L:  TCGCGGCCCAACCGGCCATGGCGCACCATCATCACCATCACGAA   (SEQ ID NO: 17)
           ACGACACTCACGCAGTCTCC 6. 5'V_L:  TCGCGGCCCAACCGGCCATGGCGCACCATCATCACCATCACGAA   (SEQ ID NO: 18)
           ATTGTGCTGACTCAGTCTCC
```

Reverse (XhoI restriction site in bold):

```
7. 3'C_L:  GCACTCGAGCTACTAACACTCTCCCCTGTTGAAGCTCTTTGTGA   (SEQ ID NO:19)
           CGGG
```

The cycling conditions for the PCR were: 95° C. for 1 minute, 62° C. for 1 minute and 72° C. for 1 minute, for 25 cycles, followed by a final extension of 10 minutes at 72° C.

Electrophoresis on a 1% agarose gel was used to separate the amplified PelB-$V_H$ and kappa light chain PCR products. The bands of interest were excised, purified using the Zymo Research™ kit and eluted in 16 μL. 2 μL were cloned into the TOPO PCR 2.1 cloning vector and transformed in 10F *E. coli* cells. Plasmids of transformed *E. coli* were isolated and sequenced using the CEQ sequencer as part of the sequencing validation step described below.

Validation:

To ensure the quality of the library, three tests were performed; PCR screening after each ligation reaction, sequencing of randomly selected heavy and kappa chain independent clones prior to insertion into the expression vector and after library assembly and expression in 96 well plates.

Library Construction:

Kappa Light Chain Cloning

Once the diversity of the sequences was confirmed by sequencing, the kappa chain PCR reaction, approximately 100 ng, was cloned into the Universal Cloning Vector, EcoRI- ApaI-CH-ETA$_{(252-608)}$-PelB-SfiI-XhoI/3302, using the unique restriction enzymes SfiI and XhoI. The kappa chain PCR reaction and the EcoRI-ApaI-CH-ETA$_{(252-608)}$-PelB-SfiI-XhoI/3302 plasmid were incubated with XhoI (1.5 µL) at 37° C. for 2 hours in presence of BSA in a final volume of 50 µL, after which 1.5 µL of SfiI was added. After 2 hours incubation at 50° C., the digested kappa light chain and plasmid were loaded onto an agarose gel, purified using Zymo Research™ gel purification kit (7) and eluted in 16 µL.

The digested kappa light chain, 50 ng, was ligated overnight with 100 ng of digested plasmid in the presence of 2000 units of T4 DNA ligase at 16° C. The ligation reaction mixture was then purified using Zymo Research™ Concentrator kit (8) and eluted to a final volume of 16 µL. EasyShock™ 10B electrocompetent cells (9) were electroporated with 2 µL of the purified ligation reaction and resuspended in 1 mL of SOC medium. The efficiency of the ligation was assessed by plating 1/10 and 1/100 dilutions of transformation mixture onto a LB agar plate supplemented with tetracycline (15 µg/mL). In addition, 10 isolated colonies were screened by PCR for the presence of the kappa light chain insert using the primer mix described in section 4B. The remaining transformed cells were grown at 37° C. in 50 mL of 2×YT in presence of 15 µg/mL of tetracycline. After overnight incubation, the C$_H$-ETA$_{(252-608)}$-PelB-V$_L$-C$_L$(κ)/3302 plasmids from 1 mL overnight culture were extracted.

a. PelB-V$_H$ Cloning

The previously double-digested (EcoRI and ApaI) PelB-V$_H$ fragments, 100 ng, were ligated into the C$_H$-ETA$_{(252-608)}$-PelB-V$_L$-C$_L$(κ)/3302 vector pre-digested with the same enzymes as described previously. The purification of the ligation, the transformation and PCR screening were performed as described previously except the gamma primers were used.

b. JM109 Transformation

The cloned plasmid was purified by Zippy miniprep and electroporated into an electrocompetent JM109 strain, which has been found to be the highest expresser in preliminary experiments The size of the obtained library was assessed by counting colony number after plating 1/10 and 1/100 dilutions of transformation mixture onto LB agar plate with 15 µg/mL of tetracycline.

c. Sequencing of the Heavy and Kappa Chain of Independent Clones

The sequencing of independent clones containing the PelB-V$_H$ and kappa chain insert was performed to ascertain that minimal redundancy was present in the generated library. As shown in table 1 and 2, the CDR loops amino acid sequences of each chain were unique. As expected, variability in the length of the CDR3 region of the heavy chains was obtained with a minimum of 11 to a maximum of 19 residues. In addition, the subclasses of the kappa and heavy fragments are indicated.

d. Western Blot Analysis of Immune Library Clones

The expression level of 15 independent clones was assessed by Western Blot after induction in the conditions that will be used during the screening of the library. (FIG. 2) Wells of a 96 well plate containing 150 µL of 2×YT supplemented with 15 µg/mL of tetracycline were inoculated with a single transformed JM109 colony/well and incubated overnight at 37° C. with constant shaking. The overnight grown seed cultures, 20 µL, were added to wells containing 130 µL of TB and incubated at 37° C. for 7 to 8 hours. Then, the culture was induced with 17.5 µL of 2% L-Arabinose and incubated overnight at 25° C. After centrifugation at 5000 RPM for 30 minutes, 16 µL of supernatant from 15 different wells was loaded onto a SDS-PAGE acrylamide gel under non-reducing conditions and analyzed by Western blot using an anti-human kappa light chain antibody coupled to HRP to confirm the presence and size of the recombinant protein. Full length expression of the Fab-ETA(252-608) was detected for 3 clones and the level of expression was similar to the positive control VB6-845-Fab-ETA(252-608). For 2 additional clones a low level of expression could be observed (lanes 3 and 6 on the right side blot) In addition, truncated products were also detected and the pattern was similar to the positive control.

4. Screening of Colon Cancer Based Immunotoxin Library

Each individual clone is expanded and expressed through the addition of arabinose to the media in one well of a 96 well plate. The supernatant of each well is tested for the ability to induce apoptosis on a selected target cell line.

FMAT Assay:

The supernatant of each well, 10 µL, is added to SW-480 tumor cells (previously seeded in a 96 well plate) To provide quantitative data, a live/death assay is implemented using Annexin V and centriRed staining. The wild-type VB6-845-ETA(252-608) is used as positive control. The FMAT plates are incubated at 37 C for 24 hours. 20 µl of Annexin-Alexa-Fluor 647/Centri-Red™ solution is added to each well and the plates are incubated for 1 hour at room temperature in the dark. The plates are then read on the FMAT reader. Cells positive for apoptosis will bind the Annexin due. All cells will be stained with the Cetri-Red dye. % apoptosis is calculated as the ratio of the # of Annexin positive events divided by the number of Centri-Red positive events. A clone is considered positive if apoptosis exceeds 20% above that of the negative control supernatant from cells containing the empty expression vector (pING-3302).

All clones that are positive in the first screening run are then rescreened under the same conditions. Cells that are positive through the first two rounds then tested in a third round including both a positive (cancer-type matched) and negative (unrelated cancer type) cell line. Results of 3 stages of FMAT screening are shown in Table 3. Clones that pass all 3 stages of the FMAT assay are further purified and validated.

Purification of the FMAT Screening Positive Clones:

Cells expressing the selected positive clones are grown. A 100 mL starter culture of 2×YT+Tetracycline (25 mg/L), divided equally between two shake-flasks was inoculated with 1 mL of frozen cell stock in Glycerol 10% and grown overnight with shaking at 37° C. The following day, 6 L of TB media divided between 12 shake-flasks (0.5 L each) were inoculated with 60 mL of the starter culture (5 mL each) and grown with shaking at 37° C. until OD$_{600}$≈2.0. At this stage, protein expression was induced by addition of Arabinose to a final concentration of 0.2% followed by overnight incubation with shaking at 25° C. The next day cells were removed by centrifugation at 8000 RPM (Sorvall™) for 50 minutes at 4° C., followed by coarse filtration through a cartridge filter (Sartorius™). Supernatant was concentrated by diafiltration against NaPO$_4$ 20 mM pH-7.5 buffer, using a 30 KDa MWCO membrane, bringing volume down from 6 L to 0.5 L.

The next stage included purification with a Ni$^{+2}$ column (12 mL). First step included charging the column with NiCl$_2$ 0.1M (5×CV), followed by washing with H$_2$O (10×CV) and equilibration with 5×CV of NaPO$_4$ 20 mM, NaCl 150 mM pH-7.5 buffer. Diafiltrated material was loaded at 5 mL/min, followed by washing first with 10×CV of NaPO$_4$ 20 mM, NaCl 150 mM pH-7.5 buffer and then by 8×CV of NaPO$_4$ 20 mM, NaCl 150 mM, Imidazole 100 mM pH-7.5. Column was eluted with NaPO$_4$ 20 mM, NaCl 150 mM, Imidazole 250 mM pH-7.5 and 10×2 mL fractions were collected and OD$_{280\,nm}$ was measured to decide which fractions to select for next stage, which included a Q-Sepharose™ (3 mL) column. This column was equilibrated with NaPO$_4$ 20 mM, NaCl 90 mM pH-7.5 prior to loading the diluted protein containing fractions from previous step. Dilution was done in NaPO$_4$ 20 mM pH-7.5 to achieve conductivity similar to the equilibration buffer. Following loading of the sample, column was washed with 15×CV of the equilibration buffer and eluted with NaPO$_4$ 20 mM, NaCl 500 mM pH-7.5 buffer. Fractions were collected (10×2 mL) and stored at −20° C. overnight. The next day, the previous stage eluate was loaded onto an S-200 size-exclusion column, previously rinsed with NaPO$_4$ 20 mM, NaCl 150 mM pH-7. Fractions were collected (10 mL each) after passage of a 100 mL void volume. The purity and identity of the processed material were estimated by Coomassie and Western-Blot, as per SOP's 2.1.55 and 2.1.63, using α-Kappa HRP-conjugated antibody for detection. Finally, purified material was concentrated down to approximately 1 mL volume, using a spin-column and protein concentration was determined by the BCA assay.

Binding Affinity Measurement:

Flow cytometry is used to measure binding and determine the affinity of the selected positive clones for the positive screening cell line. (SW-480). To evaluate binding purified clone supernatants are incubated against a fixed number of SW-480 cells to establish a saturation curve. Binding is detected using the rabbit anti-ETA(252-608) and compared to positive controls VB6-845PE (high affinity) and VB6-011ETA(252-608) (moderate affinity). To determine affinity increased concentrations of the purified clone supernatants are incubated The binding affinity expressed as the dissociation constant, $K_D$ will be calculated by the Lineweaver-Burk method of plotting the inverse of the median fluorescence as function of the inverse of the antibody concentration. The dissociation constant is determined by the following equation: $1/F = 1/F_{Max} + (K_D/F_{Max})(1/[scFv])$, where F corresponds to the background subtracted median fluorescence and $F_{Max}$ is calculated from the plot. Results of the binding assessment on 4 of the 8 accepted clones is shown in table 4.

MTS Assay:

An MTS assay is used to determine the IC$_{50}$ values of the selected positive clones using the positive cell line, SW-480, and negative cell line CA-46 from an unrelated cancer type. The results of the MTS assay are summarized in Table 4.

Example 3

Library Construction for Affinity Maturation

In order to efficiently screen affinity matured antibodies created by either "hot spot modification" or by random mutagenesis, a Fab format of each candidate was linked to the cytotoxic protein *Pseudomonas* exotoxin A variant. The Fab-ETA(252-608) format (also referred to as the VB6-ETA(252-608) format herein) is suitable for evaluating binding activity and potency on tumor cells allowing for the rapid identification of the clones expressing high affinity antibodies. In addition, this format also permits the rapid screening against normal and tumor tissues by TMA profiling.

1. Library Construction

"Hot Spot Methodology":

a. Hot-Spot Identification

The somatic hypermutation that takes place in vivo targets specific sequences called "hot-pots" (Neuberger M. S and Milstein C. 1995. Somatic hypermutation. Curr. Opin. Immunol. 7:248-254). The hotspot sequences can be defined as consensus nucleotide sequences in certain codons. The consensus sequence is the tetranucleotide, RGYW, in which R can be either A or G, Y can be C or T and W can be either A or T (Neuberger M. S. et al., 1995). In addition, the serine residues encoded by the nucleotides AGY are predominantly present in the CDRs regions of the variable domain over those encoded by TCN corresponding to a potential hot-spot sequences (Wagner S. D., Milstein C. and Neuberger M. S. 1995. Codon bias targets mutation. Nature, 376, p 732). The structural analysis has shown that the CDR loops contribute the most to the antigen binding, especially the CDR3 loops (Giudicelli V., Chaume D. and Lefranc M. P. 2004. IMGT/V-QUEST, an integrated software program for immunoglobulin and T cell receptor V-J and V-D-J rearrangement analysis. Nucleic Acids Res. 32:435-440). Therefore, the nucleotide sequence of the CDRs of the heavy and light chains of each candidate is scanned for the presence of the hot-spot sequences and AGY codons. The identified hot-spots of the CDR regions of the light and heavy chain can be compared to the germinal sequences of the heavy and light chains using the International ImMunoGen Tics database (IMGT, http://imgt-.cines.fr/textes/vquest/) (Davies D. R., Padlan E. A. and Sheriff S. 1990. Antibody-antigen complexes. Annu. Rev. Biochem. 59:439-473). A sequence, identical to the germ line, will suggest that somatic mutation has not occurred; therefore the random mutations are introduced mimicking the somatic events occurring in vivo. In contrast, a different sequence shows that some somatic mutations have already occurred. It will remain to be determined if the in vivo somatic mutation was optimal. The hot-spots that code for buried or conserved amino acids within the CDRs won't be mutagenized. These residues are usually critical for the overall structure and are unlikely to interact with the antigen since they are buried. In addition, this analysis is compared to the predicted locations in the germ line sequences where somatic mutations occurred predominantly (Tomlinson I. M., Cox J. P. L., Gherardi E., Lesk A. M. and Chotia C. 1995. The structural repertoire of the human V$_λ$ domain. EMBO J. 14:4628-4638; Tomlinson I. M., Walter G., Jones P. T., Dear P. H., Sonnhammer E. L. L. and Winter G. 1996. The imprint of somatic hypermutation on the repertoire of human germline V genes. J. Mol. Biol. 256: 813-817). A similar strategy was applied for the affinity maturation of BL22 scFv. A point mutation introduced in the CDR3 of the heavy resulted in 5 to 10 fold increase in binding activity on various CD22-positive cell lines (Salvatore G., Beers R., Margulies I., Kreitman R. J. and Pastan I. 2002. Improved cytotoxic activity toward cell lines and fresh leukemia cells of a mutant anti-CD22 immunotoxin obtained by antibody phage display. Clinical Cancer Research, 8:995-1002). Also, the mutation of various amino acids in the CDR1 and CDR2 loops also produced mutant with increase affinity ranging from 3 fold to 7 fold (Ho M., Kreitman J., Onda M. and Pastan I. 2005. In vitro antibody evolution targeting germline hot spots to increase activity of an anti-CD22 immunotoxin. J. Biol. Chem., 280:607-617).

b. Introduction of Random Mutations at Selected Hot-Spots of the V$_L$ Region by PCR Once the hotspots are identified, oligonucleotides containing the degenerated codons (NNS, where N is A, G, C or T and S is G or C) are used to introduce all possible amino acids at the target positions, except the TAA and TGA stop codons. Previous studies suggest that the mutagenesis of the CDRs of the light chain followed by the CDRs of the heavy chain will lead to enhanced affinity compared to mutations isolated independently in both chains. Therefore, the affinity maturation of each candidate will start with the optimization the light chain. The identified hot-spots in the CDRs of the V$_L$ domain are randomly mutagenized by PCR. The generated PCR fragments contain unique restriction sites suitable for the direct cloning in the expression vector VB6-ETA(252-608)/3302. After the transformation of *E. coli* cells by electroporation and plating selection with the appropriate antibiotic, twenty colonies are grown and the isolated plasmids are sequenced. The analysis of the sequences is done to assess the diversity introduced at the targeted location.

2. Screening Process

Expression:

Wells of a 96 well plated containing 150 µl of 2×YT supplemented with 15 µg/ml of tetracycline were inoculated with a single transformed JM109 colony/well and incubated overnight at 37° C. with constant shaking. 20 µl of the overnight grown seed cultures were added to a 96 well plate containing 130 µl of TB and incubated at 37° C. for 7 to 8 hours. Then, the culture was induced with 17.5 µl of 2% L-arabinose and incubated overnight at 25° C. allowing the secretion of the Fab-ETA(252-608) in the supernatants. Mutants, identified by sequencing with PCR, are expressed in a soluble recombinant VB6-ETA(252-608) format and screened for increased binding/killing on tumor cells. Briefly, the screening starts with the inoculation of single colonies into a 96 well plate containing media with a colony picker. The plate is then incubated at 37° C. in a shaking incubator. When the $OD_{600}$ reaches 2, an aliquot of the culture of each well is taken out and frozen in presence of glycerol. Then, the bacteria is induced with the addition of the inducer and incubated overnight at 25° C. allowing the secretion of the Fab-ETA(252-608) in the supernatant.

Functional Screening Based on Tumor Cell Binding:

After centrifugation at 5000 RPM for 30 minutes, the supernatant of each well is added to live tumor cells (previously seeded in a 96 well plate) and the binding activity of the VB6-ETA(252-608) is detected with a rabbit antibody against the VB6-ETA(252-608) format, either anti-Fab or anti-ETA (252-608), followed by anti-rabbit-FITC. The 96 well plates are read in the FMAT™ plate reader. It is expected that the fluorescent detection, amplified by two polyclonal antibodies, will increase the sensitivity of the assay and be sufficient to detect the wild-type and consequently enhanced binders. Any clones expressing a VB6-ETA(252-608) variant with higher binding reactivity than the wild-type will be cherry-picked and the reactivity confirmed. It is expected that the data analysis from the plate reader will be quantitative so clones can be ranked based on the reactivity. The main advantage of the screening based on the phenotype is the rapidity of the assay.

Functional Screening Based on Live/Death Assay:

In addition, a live/death assay can be implemented using Annexin V or calcein staining. The VB6-ETA(252-608) supernatant is incubated with tumor cells seeded into a 96 well FMAT plate and the level of cytotoxicity is assessed over a period of 24 hours Once established, the potency of the mutagenized clones is measured and compared to the wild-type VB6-ETA(252-608). Given that the target is the same for each clones, it is generally assumed that an increase in the killing activity is correlated with an increase in affinity. Because of the incubation time required to measure the cytotoxicity effect, the live/death assay is slower than phenotyping of tumor cells.

ELISA Assay and Flow Cytometery

If the epitope or ligand (i.e. target molecule) that is recognized by the mutated fusion protein such as in the case of some affinity matured immunotoxins is known, the corresponding protein or peptide or compound is coated onto a 96 well plate and incubated with induced supernatant at room temperature for 2 hours. Supernatants from induced clones wild type (original antibody) and empty vector 3302 are used as positive and negative controls for epitope recognition. The binding of the affinity matured antibody to the epitope is then evaluated by ELISA. To confirm the reactivity of positive clones, the supernatants are then incubated with selected target tumor cells and the bound membrane associated immunotoxins are detected by flow cytometry.

Sequencing:

Once the reactivity of the top ten clones is confirmed, plasmid DNA will be extracted and sequenced. If the sequencing identifies a unique amino acid at the hot-spot positions, then the final construct will be engineered to contain this residue. However if multiple residues are obtained, then a combinatorial library will be constructed with the optimized residues at the different location and screened as previously described. Once the optimal clone has been selected, the specificity will be assessed by a competition assay against the wild-type VB6-ETA(252-608) and the parental antibody. It is expected the optimized CDR of the light chain Fab-ETA(252-608) protein will compete with both proteins.

It is feasible that the increased affinity obtained from a single point mutation may not be measurable by phenotyping or the live/death assay. Therefore, libraries with two or three mutagenized locations will be engineered. For example, the hot-spot regions of the CDR1 and CDR2 could possibly be combined.

3. Introduction of Random Mutations at Selected Hot-Spots in the $V_H$ Region by PCR The same strategy described earlier is used to create random mutations in the identified hot-spots of the CDRs of the $V_H$ region. The PCR fragment is then inserted to create the Fd-ETA(252-608) libraries using unique restriction sites. Once the optimal light chain is engineered, it will be cloned in the different Fd-ETA(252-608) libraries. After electroporation of *E. coli* cells with the ligation reaction and appropriate selection, single colonies are screened as described earlier. The clones with higher VB6-ETA(252-608) reactivity as compared to the optimized light chain clone are selected and ranked. Once the reactivity of the top five candidates is confirmed, plasmid DNA is extracted and sequenced. A final construct with the combined mutations in the CDRs of the heavy and light chains is then engineered and tested for biological activity. A competition assay between the affinity matured Fab and the parental antibody is performed to ensure that the initial binding specificity is conserved.

4. Further Biological Testing

The supernatant containing soluble affinity matured Fab-ETA(252-608), the wild-type Fab-ETA(252-608) and VB6-845-ETA(252-608) is added to antigen-positive tumor cells (used for the selection panning) and antigen-negative tumor cells. After 3 days incubation at 37° C., the $IC_{50}$ of soluble affinity matured Fab-ETA(252-608) is compared to the wild-type Fab-ETA(252-608) and VB6-845-ETA(252-608). Different scenarios are possible: A) If the $IC_{50}$ is within an acceptable range, <10 pM and at least two logs higher with the negative tumor cells, the clone will be grown. The purified product will be tested by TMA using the procedure established with Proxinium™ to ensure that selective binding is observed on tumor tissues compared to the normal critical tissues. If the clone passes TMA, the reactive Fab-ETA(252-608) will be further characterized for specificity and cross-reactivity against a panel our tumor cell banks containing 15 different indications using flow cytometry. B) If the $IC_{50}$ is higher than 10 pM and therefore not suitable for pre-clinical development, blocks of three to four amino acids in the CDR3 of the light and heavy chains will be randomly mutagenized except the amino acids which have a structural function and amino acids in the N-addition segment. In another approach, the $V_H$ and $V_L$ regions will be randomly mutagenized by error-prone PCR. Several articles have reported that the mutations introduced in the frame-work could result an increased affinity by the adjustment of the CDR loops therefore improving the interaction with the antigen (Daugherty P. S., Chen G., Iverson B. L. and Georgiou G. 2000. Quantitative analysis of the effect of the mutation frequency on the affinity maturation of single chain Fv antibodies. Proc Natl. Acad. Sci. U.S.A. 97:2029-2034). For instance the APEx display can be used. Biological testing will proceed as described for hot-spot mutagenesis and clones with suitable $IC_{50}$ values will be considered for further development as clinical candidates.

FIG. 3 depicts the affinity maturation process.

Example 4

Affinity Maturation of the VB6-011 Immunotoxin

1. Objective

Purified VB6-011, engineered as a Fab-de-bouganin fusion protein, competed with the parental antibody VB1-011 demonstrating that the specificity was preserved between the recombinant format and the parental antibody. However, the affinity of VB6-011, between $10^{-6}$ to $10^{-7}$ M, is 5 to 10 fold lower than VB1-011 resulting in an $IC_{50}$ of 350 nM. Thus, VB6-011 requires an affinity maturation step to make it suitable for further clinical development as efficacious therapeutics. This study protocol will describe the engineering of the VB6-011-PE, the introduction of point mutations in the CDR regions and the construction and screening procedure of the libraries.

2. Experimental Design

The recombinant format used for the affinity maturation of VB6-011 is the 011-Fab fragment linked to *Pseudomonas* exotoxin A variant with an added KDEL sequence. Previous studies have shown that upon induction of transformed *E. coli*, this format leads to the expression of soluble material in the supernatant. The soluble expressed Fab-ETA(252-608) protein is then used in a mix and read assay to assess tumor cell binding via the interaction of the Fab moiety to its cognate antigen, in a MTS assay by the measurement of the cytotoxicity activity and is suitable for TMA staining.

A dicistronic expression system comprising two units is generated. One unit comprises $PE\text{-}_{252\text{-}608}$ linked to the $V_H$-$C_H$ domain via a linker. The second unit comprises the $V_L$-$C_L$ domain with a histidine affinity tag placed at the N-terminal. The dicistronic unit is cloned into the pING3302 Xoma vector under the control of the arabinose-inducible araBAD promoter. The presence of the PelB leader sequence in both units results in secretion of the proteins into the periplasmic space where the non-reducing environment will allow the formation of a disulphide bridge between the two constant domains of the Fab. Ultimately, the VB6-011-ETA(252-608) fusion protein is secreted into the culture supernatant.

Engineering of VB6-011-ETA(252-608):

The engineering of VB6-011-ETA(252-608) is performed by the ligation of the PelB-$V_{H11}$ and $V_{L11}$-$C_{L_\kappa}$ fragments in the 3302 plasmid DNA containing the ApaI-CH-ETA(252-608)-PelB-SfiI-XhoI insert.

The VB6-011/3302 plasmid DNA is digested with the PvuII and NheI restriction enzymes and the $V_{H11}$ fragment is ligated into the PelB-NcoI-$V_{H08}$-$C_H$/pSV73 plasmid pre-digested with the same enzymes. The PelB sequence and the $C_H$ domain of the PelB-NcoI-$V_{H08}$-$C_H$/pSV73 contained a NcoI and ApaI restriction site, respectively creating the $V_H$ cassette. 10F competent cells are transformed with the ligation reaction and plated onto LB-agar plates supplemented with ampicillin. A clone with the PelB-$V_{H11}$-$C_H$ fragment is digested with EcoRI and ApaI and ligated into the $C_H$-ETA (252-608)-PelB-SfiI-XhoI/3302 plasmid DNA digested with the corresponding enzymes.

Similarly, the VB6-011/3302 plasmid DNA is digested with the EcoRV and XhoI restriction enzymes and the $V_{L11}$-$C_{L_\kappa}$ fragment is ligated in the PelB-SfiI-$V_{L845}$-$C_{L_\kappa}$/pSV73 plasmid pre-digested with the same enzymes. The PelB sequence is modified to contain a unique SfiI restriction site creating the light chain cassette. After transformation of 10F competent cells with the ligation reaction, the cells are selected on LB-agar supplemented with ampicillin. A clone with the PelB-SfiI-$V_{L11}$-$C_{Lk}$ fragment is digested with SfiI and XhoI and ligated into plasmid PelB-$V_{H11}$-$C_H$-ETA(252-608)-PelB-SfiI-XhoI/3302 digested with the corresponding enzymes. A plasmid containing the VB6-011-ETA(252-608) insert is then used to transform E104 and JM109 cells.

Small-Scale Expression Studies:

The transformed E104 and JM109 cells containing VB6-011-ETA(252-608) are propagated in 30 mL of TB medium (1% inoculums) in a 250 mL shake flask at 37° C., shaken at 225 rpm for approximately 5 hours until the optical density (O.D. 600 nm) reaches 2. At this time, the culture is induced with a final concentration of 0.1% L-(+) arabinose for 16 hours and incubated at 25° C. Subsequently, the supernatant is collected by centrifugation at 14000 rpm for 5 minutes and analyzed by Western blot using an anti-human kappa light chain (Sigma A-7164) under reducing and non-reducing conditions to confirm the presence and size of the immunotoxin.

If Western blot analysis of the VB6-011-ETA(252-608) demonstrates that intact Fab-ETA(252-608) is expressed at a suitable level, a similar experiment is performed in 200 uL of TB in 96 well plate inoculated with a single transformed E104 and JM109 colony. A similar expression level of VB6-011-ETA(252-608) in a 96 well plate compared to the shake flask will indicated that the libraries can be screened using the 96 well supernatant.

Biological Activity of the VB6-011-ETA(252-608):

Flow cytometry is used to assess the binding specificity of VB6-011-ETA(252-608) contained in the supernatant using antigen-positive cell lines, A-375 and Saos-2, and an antigen-negative cell line, Panc-1. Binding is detected using a rabbit anti-ETA(252-608) (1/100). In addition, an MTS assay is used to determine if the cytotoxicity of VB6-011-ETA(252-608) contained in the supernatant is able to be measured using the antigen positive cell lines A-375 and Saos-2 and antigen negative cell line Panc-1.

Affinity Maturation of VB6-011-ETA(252-608):

The analysis of the $V_H$ and $V_L$ sequences of the germ-line and VB1-011 revealed that 13 codons in the CDR loops of the light chain and 7 in the CDR loops of the heavy chains contains the hot-spots or AGY sequences. Therefore, 5 and 3 libraries are constructed to cover the light and heavy chain, respectively.

a. Introduction of Targeted Point Mutations by Saturation Mutagenesis in the Light Chain The PCR fragment containing the randomized nucleotides at the targeted location is generated by PCR. Primers 1 and 4 are common to all libraries and primers 2 and 3 are specific for each library. Restriction sites, SfiI and XhoI present in the PCR fragments is used to create the VB6-011-ETA(252-608) libraries.

The point mutation in the CDR loops is introduced by the Splice Overlapping Extension Polymerase Chain Reaction method (Weissensteiner et al. (2004): PCR technology, Current Innovations. CRC Press, Boca Raton, Fla. 33431, USA; Horton, R. M. and Tait, R. C. (1998): Genetic Engineering with PCR. Horizon Scientific Press, Wymondham, Norfolk, England) using the PelB-SfiI-$V_{L11}$-$C_{L_\kappa}$ as a template and the following primers:

```
1) 5' Primer 1
5' PelB:     GAA TTC CTG CAG GTC TAT GGA ACG ATA AAT          (SEQ ID NO: 20)

2) 3' Primer 2
5' CDR1-L1:  GTA GCT GCT ACT AAC SNN CTB SNN GGC CCT GCA GGA  (SEQ ID NO: 21)

5' CDR1-L2:  GTA CCA GGC TAA GTA SNN SNN SNN AAC ACT CTG ACT  (SEQ ID NO: 22)

5' CDR2-L1:  CAT GCC AGT GGC CCT SNN GGA TGC ACC ATA          (SEQ ID NO: 23)

5' CDR3-L1:  CTG AGG TGA GCT ACC SNN SNN SNN ACA GTA ATA CAC  (SEQ ID NO: 24)

5' CDR3-L2:  AGG TGT CTG AGG TGN SNN SNN ATA CTG CTG ACA      (SEQ ID NO: 25)

3) 5' Primer 3
5' CDR1-L1:  CTC TCC TGC AGG GCC NNS VAG NNS GTT AGT AGC AGC  (SEQ ID NO: 26)

5' CDR1-L2:  GCC AGT CAG AGT GTT NNS NNS NNS TAC TTA GCC TGG  (SEQ ID NO: 27)

5' CDR2-L1:  ATC TAT GGT GCA TCC NNS AGG GCC ACT GGC          (SEQ ID NO: 28)

5' CDR3-L1:  GCA GTG TAT TAC TGT NNS NNS NNS GGT AGC TCA CCT  (SEQ ID NO: 29)

5' CDR3-L2:  TAC TGT CAG CAG TAT NNS NNS NCA CCT CAG ACA      (SEQ ID NO: 30)

4) 3' Kappa-XhoI
5' CTC GAG TCA CTA ACA CTC TCC CCT GTT GAA GCT CTT           (SEQ ID NO: 31)
```

A two-step Splice Overlapping Extension PCR approach is undertaken using all the primers listed above to amplify the corresponding libraries, i.e., library 1 and 2 of the CDR1 loop, library 1 of the CDR2 loop and library 1 and 2 of the CDR3 loop (Weissensteiner et al, 2004; Horton and Tait, 1998). Restriction sites are underlined. N corresponds to the randomized nucleotides A, G, C, T; B to T, C, G; V to A, C, G and S to G, C.

The PCR reaction includes a 50 μL reaction volume containing:

| | |
|---|---|
| 10X PCR buffer | 5 μL |
| 2 mM dNTPs | 5 μL |
| 50 mM MgCl$_2$ | 2 μL |
| Primer 5' | 20 pmol |
| Primer 3' | 20 pmol |
| Taq DNA Polymerase | 2.5 U |
| DNA template | 50 ng |

The cycling conditions for PCR are: 94° C. for 1 min., 62° C. for 1 min., and 72° C. for 0.5 min., for a total of 20 cycles followed by a final extension of 10 min. at 72° C.

Step 1

Primers 1 and 2 are used to amplify the 5' library PCR fragment containing in the 5' end the PelB region in the 3' end the CDR loop with the targeted randomized nucleotides. In a second PCR reaction, primers 3 and 4 are used to amplify the 3' library PCR fragment containing in the 5' end the CDR loop with the targeted randomized nucleotides and in the 3' end two stop codons and the XhoI restriction site.

Step 2

In the second PCR reaction, primers 1 and 4 are used with 1 μl from each PCR product to produce PCR fragment containing the randomized nucleotides at the specific location in the corresponding CDR loop (818 bp).

The band is purified using the DNA clean and concentrator kit and digested with SfiI and XhoI restriction enzymes. The digested band is purified and inserted into the PelB-$V_{H11}$-$C_H$-ETA$_{(252-608)}$-PelB-SfiI-XhoI/3302 vector pre-digested with the same enzymes. Different ratios of vector/insert are tested such as 1:3 and 1:2 and the ligation reaction is performed in final volume of 20 μL in presence of high concentration of T4 DNA ligase and incubated at 16° C. for 12 hours. The JM109 electro-competent cells are then transformed with the ligation reaction and plated onto LB-agar plates supplemented with tetracycline. The number of colonies obtained after the transformation will determine the optimal conditions for the ligation reaction.

Screening of the Libraries:

a. Growth and Induction

Wells of a 96 well plate containing 150 μl of 2×YT supplemented with 15 μg/ml of tertracycline were inoculated with a single transformed JM109 colony/well and incubated overnight at 37° C. with constant shaking. 20 μl of the seed cultures were added to a 96 well plate containing 130 μl of TB and incubated at 37° C. for 7 to 8 hours. Cultures were then induced overnight with 17.5 μl of L-arabinose allowing the secretion of the VB6-011-ETA$_{(252-608)}$ into the supernatant.

Figure 4:
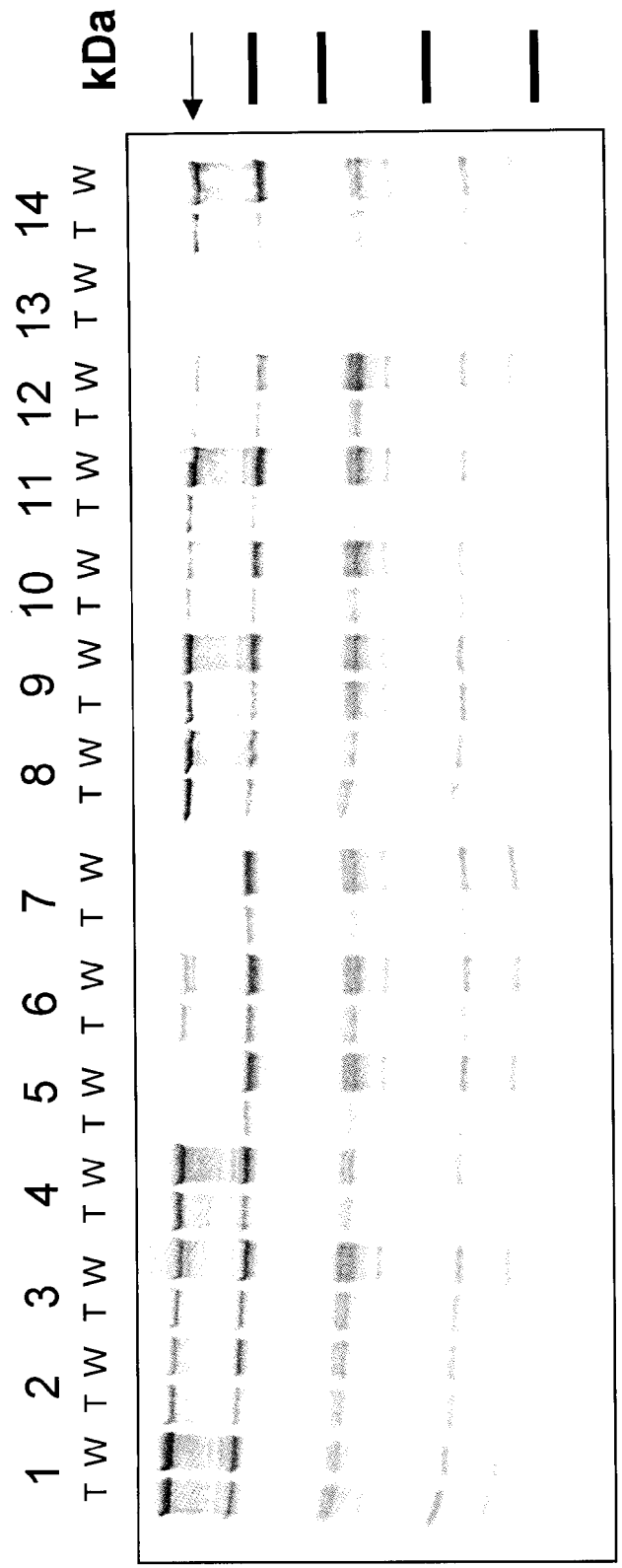
FIG. 4 is a Western blot of VB6-011-ETA$_{(252-608)}$ CDR-3 light chain clones. Supernatant (16 µL) of 13 clones generated in 96 well plates (W) or in 5 mL tubes (T) containing 150 µl and 1 ml, respectively were loaded under non-reducing conditions onto a SDS-PAGE gel and immunoblotted with Rabbit anti-*Pseudomonas* Exotoxin A antibody followed by goat anti-rabbit HRP antibody. Clone 13 is the VB6-011-ETA$_{(252-608)}$ wild-type grown and induced in a 5 ml tube or 96 well plate. The arrow indicates the full length protein at the expected size. The Western blot analysis showed that 10 clones out of 13 expressed a full length protein. The expressions levels in tube or well are similar and comparable to the wild-type.

FIG. 4 shows the results of a Western blot of VB6-011-ETA$_{(252-608)}$ light chain clones.

b. Functional Screening Based on the Phenotypic of Tumor Cells

A titration binding curve of the wild-type VB6-011-ETA$_{(252-608)}$ is used to determine the incubation time at room temperature to obtain an optimal signal with the FMAT™. The supernatant of each well, 10 μL, is added to Saos-2 tumor cells (previously seeded in a 96 well plate) and the binding activity of the VB6-011-ETA$_{(252-608)}$ mutated clones is detected with a goat anti-human IgG (H+L) antibody coupled to AlexaFluor 647 (1/250). In addition, in each experiment, the wild-type VB6-011-ETA$_{(252-608)}$ is used as a positive control. Any clones expressing a VB6-011-ETA$_{(252-608)}$ variant with higher binding reactivity than the wild-type is cherry-picked and the reactivity confirmed.

Figure 5A:
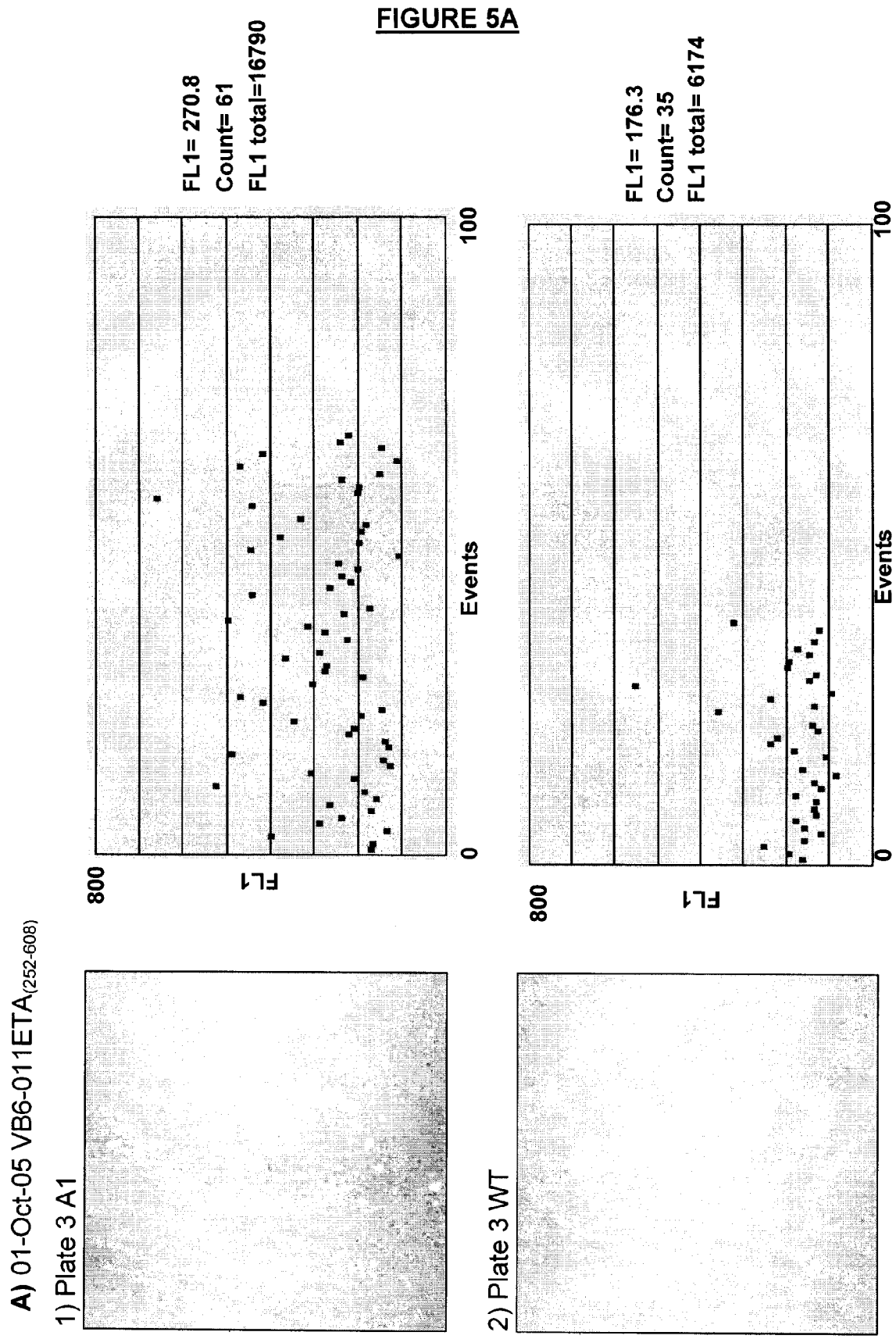
FIG. 5 is an FMAT screening. A) VB6-011-ETA$_{(252-608)}$. The supernatant, 5 µl, from induced clones and wild-type, was added to a FMAT plate containing A-375 cells seeded at 15000 per well the previous day. After 6 hours incubation at room temperature, the binding of the VB6-011-ETA$_{(252-608)}$ was detected with a goat anti-human heavy plus light chain antibody coupled with the Alexa Fluor 647®. The images of a well, plate 3 A1, identified as positive by the FMAT system technology as well as the wild-type (WT) showed distinct membrane staining. The scatterplot of the images, where the Y axis is the average fluorescence (FL-1) and X axis number of events, showed an increase in the average fluorescence and number of events for clone A1 of plate 3 compared to the wild-type. Total fluorescence is calculated by multiplying the average fluorescence by the number of events. B) VB6-008-ETA$_{(252-608)}$. Another Fab-PE fragment was tested with the FMAT system. The supernatant, 10 µl, of induced clones and wild-type was added to a FMAT plate containing MB435S cells seeded at 15000 per well the previous day. After 6 hours incubation at room temperature, the binding of the VB6-008 was detected with a mixture containing the rabbit anti- Pseudomonas exotoxin A antibody and the goat anti-rabbit antibody coupled with the Alexa Fluor 647®. The analysis of plate reveals that the clone from well F4 plate 1 demonstrated an increased average fluorescence and number of events.
Figure 5B:
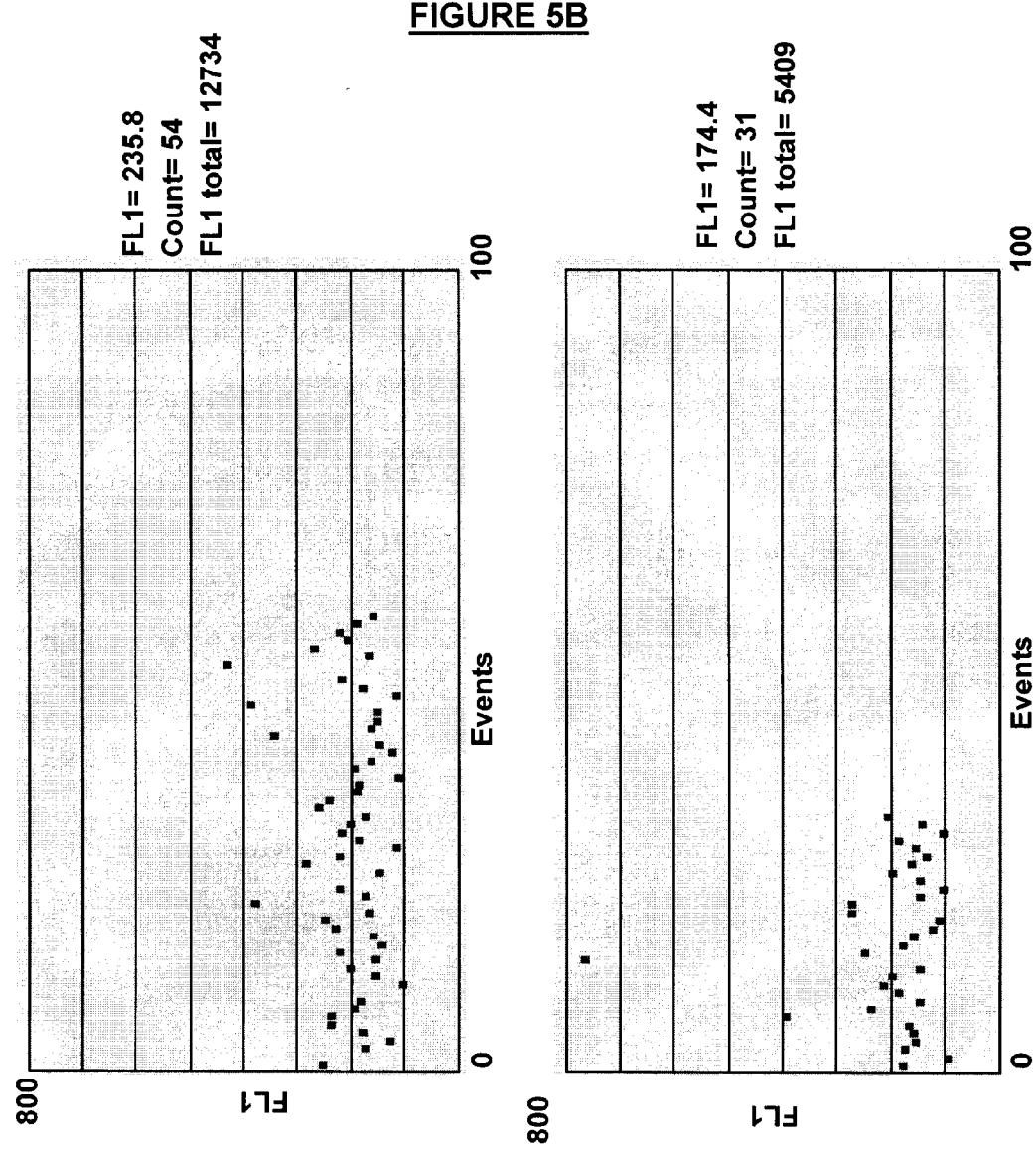

FIG. 5 shows the results of an FMAT screening.

c. Functional Screening Based on Live/Death Assay

However, if the data is not quantitative, a live/death assay is implemented using Annexin V and centriRed staining. The wild-type VB6-011-ETA$_{(252-608)}$ supernatant will be incubated with tumor cells and the level of cytotoxicity will be assessed over a period of 24 hours and compared to the wild type (original sequence) VB6-011-ETA$_{(252-608)}$. Once established, the potency of the mutagenized clones is measured and compared to the wild-type VB6-011-ETA$_{(252-608)}$. Given that the target is the same for each clone, it is generally assumed that an increase in the killing activity will be correlated with an increase in affinity.

Figure 6:
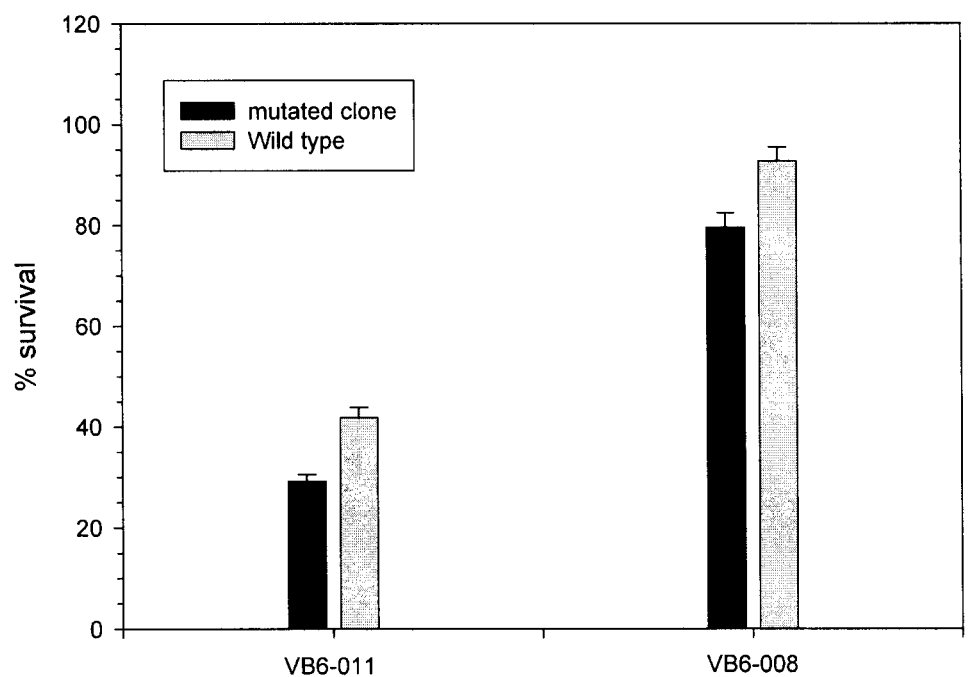
FIG. 6 is an MTS assay of clones selected by FMAT assay. A 96 well MTS plate was seeded with 5000 cells/well in a 50 µl volume of medium. A-375 cells and MB-435S cells were used to test VB6-011-ETA$_{(252-608)}$ and VB6-008-ETA$_{(252-608)}$, respectively. After adhering for 2 hours at 37° C. and 5% $CO_2$, 10 µl of *E. coli* supernatant was added to the wells along with 40 µl of medium to bring the final volume to 100 µl/well. Cells were incubated with supernatant at 37° C. and 5% $CO_2$ for 72 hours. After incubation, 20 µl of MTS reagent (1:20 MTS solution to PMS solution) was added to each well and allowed to develop at 37° C. and 5% $CO_2$ for another 2 hours. OD values were then read at 490 nm to determine the percentage of live cells.
Figure 7:
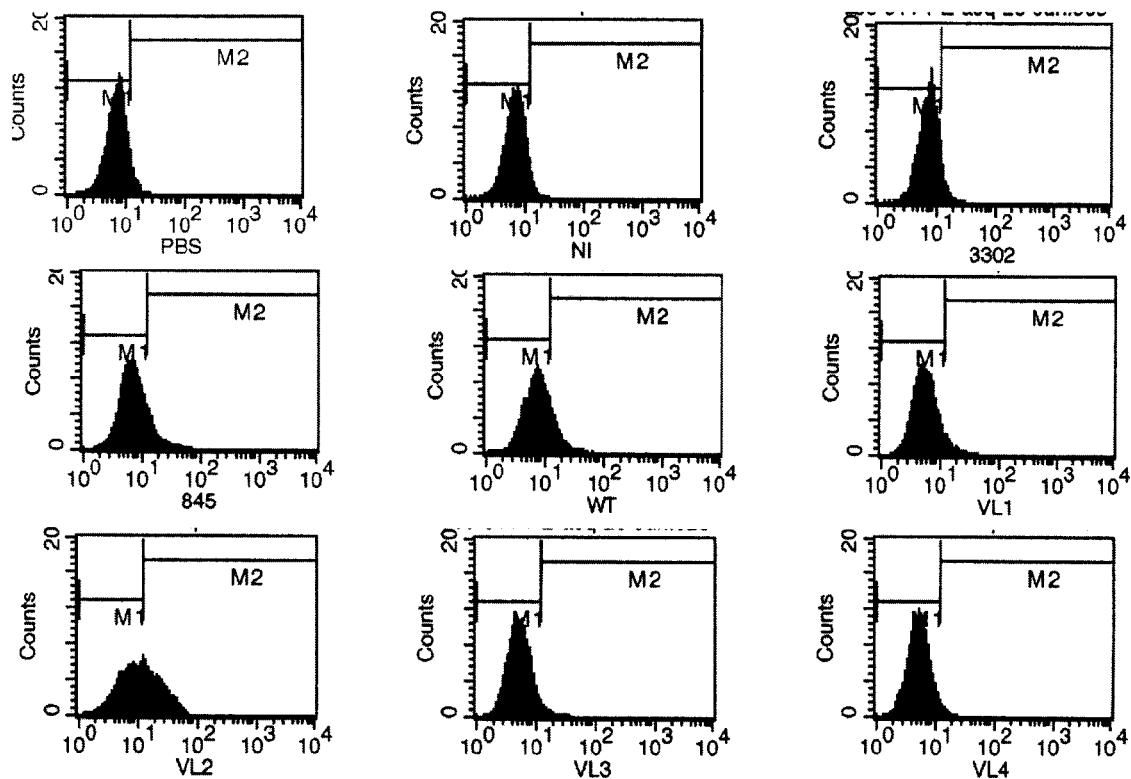
FIG. 7 is flow cytometry analysis of binding of affinity matured VL clones of VB6-011-ETA$_{(252-608)}$ on A-375 cells. N1=supernatant from non-induced *E-coli*, 3302=*E coli* transformed with pING3302, 845=VB6-845-ETA$_{(252-608)}$ negative control, WT=original VB6-011-ETA$_{(252-608)}$, VL-1 to VL-4 VB6-011-ETA$_{(252-608)}$ with affinity matured light chains.
Figure 9:
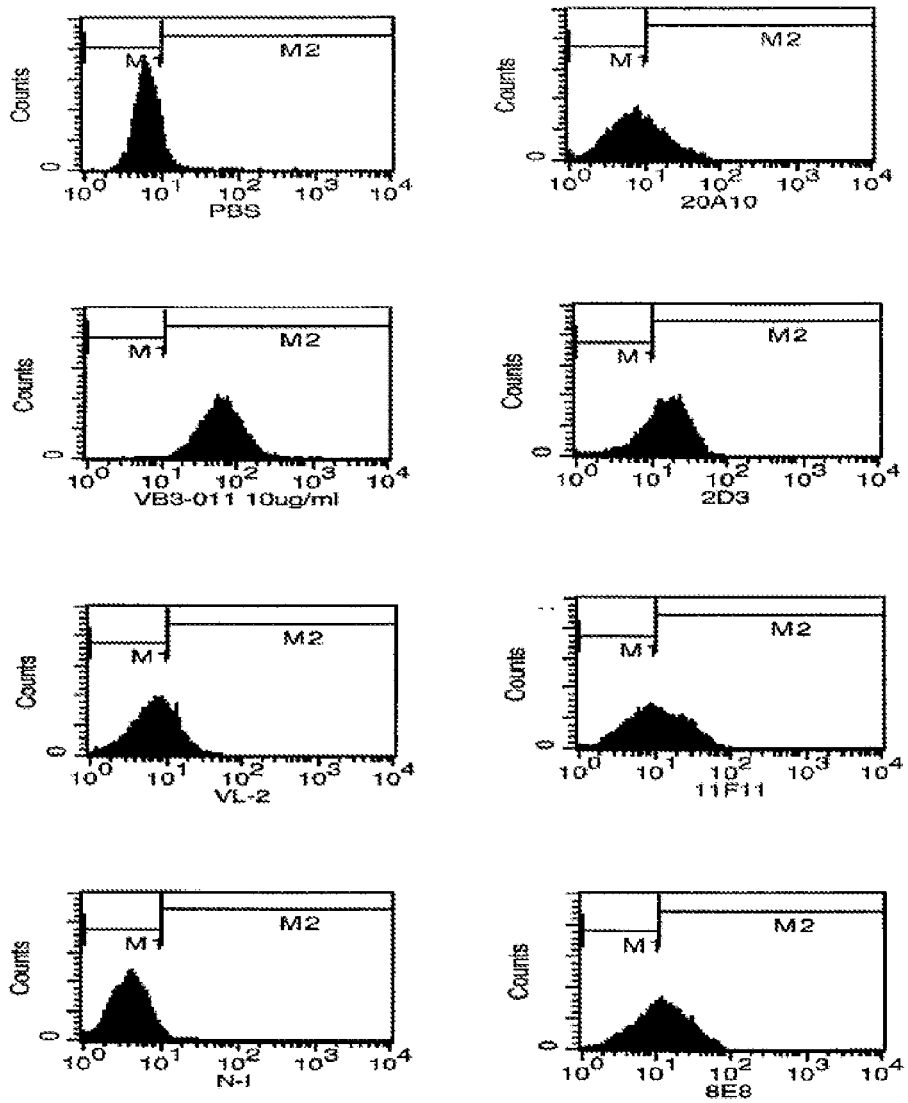
FIG. 9 is Flow cytometry of affinity matured combined light and heavy chains clones for VB6-011. PBS negative control, VB3-011 wild type parent antibody, VL-2 VB6-011-ETA$_{(252-608)}$ wild type heavy chain with affinity matured light chain, N-1 supernatant from uninduced VL-2 clone, induced supernatant 20A10, 2D3, 11F11 and 8E8 various clones with affinity matured light (VL-2) and individual heavy chains.

FIG. 6 shows the results of an MTS assay.

d. Sequencing and Reactivity

Once the reactivity of the top ten clones is confirmed, their plasmid DNA will be extracted and sequenced. If the sequencing identifies a unique amino acid at the hot-spot position, then the final construct will be engineered to contain this residue. However if multiple residues are obtained, then a combinatorial library is constructed with the optimized residues at the different locations and screened as previously described. Modified light chain motifs obtained from affinity purification of the light chain of VB6-$011ETA_{(252-608)}$ are listed in Table 5. The binding of the VB6-011 is measured by flow cytometry as described previously. The optimal clone is determined by a higher mean fluorescence than either the wild type or competing clones as shown in FIG. 7 and verified by ELISA binding against the antigen. In the case of VB6-011 this is an ELISA against immobilized chondriotin sulfate as shown in FIG. 8.

Once the optimal clone has been selected, the specificity is assessed by a competition assay with the VB1-011 antibody. Briefly, increased concentrations of VB1-011 is incubated against a fixed number of Saos-2 cells pre-incubated with the wild-type or mutagenized VB6-011-$ETA_{(252-608)}$ supernatant.

The optimized light chain is then combined with the library of targeted mutations in the heavy chain.

Introduction of Targeted Point Mutations by Saturation Mutagenesis in the Heavy Chain:

The PCR fragment containing the randomized nucleotides at the targeted location will be generated by PCR. Primer 1 and 4 is common to all libraries and primers 2 and 3 is specific for each library. Restriction sites, EcoRI and ApaI present in the PCR fragments is used to create the VB6-011-$ETA_{(252-608)}$ libraries.

The point mutation in the CDR loops is introduced by the Splice Overlapping Extension Polymerase Chain Reaction method (Weissensteiner, 2004; Horton and Tait, 1998) using the PelB-$V_{H11}$ as a template and the following primers:

A two-step Splice Overlapping Extension PCR approach is undertaken using all the primers listed above to amplify the corresponding libraries, i.e., one library for each CDR loop (Griffin and Griffin, 1994; Horton and Tait, 1998). Restriction sites are underlined. N corresponds to the randomized nucleotides A, G, C, T and S to G, C.

Step 1

Primers 1 and 2 are used to amplify the 5' library PCR fragment containing in the 5' end the PelB region in the 3' end the CDR loop with the targeted randomized nucleotides. In a second PCR reaction, primers 3 and 4 are used to amplify the 3' library PCR fragment containing in the 5' end the CDR loop with the targeted randomized nucleotides and in the 3' end two stop codons and the ApaI restriction site.

Step 2

In the second PCR reaction, primers 1 and 4 are used with 1 μl from each PCR product to produce PCR fragment containing the randomized nucleotides at the specific location in the corresponding CDR loops (527 bp).

The bands of interest is purified as described previously and digested with EcoRI and ApaI restriction enzymes. The digested band is purified and inserted into the PelB-$C_H$-$ETA_{(252-608)}$-PelB-SfiI-$V_{L11}$-$C_{L_\kappa}$/3302 vector pre-digested with the same enzymes and containing the optimal light chain. JM109 electro-competent cells are transformed with the ligation reaction and plated onto LB-agar plates supplemented with tetracycline.

The library is then screened by FMAT against positive cell line MDA-MB-345S. Clones are selected as positive if % apoptosis obtained is greater than the wild-type (original sequence) VB6-011-$ETA_{(252-608)}$ containing the optimized VL-2 light chain and sequenced. If more than one optimized motif is found a combinatorial library is constructed and the FMAT screening repeated. Some of the CDR motifs for the heavy chain of VB6-$011ETA_{(252-608)}$ are listed in Table 6. 43 clones were selected as positive from the VB6-$011ETA_{(252-608)}$ VL-2 heavy chain combinatorial library by FMAT screening. 25 of these very verified to maintain antigen specificity by CSA ELISA. 12 were verified as positive by flow cytometry. The optimal clone was selected as the one with highest MF binding by flow cytometry. (FIG. 9) Table 7 summarizes the results of the top 4 affinity matured constructs for VB6-$011ETA_{(252-608)}$. A final construct is engineered with both optimal heavy and light chain, in this case the clone

```
1) 5' Primer 1
5' PelB: GAA TTC CTG CAG GTC TAT GGA ACG ATA AAT                (SEQ ID NO: 32)

2) 3' Primer 2
5' CDR1-H1: GAC CCA GTG CAT AGC AAA SNN TCT GAA GGG GAA TCC      (SEQ ID NO: 33)

5' CDR2-H1: CAC GGA GTC TGC GTA SNN TTT SNN SNN TCC ATC ATA TGA  (SEQ ID NO: 34)
TAT AAC

5' CDR3-H1: TTT GCC CCA GAC GTC CAN SNN GTA GTA GTG GTC ATA GTC  (SEQ ID NO: 35)
ACC CAA CAG SNN CTG ATC TCT 3) 5' Primer 3
5' CDR1-H1: TCT GGA TTC CCC TTC AGA NNS TTT GCT ATG CAC TGG      (SEQ ID NO: 36)

5' CDR2-H1: ATA TCA TAT GAT GGA NNS NNS AAA NNS TAC GCA GAC TCC  (SEQ ID NO: 37)
GTG AAG

5' CDR3-H1: GCG AGA GAT CAG NNS CTG TTG GGT GAC TAT GAC CAC      (SEQ ID NO: 38)
TAC TAC NNS NTG GAC GTC TGG 4) 3' VH-CH-ApaI
5' CGA TGG GCC CTT GGT GCT AGC TGA AGA GAC CGT GAC               (SEQ ID NO: 39)
```

2D3 was selected. The final construct can be kept in the ETA$_{(252-608)}$ format or other toxins or effectors can be engineered in such as modified bouganin. The final sequence of the selected clone is shown in FIG. 10.

Purification of the Affinity Matured VB6-011-Bouganin:

The final clone, 2D3 was engineered with the de-bouganin toxin using the ApaI and SfiI restriction enzymes. Briefly, VB6-011ETA$_{(252-608)}$ was digested with ApaI and SfiI and the two fragments were obtained. The first fragment corresponds to the pING3302 plasmid with the VH and VL-CL and the second fragment to CH-ETA$_{(252-608)}$. The first fragment was purified and ligated with the CH-de-bouganin fragment pre-digested with the same enzymes creating the VB6-011-Boug-2D3/3302 vector. Fed batch fermentation of VB6-011-2D3 clone was performed in a 20 L CHEMAP fermenter using GMM medium (14). A 2 L shake flask with 500 mL of GMM containing 25 μg/mL of tetracycline and supplemented with trace element D, calcium chloride, nicotinic acid and thiamine was inoculated with one vial of the MCB. The cells were placed in a shaking incubator set at 28° C. with a constant agitation of 200 rpm. The culture was grown until an OD$_{600}$ of 2.0-2.5 was attained. Then, 150 mL of the seed culture was used to inoculate a 20 L chemap bioreactor containing 15 L of GMM media with supplement elements as described previously. The temperature was set at 28° C. and the pH maintained at 7.0 with the addition of a 50% ammonium hydroxide solution via the pH control loop throughout the entire fermentation. The agitation rate was set at 300 rpm with airflow of 3 slpm and incremented successively at 600 rpm and 6 slpm and then at 1000 rpm and 10 slpm to maintained the dissolved oxygen above 41% during the batch phase. When the carbon source of the batch media was exhausted, the dissolved oxygen increased above 90% which triggered the addition of feed 1 solution (50% glycerol solution). Then, the D0 setpoint was set at 41% and the feeding was based on a cascade control of the DO reading. At an optical density of 100, the culture was induced by switching to feed 2 solution (50% glycerol+30 g/L arabinose solution) and the induction was carried out for 48 hours under the same control as the feed 1.

At 48 hours post induction, the culture was harvested and centrifuged at 8000 rpm for 30 min, then purified using CM-sepharose, Chelating-sepharose and SP-sepharose columns followed by a size exclusion column. Briefly, the supernatant was concentrated and diafiltered against 20 mM sodium phosphate pH 7±0.1. The diafiltered concentrated supernatant was then applied onto a CM-sepharose column equilibrated with 20 mM sodium phosphate, 25 mM NaCl pH 7±0.1. The column was washed with 20 mM sodium phosphate, 25 mM NaCl pH 6.9±0.1. Bound VB6-008 was subsequently eluted with 20 mM sodium phosphate, 150 mM NaCl pH 7.5±0.1. The CM-Sepharose eluate was adjusted to a final concentration of 0.25% triton-X100 and applied to a charged chelating sepharose column. The Chelating-sepharose column was then washed with 20 mM sodium phosphate, 150 mM NaCl, 10 mm imidazole pH 7.5±0.1. The bound VB6-008 was eluted with 20 mM sodium phosphate, 150 mM NaCl, 250 mM imidazole pH 7.5±0.1 and collected in 5 mL fractions. The absorbance at A280 nm was determined for each fraction and the fractions with material were pooled and the pH and conductivity adjusted to 6 and 5.8 mS, respectively. Then, the material was applied onto a SP-sepharose column, washed with 20 mM sodium phosphate, 25 mM NaCl pH 6.0±0.1 and eluted with 20 mM sodium phosphate, 300 mM NaCl pH 7.5±0.1. The pooled fraction of the SP-sepharose column were applied onto a SEC-200 column equilibrated with 20 mM sodium phosphate, 150 mM NaCl, pH 7.5±0.1. Fractions containing the full length VB6-011-Boug-2D3 were concentrated using centricon column.

Biological Activity of the Affinity Matured VB6-011:

a. Flow Cytometry Verification of Boug Modification

Figure 11:
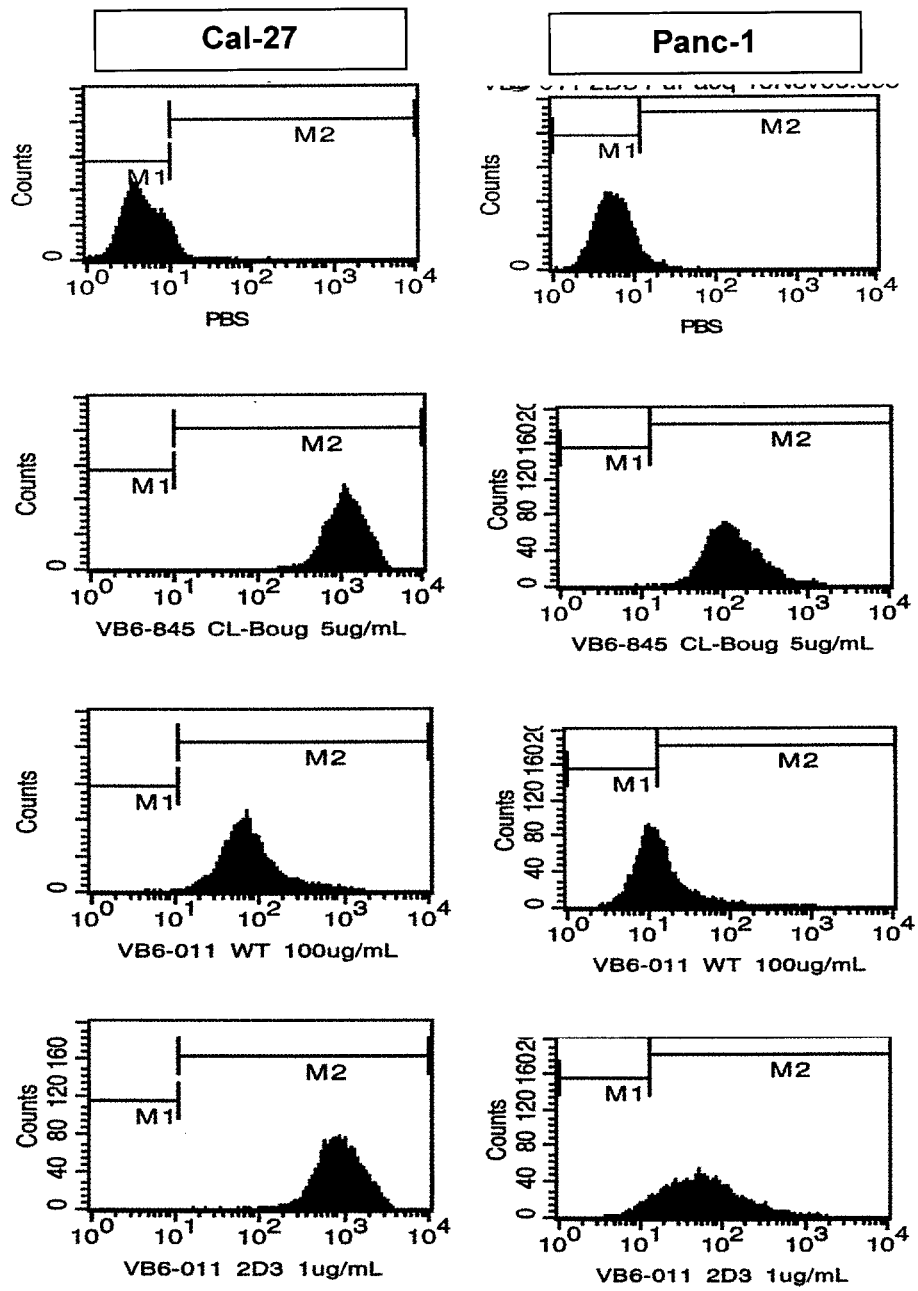
FIG. 11 is Flow Cytometry analysis for binding of purified optimized affinity matured VB6-011 clone 2D3 conjugated to bouganin compared with parental VB6-011 and positive control VB6-845 on both an antigen high positive (Cal-27) and antigen low positive (PANC-1) cell line.

To verify that VB6-011 2D3 boug has improved affinity with respect to the wild type VB6-011 boug flow cytometery was carried out using and high 011 binding cell line (Cal-27) and a moderate to low binding cell line PANC-1. The results are shown in FIG. 11 and Table 8.

b. Affinity Measurement

Flow cytometry is used to measure the affinity of VB6-011-Boug. Increased concentrations of the purified VB6-011-Boug is incubated against a fixed number of Cal-27 cells to establish a saturation curve. Binding is detected using the rabbit anti-boug and compared to wild-type VB6-011. The binding affinity expressed as the dissociation constant, $K_D$ will be calculated by the Lineweaver-Burk method of plotting the inverse of the median fluorescence as function of the inverse of the antibody concentration. The dissociation constant is determined by the following equation: $1/F=1/F_{Max}+(K_D/F_{Max})(1/[scFv])$, where F corresponds to the background subtracted median fluorescence and $F_{Max}$ is calculated from the plot.

TMA:

VB6-011-Boug is first tested against fixed saos-2 cell line pellets to define the optimal conditions for staining. The IHC is then carried out.

MTS Assay:

An MTS assay is used to determine the IC$_{50}$ values of the variants using the antigen positive cell lines, A-375 and Saos-2, and antigen negative cell line Panc-1. The IC$_{50}$ of the variants are determined and compared to VB6-011-Boug wild-type.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Amino acid sequence of CDR regions of the kappa light chain

| Subclass | CDR1 | CDR2 | CDR3 | SEQ ID NOS: |
|---|---|---|---|---|
| 2 | QGLVYSDGNMY | KVSYRDS | QGTHWP | 40-42 |
| 1 | QDISKF | DASNVQT | VFIFPPSDEQL | 43-45 |
| 1 | QGISTY | AASTLQS | QKDNSDPRT | 46-48 |
| 2 | QSLLNSNGNN | LGFNRAS | MQTLQIPYT | 49-51 |
| 1 | VRTLSNY | AAATLQR | LQYNSYPLT | 52-54 |
| 1 | VRV*LVI | ATSTLQS | QQSYTTPYT | 55-57 |
| 2 | QSLVHSNEYNY | LGSNRAS | TQALQIPIT | 58-60 |
| 1 | QGISTY | AVSTLQS | QQLNSYPIT | 61-63 |

*-Sequence is unclear

TABLE 2

Amino acid sequence of CDR regions of the V_H fragment

| Subclass | CDR1 | CDR2 | CDR3 | SEQ ID NOS: |
|---|---|---|---|---|
| 3 | GFTFSSYA | AISGNGGRT | AKDRWGGSIVAAGGTGFDP | 64-66 |
| 1 | GYTFTGYY | RINPNSGGT | ARDHSYGDSNWFDP | 67-69 |
| 4 | GGSISSGGYY | YIYYSGTT | SLKLSSVTAAD | 70-72 |
| 3 | GFTFSGSA | RIRTKANNYAT | TRHEWRGKEGDY | 73-75 |
| 3 | GFTFDDYA | GTSWNSATI | ARDMGSGWFTAFHI | 76-78 |
| 1 | VTPLPALI | ISAYKGNT | AREPMTTVTVDY | 79-81 |
| 3 | GFTFSNYA | GISGSGHST | AKSERAVTVILVVITGVYFDY | 82-84 |
| 3 | GFSFSNSG | LLSYDGVSK | ATDRARGYYDSGGAYFDY | 85-87 |

TABLE 3

FMAT Screening Results from Colon Immunotoxin Library

| Screening Step | # of Clones Screened | # of Clones Positive | % of Screened in this Step | % of Total Screened |
|---|---|---|---|---|
| First FMAT | 44,372 | 2016 | 4.5% | N/A |
| Second FMAT | 2016 | 174 | 8.6% | 0.4% |
| Third FMAT positive and negative cells | 174 | 8 | 4.5% | 0.02% |

*Initially the library contained 520,000 clones, at this time approximately 45000 have been screened

TABLE 4

Screening FMAT Passed Clones of Colon Based Immunotoxin Library

| | SW-480 (+) | | CA-46 (−) | |
|---|---|---|---|---|
| Clone | IC50 (MTS) | MFI | IC50 (MTS) | MFI |
| VB6-845ETA(252-608) | 0.2 pM | 144 | — | 1.1 |
| VB6-011ETA(252-608) | 2.8 nM | | — | |
| VB6-A8ETA(252-608) | 1.8 nM | 2.6 | — | 1.8 |
| VB6-H10ETA(252-608) | 1.85 nM | 3.5 | — | 1.1 |
| VB6-H7ETA(252-608) | 1.6 nM | 1.3 | — | 1.1 |
| VB6-B1ETA(252-608) | 0.7 nM | 5.3 | — | 1.1 |

TABLE 5

VB6-011ETA(252-608) Affinity Maturations Light Chain Motifs

| Light Chains | CDR1 Motif 1 | CDR1 Motif 2 | CDR3 Motif 1 | CDR3 Motif 2 |
|---|---|---|---|---|
| WT | S E S | S S S | Q Q Y | G S S |
| VL-1 | L K A | W Y Y | Q Q Y | G G A |
| VL-2 | L K A | W L E | L P C | G G A |
| VL-3 | L K A | W Y Y | Q Q Y | K R P |
| VL-4 | L K A | W L E | L P C | K R P |

TABLE 6

VB6-011ETA(252-608) VL2 Affinity Maturation Heavy Chain Motifs

| Heavy Chains | CDR1 | CDR2 | CDR3 |
|---|---|---|---|
| WT-VL2 | S | S T K Y | S . . . G L |
| 2D3 | A | M C K S | Y . . . M M |
| 11F11 | T | G V K T | Y . . . T M |
| 8E8 | V | M C K S | G . . . D L |
| 20A10 | V | G V K T | S . . . L L |

TABLE 7

Screening Results for Affinity Matured Clones of VB6-011ETA(252-608)

| | CDR1 | CDR2 | CDR3 | % apop (FMAT) | ELISA OD 450 | % M2 event |
|---|---|---|---|---|---|---|
| WT-VL2 | S | S T K Y | S . . . G L | 17 | 0.7 | 28.5 |
| 2D3 | A | M C K S | Y . . . M M | 33.4 | 1.1 | 74.68 |
| 11F11 | T | G V K T | Y . . . T M | 29.9 | 0.708 | 49 |
| 8E8 | V | M C K S | G . . . D L | 26 | 0.403 | 55.3 |
| 20A10 | V | G V K T | S . . . L L | 20 | 0.454 | 35.76 |

TABLE 8

% M2 Flow Cytometry on VB6-011-2D3 Bouganin

| Treatment | Cal 27 | Panc-1 |
|---|---|---|
| VB6-845-Boug | 235 | 20.4 |
| VB6-011 WT Boug | 13 | 2.1 |
| VB6-011 2D3 Boug | 170 | 9.5 |

REFERENCES

1. Molecular Immunology. Leeds, UK: Oxford University Press; 1996.
2. Fundamental Immunology.: Lippincott, Williams & Wilkins; 2003.
3. Arnold F H, Georgiou G. Directed Evolution Library Creation Methods and Protocols.: Humana Press; 2003.
4. Baldari C, Murray J A, Ghiara P, Cesareni G, Galeotti C L. A novel leader peptide which allows efficient secretion of a fragment of human interleukin 1 beta in *Saccharomyces cerevisiae*. EMBO J 1987; 6:229-234.

5. Clackson T, Hoogenboom H R, Griffiths A D, Winter G. Making antibody fragments using phage display libraries. Nature 1991; 352:624-628.
6. Cullen D, Gray G L, Wilson L J et al. Controlled Expression and Secretion of Bovine Chymosin in *Aspergillus Nidulans*. Nat Biotech 1987; 5:369-376.
7. Daugherty P S, Chen G, Iverson B L, Georgiou G. Quantitative analysis of the effect of the mutation frequency on the affinity maturation of single chain Fv antibodies. Proc Natl. Acad. Sci. U.S.A 2000; 97:2029-2034.
8. Davies D R, Padlan E A, Sheriff S. Antibody-antigen complexes. Annu. Rev. Biochem. 1990; 59:439-473.
9. Flenniken M L, Liepold L O, Crowley B E et al. Selective attachment and release of a chemotherapeutic agent from the interior of a protein cage architecture. Chem Commun. (Camb.) 2005447-449.
10. Giudicelli V, Chaume D, Lefranc M P. IMGT/V-QUEST, an integrated software program for immunoglobulin and T cell receptor V-J and V-D-J rearrangement analysis. Nucleic Acids Res 2004; 32:W435-W440.
11. Goeddel D V. Systems for heterologous gene expression. Methods Enzymol. 1990; 185:3-7.
12. Grossbard M L, Fidias P. Prospects for immunotoxin therapy of non-Hodgkin's lymphoma. Clin Immunol. Immunopathol. 1995; 76:107-114.
13. Harada H, Kawano M M, Huang N et al. Phenotypic difference of normal plasma cells from mature myeloma cells. Blood 1993; 81:2658-2663.
14. Hawkins R E, Russell S J, Winter G. Selection of phage antibodies by binding affinity. Mimicking affinity maturation. J Mol. Biol. 1992; 226:889-896.
15. Heyzer-Williams M G. B cells as effectors. Curr. Opin. Immunol. 2003; 15:354-361.
16. Hinnen A, Hicks J B, Fink G R. Transformation of yeast. Proc Natl. Acad. Sci. U.S.A 1978; 75:1929-1933.
17. Ho M, Kreitman R J, Onda M, Pastan I. In vitro antibody evolution targeting germline hot spots to increase activity of an anti-CD22 immunotoxin. J Biol. Chem. 2005; 280: 607-617.
18. Ito H, Fukuda Y, Murata K, Kimura A. Transformation of intact yeast cells treated with alkali cations. J Bacteriol. 1983; 153:163-168.
19. Jurcic J G, Caron P C, Scheinberg D A. Monoclonal antibody therapy of leukemia and lymphoma. Adv. Pharmacol. 1995; 33:287-314.
20. Kaufman R J, Murtha P, Davies M V. Translational efficiency of polycistronic mRNAs and their utilization to express heterologous genes in mammalian cells. EMBO J 1987; 6:187-193.
21. Kaufmann D, Weberskirch R. Efficient synthesis of protein-drug conjugates using a functionalizable recombinant elastin-mimetic polypeptide. Macromol. Biosci. 2006; 6:952-958.
22. Kreitman R J. Immunotoxins in cancer therapy. Curr. Opin. Immunol. 1999; 11:570-578.
23. Kreitman R J. Immunotoxins. Expert. Opin. Pharmacother. 2000; 1:1117-1129.
24. Kreitman R J, Wilson W H, Bergeron K et al. Efficacy of the anti-CD22 recombinant immunotoxin BL22 in chemotherapy-resistant hairy-cell leukemia. N. Engl. J Med. 2001; 345:241-247.
25. Kurjan J, Herskowitz I. Structure of a yeast pheromone gene (MF alpha): a putative alpha-factor precursor contains four tandem copies of mature alpha-factor. Cell 1982; 30:933-943.
26. Lewis J P, DeNardo G L, Denardo S J. Radioimmunotherapy of lymphoma: a U C Davis experience. Hybridoma 1995; 14:115-120.
27. Low N M, Holliger P H, Winter G. Mimicking somatic hypermutation: affinity maturation of antibodies displayed on bacteriophage using a bacterial mutator strain. J Mol. Biol. 1996; 260:359-368.
28. Luckow V A, Summers M D. High level expression of nonfused foreign genes with *Autographa californica* nuclear polyhedrosis virus expression vectors. Virology 1989; 170:31-39.
29. Min L. Applications of display technology in protein analysis. Nat Biotech 2000; 18:1251-1256.
30. Neuberger M S, Milstein C. Somatic hypermutation. Curr. Opin. Immunol. 1995; 7:248-254.
31. Salvatore G, Beers R, Margulies I, Kreitman R J, Pastan I. Improved cytotoxic activity toward cell lines and fresh leukemia cells of a mutant anti-CD22 immunotoxin obtained by antibody phage display. Clin Cancer Res 2002; 8:995-1002.
32. Sambrook J, MacCallum P, Russell D. Molecular Cloning: A Laboratory Manual.: Cold Spring Harbor Laboratory Press; 2001.
33. Schier R, McCall A, Adams G P et al. Isolation of picomolar affinity anti-c-erbB-2 single-chain Fv by molecular evolution of the complementarity determining regions in the center of the antibody binding site. J Mol. Biol. 1996; 263:551-567.
34. Schultz L D, Tanner J, Hofmann K J et al. Expression and secretion in yeast of a 400-kDa envelope glycoprotein derived from Epstein-Barr virus. Gene 1987; 54:113-123.
35. Seed B. An LFA-3 cDNA encodes a phospholipid-linked membrane protein homologous to its receptor CD2. Nature 1987; 329:840-842.
36. Sinkar V P, White F F, Gordon M P. Molecular Biology of the RI Plasmid—A Review. J. Biosci. 1987; 11:47-57.
37. Smith G E, Summers M D, Fraser M J. Production of human beta interferon in insect cells infected with a baculovirus expression vector. Mol. Cell Biol. 1983; 3:2156-2165.
38. Tait R C, Horton R M. Genetic Engineering with PCR. Genetic Engineering with PCR. Norfolk UK: Horizen Scientific Press; 1998:
39. Tomlinson I M, Cox J P, Gherardi E, Lesk A M, Chothia C. The structural repertoire of the human V kappa domain. EMBO J 1995; 14:4628-4638.
40. Tomlinson I M, Walter G, Jones P T et al. The imprint of somatic hypermutation on the repertoire of human germline V genes. J Mol. Biol. 1996; 256:813-817.
41. Uckun F M, Reaman G H. Immunotoxins for treatment of leukemia and lymphoma. Leuk. Lymphoma 1995; 18:195-201.
42. Wagner S D, Milstein C, Neuberger M S. Codon bias targets mutation. Nature 1995; 376:732.
43. Wahl R L. Experimental radioimmunotherapy. A brief overview. Cancer 1994; 73:989-992.
44. Weissensteiner T, Griffin H G, Griffin A. PCR Technology: Current Innovations. Boca Raton, Fla.: CRC Press; 2004.
45. Yang W P, Green K, Pinz-Sweeney S et al. CDR walking mutagenesis for the affinity maturation of a potent human anti-HIV-1 antibody into the picomolar range. J Mol. Biol. 1995; 254:392-403.
46. Zambryski P, Herrerra-Estrella L, DeBlock M, Van Montagu M. In: Setlow J, Hollaender A, eds. Genetic Engineering: Principles and Methods. Vol 6. New York, N.Y.: Plenum Press; 1984:253-278.
47. Zhang Z, Gildersleeve J, Yang Y Y et al. A new strategy for the synthesis of glycoproteins. Science 2004; 303:371-373.

We claim:

1. A method of screening a library of immunotoxins comprising a plurality of different antibody heavy chain variable regions derived from B cells from a subject and/or a plurality of different antibody light chain variable regions derived from B cells from a subject linked to a cytotoxin for binding to a target molecule comprising the steps of:
(a) providing the library of immunotoxins prepared according to the following method:
    (i) constructing a library of vectors, wherein each vector encodes an immunotoxin and comprises 1) a nucleic acid sequence that encodes a ligand protein comprising an antibody heavy chain variable region derived from a B cell from a subject and/or an antibody light chain variable region derived from a B cell from a subject linked to 2) a nucleic acid sequence encoding a cytotoxin;
    (ii) transforming host cells with the library of vectors to produce a library of recombinant cells;
    (iii) cloning the recombinant cells; and
    (iv) expressing the library of immunotoxins, the host cell express the immunotoxins as soluble proteins;
(b) contacting the immunotoxins with a target molecule; and
(c) determining the binding of the immunotoxins to the target molecule.

2. The method according to claim 1, wherein the B cells are mature B cells.

3. The method according to claim 1, wherein the B cells are from a subject who has cancer.

4. The method according to claim 1, wherein the cytotoxin is a ribosome-inactivating polypeptide.

5. The method according to claim 4, wherein the cytotoxin is selected from the group consisting of gelonin, bouganin, saporin, ricin, ricin A chain, bryodin, diphtheria, restrictocin and *Pseudomonas* exotoxin A or variants thereof.

6. The method according to claim 5, wherein the cytotoxin is modified bouganin or a variant thereof.

7. The method according to claim 5, wherein the cytotoxin is a variant of *Pseudomonas* exotoxin A that does not have a functional cell binding domain.

8. The method according to claim 7, wherein the cytotoxin is a truncated form of *Pseudomonas* exotoxin A that consists of amino acids 252-608 or a variant thereof, and an endoplasmic reticulum retention sequence.

9. The method according to claim 1 wherein the target molecule is on a target cell.

10. The method according to claim 9, wherein the target cell is a cancer cell.

11. The method of claim 10 further comprising:
(d) determining the cytotoxicity of the immunotoxin to the target cell.

* * * * *

SEQUENCE LISTING

<160> NUMBER OF SEQ ID NOS: 88

<210> SEQ ID NO 1
<211> LENGTH: 125
<212> TYPE: PRT
<213> ORGANISM: Artificial sequence
<220> FEATURE:
<223> OTHER INFORMATION: VH 011-2D3

<400> SEQUENCE: 1

Gln Val Gln Leu Val Glu Ser Gly Gly Gly Val Val Gln Pro Gly Arg
1               5                   10                  15

Ser Leu Gly Leu Ser Cys Ala Ala Ser Gly Phe Pro Phe Arg Ala Phe
            20                  25                  30

Ala Met His Trp Val Arg Gln Ala Leu Gly Lys Gly Leu Glu Trp Val
        35                  40                  45

Ala Val Ile Ser Tyr Asp Gly Met Cys Lys Ser Tyr Ala Asp Ser Val
    50                  55                  60

Lys Gly Arg Phe Thr Ile Ser Arg Asp Thr Ser Lys Asn Thr Val Tyr
65                  70                  75                  80

Leu Lys Met Asn Ser Leu Lys Thr Glu Asp Thr Ala Val Tyr Tyr Cys
                85                  90                  95

Ala Arg Asp Gln Thr Leu Leu Gly Asp Tyr Asp His Tyr Tyr Met Met
            100                 105                 110

Asp Val Trp Gly Lys Arg Thr Thr Val Thr Val Ser Ser
        115                 120                 125

<210> SEQ ID NO 2
<211> LENGTH: 113
<212> TYPE: PRT
<213> ORGANISM: Artificial sequence
<220> FEATURE:
<223> OTHER INFORMATION: VL 011-2D3

<400> SEQUENCE: 2

Asp Ile Val Leu Thr Gln Ser Pro Gly Thr Leu Ser Leu Ser Pro Gly
1               5                   10                  15

Glu Arg Ala Thr Leu Ser Cys Arg Ala Leu Lys Ala Val Trp Leu Glu
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Met Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Pro Cys Gly Gly Ala Pro
                85                  90                  95

Gln Thr Pro Gln Ile Thr Phe Gly Gly Gly Thr Lys Val Glu Ile Lys
            100                 105                 110

Arg

<210> SEQ ID NO 3
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)

```
<223> OTHER INFORMATION: n = a or g
<220> FEATURE:
<221> NAME/KEY: misc_feature
<222> LOCATION: (30)..(30)
<223> OTHER INFORMATION: n = a or g

<400> SEQUENCE: 3
ccagccatgg cgcagntgca gctggtgcan tctgg                                35

<210> SEQ ID NO 4
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n = c or g
<220> FEATURE:
<221> NAME/KEY: misc_feature
<222> LOCATION: (27)..(27)
<223> OTHER INFORMATION: n = a or g

<400> SEQUENCE: 4
ccagccatgg cgnaggtcca gctggtncag tctgg                                35

<210> SEQ ID NO 5
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n = a or g

<400> SEQUENCE: 5
ccagccatgg cgcagntcac cttgaaggag tctgg                                35

<210> SEQ ID NO 6
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n = c or g

<400> SEQUENCE: 6
ccagccatgg cgnaggtgca gctggtggag tctgg                                35

<210> SEQ ID NO 7
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (31)..(31)
<223> OTHER INFORMATION: n = a or t
<220> FEATURE:
<221> NAME/KEY: misc_feature
<222> LOCATION: (33)..(33)
<223> OTHER INFORMATION: n = c or t

<400> SEQUENCE: 7
```
ccagccatgg cggaggtgca gctggtggag ncngg                                35

<210> SEQ ID NO 8
<211> LENGTH: 35
<212> TYPE: DNA
<213> ORGANISM: Artificial sequence
<220> FEATURE:
<223> OTHER INFORMATION: primer

<400> SEQUENCE: 8
ccagccatgg cgcaggtgca gctacagcag tgggg                                35

<210> SEQ ID NO 9
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n = c or g
<220> FEATURE:
<221> NAME/KEY: misc_feature
<222> LOCATION: (33)..(33)
<223> OTHER INFORMATION: n = c or g

<400> SEQUENCE: 9
ccagccatgg cgcagntgca gctgcaggag tcngg                                35

<210> SEQ ID NO 10
<211> LENGTH: 38
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n = a or g

<400> SEQUENCE: 10
ccagccatgg cgcaggangt gcagctggtg cagtctgg                             38

<210> SEQ ID NO 11
<211> LENGTH: 38
<212> TYPE: DNA
<213> ORGANISM: Artificial sequence
<220> FEATURE:
<223> OTHER INFORMATION: primer

<400> SEQUENCE: 11
ccagccatgg cgcagcaggt acagctgcag cagtcagg                             38

<210> SEQ ID NO 12
<211> LENGTH: 35
<212> TYPE: DNA
<213> ORGANISM: Artificial sequence
<220> FEATURE:
<223> OTHER INFORMATION: primer

<400> SEQUENCE: 12
tgccaggggg aagaccgatg ggcccttggt gctag                                35

<210> SEQ ID NO 13
<211> LENGTH: 64
<212> TYPE: DNA

<213> ORGANISM: Artificial sequence
<220> FEATURE:
<223> OTHER INFORMATION: primer
<220> FEATURE:
<221> NAME/KEY: misc_feature
<222> LOCATION: (51)..(51)
<223> OTHER INFORMATION: n = a or t

<400> SEQUENCE: 13
tcgcggccca accggccatg gcgcaccatc atcaccatca cgacatccag ntgacccagt     60
ctcc                                                                 64

<210> SEQ ID NO 14
<211> LENGTH: 64
<212> TYPE: DNA
<213> ORGANISM: Artificial sequence
<220> FEATURE:
<223> OTHER INFORMATION: primer

<400> SEQUENCE: 14
tcgcggccca accggccatg gcgcaccatc atcaccatca cgatgttgtg atgactcagt     60
ctcc                                                                 64

<210> SEQ ID NO 15
<211> LENGTH: 64
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (51)..(51)
<223> OTHER INFORMATION: n = a or t
<220> FEATURE:
<221> NAME/KEY: misc_feature
<222> LOCATION: (56)..(56)
<223> OTHER INFORMATION: n = a or g

<400> SEQUENCE: 15
tcgcggccca accggccatg gcgcaccatc atcaccatca cgaaattgtg ntgacncagt     60
ctcc                                                                 64

<210> SEQ ID NO 16
<211> LENGTH: 64
<212> TYPE: DNA
<213> ORGANISM: Artificial sequence
<220> FEATURE:
<223> OTHER INFORMATION: primer

<400> SEQUENCE: 16
tcgcggccca accggccatg gcgcaccatc atcaccatca cgatattgtg atgacccaca     60
ctcc                                                                 64

<210> SEQ ID NO 17
<211> LENGTH: 64
<212> TYPE: DNA
<213> ORGANISM: Artificial sequence
<220> FEATURE:
<223> OTHER INFORMATION: primer

<400> SEQUENCE: 17
tcgcggccca accggccatg gcgcaccatc atcaccatca cgaaacgaca ctcacgcagt     60
ctcc                                                                 64

```
<210> SEQ ID NO 18
<211> LENGTH: 64
<212> TYPE: DNA
<213> ORGANISM: Artificial sequence
<220> FEATURE:
<223> OTHER INFORMATION: primer

<400> SEQUENCE: 18
tcgcggccca accggccatg gcgcaccatc atcaccatca cgaaattgtg ctgactcagt    60
ctcc                                                                64

<210> SEQ ID NO 19
<211> LENGTH: 48
<212> TYPE: DNA
<213> ORGANISM: Artificial sequence
<220> FEATURE:
<223> OTHER INFORMATION: primer

<400> SEQUENCE: 19
gcactcgagc tactaacact ctcccctgtt gaagctcttt gtgacggg                 48

<210> SEQ ID NO 20
<211> LENGTH: 30
<212> TYPE: DNA
<213> ORGANISM: Artificial sequence
<220> FEATURE:
<223> OTHER INFORMATION: primer

<400> SEQUENCE: 20
gaattcctgc aggtctatgg aacgataaat                                     30

<210> SEQ ID NO 21
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n = g or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n = t, c or g
<220> FEATURE:
<221> NAME/KEY: misc_feature
<222> LOCATION: (22)..(22)
<223> OTHER INFORMATION: n = g or c
<220> FEATURE:
<221> NAME/KEY: misc_feature
<222> LOCATION: (23)..(24)
<223> OTHER INFORMATION: n is a, c, g, or t

<400> SEQUENCE: 21
gtagctgcta ctaacnnnct nnnnggccct gcagga                              36

<210> SEQ ID NO 22
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
```

<223> OTHER INFORMATION: n = g or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n = g or c
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: n = g or c
<220> FEATURE:
<221> NAME/KEY: misc_feature
<222> LOCATION: (23)..(24)
<223> OTHER INFORMATION: n is a, c, g, or t

<400> SEQUENCE: 22
gtaccaggct aagtannnnn nnnnaacact ctgact                              36

<210> SEQ ID NO 23
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n = g or c
<220> FEATURE:
<221> NAME/KEY: misc_feature
<222> LOCATION: (17)..(18)
<223> OTHER INFORMATION: n is a, c, g, or t

<400> SEQUENCE: 23
catgccagtg gccctnnngg atgcaccata                                    30

<210> SEQ ID NO 24
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n = g or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n = g or c
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: n = g or c
<220> FEATURE:
<221> NAME/KEY: misc_feature
<222> LOCATION: (23)..(24)
<223> OTHER INFORMATION: n is a, c, g, or t

<400> SEQUENCE: 24
ctgaggtgag ctaccnnnnn nnnnacagta atacac                                    36

<210> SEQ ID NO 25
<211> LENGTH: 33
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n = g or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n = g or c
<220> FEATURE:
<221> NAME/KEY: misc_feature
<222> LOCATION: (20)..(21)
<223> OTHER INFORMATION: n is a, c, g, or t

<400> SEQUENCE: 25
aggtgtctga ggtgnnnnnn natactgctg aca                                       33

<210> SEQ ID NO 26
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n = g or c
<220> FEATURE:
<221> NAME/KEY: misc_feature
<222> LOCATION: (19)..(19)
<223> OTHER INFORMATION: n = a, c or g
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: n = g or c

<400> SEQUENCE: 26
ctctcctgca gggccnnnna gnnngttagt agcagc                                    36

<210> SEQ ID NO 27
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:

```
<221> NAME/KEY: misc_feature
<222> LOCATION: (18)..(18)
<223> OTHER INFORMATION: n = g or c
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n = g or c
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: n = g or c

<400> SEQUENCE: 27
gccagtcaga gtgttnnnnn nnnntactta gcctgg                              36

<210> SEQ ID NO 28
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n = g or c

<400> SEQUENCE: 28
atctatggtg catccnnnag ggccactggc                                     30

<210> SEQ ID NO 29
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n = g or c
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n = g or c
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: n = g or c

<400> SEQUENCE: 29
gcagtgtatt actgtnnnnn nnnnggtagc tcacct                              36
```

```
<210> SEQ ID NO 30
<211> LENGTH: 33
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n = g or c
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n = g or c
<220> FEATURE:
<221> NAME/KEY: misc_feature
<222> LOCATION: (22)..(22)
<223> OTHER INFORMATION: n is a, c, g, or t

<400> SEQUENCE: 30
tactgtcagc agtatnnnnn nncacctcag aca                                33

<210> SEQ ID NO 31
<211> LENGTH: 36
<212> TYPE: DNA
<213> ORGANISM: Artificial sequence
<220> FEATURE:
<223> OTHER INFORMATION: primer

<400> SEQUENCE: 31
ctcgagtcac taacactctc ccctgttgaa gctctt                             36

<210> SEQ ID NO 32
<211> LENGTH: 30
<212> TYPE: DNA
<213> ORGANISM: Artificial sequence
<220> FEATURE:
<223> OTHER INFORMATION: primer

<400> SEQUENCE: 32
gaattcctgc aggtctatgg aacgataaat                                    30

<210> SEQ ID NO 33
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n = g or c
<220> FEATURE:
<221> NAME/KEY: misc_feature
<222> LOCATION: (20)..(21)
<223> OTHER INFORMATION: n is a, c, g, or t

<400> SEQUENCE: 33
gacccagtgc atagcaaann ntctgaaggg gaatcc                             36

<210> SEQ ID NO 34
```

```
<211> LENGTH: 45
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(16)
<223> OTHER INFORMATION: n = g or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n = g or c
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: n = g or c
<220> FEATURE:
<221> NAME/KEY: misc_feature
<222> LOCATION: (26)..(27)
<223> OTHER INFORMATION: n is a, c, g, or t

<400> SEQUENCE: 34
cacggagtct gcgtannntt tnnnnnntcc atcatatgat ataac             45

<210> SEQ ID NO 35
<211> LENGTH: 60
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n = g or c
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (49)..(49)
<223> OTHER INFORMATION: n = g or c
<220> FEATURE:
<221> NAME/KEY: misc_feature
<222> LOCATION: (50)..(51)
<223> OTHER INFORMATION: n is a, c, g, or t

<400> SEQUENCE: 35
tttgccccag acgtccannn ngtagtagtg gtcatagtca cccaacagnn nctgatctct    60

<210> SEQ ID NO 36
<211> LENGTH: 36
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
```

<222> LOCATION: (21)..(21)
<223> OTHER INFORMATION: n = g or c

<400> SEQUENCE: 36
tctggattcc ccttcagann ntttgctatg cactgg                          36

<210> SEQ ID NO 37
<211> LENGTH: 45
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n = g or c
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n = g or c
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: n = g or c

<400> SEQUENCE: 37
atatcatatg atggannnnn naaannntac gcagactccg tgaag                45

<210> SEQ ID NO 38
<211> LENGTH: 57
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (15)..(15)
<223> OTHER INFORMATION: n = g or c
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: n = g or c
<220> FEATURE:
<221> NAME/KEY: misc_feature
<222> LOCATION: (46)..(46)
<223> OTHER INFORMATION: n is a, c, g, or t

<400> SEQUENCE: 38
gcgagagatc agnnnctgtt gggtgactat gaccactact acnnnntgga cgtctgg   57

<210> SEQ ID NO 39
<211> LENGTH: 36
<212> TYPE: DNA

```
<213> ORGANISM: Artificial sequence
<220> FEATURE:
<223> OTHER INFORMATION: primer

<400> SEQUENCE: 39
cgatgggccc ttggtgctag ctgaagagac cgtgac                                36

<210> SEQ ID NO 40
<211> LENGTH: 11
<212> TYPE: PRT
<213> ORGANISM: Homo sapiens

<400> SEQUENCE: 40

Gln Gly Leu Val Tyr Ser Asp Gly Asn Met Tyr
1               5                   10

<210> SEQ ID NO 41
<211> LENGTH: 7
<212> TYPE: PRT
<213> ORGANISM: Homo sapiens

<400> SEQUENCE: 41

Lys Val Ser Tyr Arg Asp Ser
1               5

<210> SEQ ID NO 42
<211> LENGTH: 6
<212> TYPE: PRT
<213> ORGANISM: Homo sapiens

<400> SEQUENCE: 42

Gln Gly Thr His Trp Pro
1               5

<210> SEQ ID NO 43
<211> LENGTH: 6
<212> TYPE: PRT
<213> ORGANISM: Homo sapiens

<400> SEQUENCE: 43

Gln Asp Ile Ser Lys Phe
1               5

<210> SEQ ID NO 44
<211> LENGTH: 7
<212> TYPE: PRT
<213> ORGANISM: Homo sapiens

<400> SEQUENCE: 44

Asp Ala Ser Asn Val Gln Thr
1               5

<210> SEQ ID NO 45
<211> LENGTH: 11
<212> TYPE: PRT
<213> ORGANISM: Homo sapiens

<400> SEQUENCE: 45

Val Phe Ile Phe Pro Pro Ser Asp Glu Gln Leu
1               5                   10

<210> SEQ ID NO 46
<211> LENGTH: 6
<212> TYPE: PRT
<213> ORGANISM: Homo sapiens
```

```
<400> SEQUENCE: 46

Gln Gly Ile Ser Thr Tyr
1               5

<210> SEQ ID NO 47
<211> LENGTH: 7
<212> TYPE: PRT
<213> ORGANISM: Homo sapiens

<400> SEQUENCE: 47

Ala Ala Ser Thr Leu Gln Ser
1               5

<210> SEQ ID NO 48
<211> LENGTH: 9
<212> TYPE: PRT
<213> ORGANISM: Homo sapiens

<400> SEQUENCE: 48

Gln Lys Asp Asn Ser Asp Pro Arg Thr
1               5

<210> SEQ ID NO 49
<211> LENGTH: 10
<212> TYPE: PRT
<213> ORGANISM: Homo sapiens

<400> SEQUENCE: 49

Gln Ser Leu Leu Asn Ser Asn Gly Asn Asn
1               5                   10

<210> SEQ ID NO 50
<211> LENGTH: 7
<212> TYPE: PRT
<213> ORGANISM: Homo sapiens

<400> SEQUENCE: 50

Leu Gly Phe Asn Arg Ala Ser
1               5

<210> SEQ ID NO 51
<211> LENGTH: 9
<212> TYPE: PRT
<213> ORGANISM: Homo sapiens

<400> SEQUENCE: 51

Met Gln Thr Leu Gln Ile Pro Tyr Thr
1               5

<210> SEQ ID NO 52
<211> LENGTH: 7
<212> TYPE: PRT
<213> ORGANISM: Homo sapiens

<400> SEQUENCE: 52

Val Arg Thr Leu Ser Asn Tyr
1               5

<210> SEQ ID NO 53
<211> LENGTH: 7
<212> TYPE: PRT
<213> ORGANISM: Homo sapiens

<400> SEQUENCE: 53
```

Ala Ala Ala Thr Leu Gln Arg
1               5

<210> SEQ ID NO 54
<211> LENGTH: 9
<212> TYPE: PRT
<213> ORGANISM: Homo sapiens

<400> SEQUENCE: 54

Leu Gln Tyr Asn Ser Tyr Pro Leu Thr
1               5

<210> SEQ ID NO 55
<211> LENGTH: 7
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 55

Val Arg Val Xaa Leu Val Ile
1               5

<210> SEQ ID NO 56
<211> LENGTH: 7
<212> TYPE: PRT
<213> ORGANISM: Homo sapiens

<400> SEQUENCE: 56

Ala Thr Ser Thr Leu Gln Ser
1               5

<210> SEQ ID NO 57
<211> LENGTH: 9
<212> TYPE: PRT
<213> ORGANISM: Homo sapiens

<400> SEQUENCE: 57

Gln Gln Ser Tyr Thr Thr Pro Tyr Thr
1               5

<210> SEQ ID NO 58
<211> LENGTH: 11
<212> TYPE: PRT
<213> ORGANISM: Homo sapiens

<400> SEQUENCE: 58

Gln Ser Leu Val His Ser Asn Glu Tyr Asn Tyr
1               5                   10

<210> SEQ ID NO 59
<211> LENGTH: 7
<212> TYPE: PRT
<213> ORGANISM: Homo sapiens

<400> SEQUENCE: 59

Leu Gly Ser Asn Arg Ala Ser
1               5

<210> SEQ ID NO 60
<211> LENGTH: 9
<212> TYPE: PRT
<213> ORGANISM: Homo sapiens

<400> SEQUENCE: 60

Thr Gln Ala Leu Gln Ile Pro Ile Thr
1               5

<210> SEQ ID NO 61
<211> LENGTH: 6
<212> TYPE: PRT
<213> ORGANISM: Homo sapiens

<400> SEQUENCE: 61

Gln Gly Ile Ser Thr Tyr
1               5

<210> SEQ ID NO 62
<211> LENGTH: 7
<212> TYPE: PRT
<213> ORGANISM: Homo sapiens

<400> SEQUENCE: 62

Ala Val Ser Thr Leu Gln Ser
1               5

<210> SEQ ID NO 63
<211> LENGTH: 9
<212> TYPE: PRT
<213> ORGANISM: Homo sapiens

<400> SEQUENCE: 63

Gln Gln Leu Asn Ser Tyr Pro Ile Thr
1               5

<210> SEQ ID NO 64
<211> LENGTH: 8
<212> TYPE: PRT
<213> ORGANISM: Homo sapiens

<400> SEQUENCE: 64

Gly Phe Thr Phe Ser Ser Tyr Ala
1               5

<210> SEQ ID NO 65
<211> LENGTH: 9
<212> TYPE: PRT
<213> ORGANISM: Homo sapiens

<400> SEQUENCE: 65

Ala Ile Ser Gly Asn Gly Gly Arg Thr
1               5

<210> SEQ ID NO 66
<211> LENGTH: 19
<212> TYPE: PRT
<213> ORGANISM: Homo sapiens

<400> SEQUENCE: 66

Ala Lys Asp Arg Trp Gly Gly Ser Ile Val Ala Ala Gly Gly Thr Gly
1               5                   10                  15

Phe Asp Pro

<210> SEQ ID NO 67
<211> LENGTH: 8
<212> TYPE: PRT
<213> ORGANISM: Homo sapiens

<400> SEQUENCE: 67

Gly Tyr Thr Phe Thr Gly Tyr Tyr
1               5

<210> SEQ ID NO 68
<211> LENGTH: 9
<212> TYPE: PRT
<213> ORGANISM: Homo sapiens

<400> SEQUENCE: 68

Arg Ile Asn Pro Asn Ser Gly Gly Thr
1               5

<210> SEQ ID NO 69
<211> LENGTH: 14
<212> TYPE: PRT
<213> ORGANISM: Homo sapiens

<400> SEQUENCE: 69

Ala Arg Asp His Ser Tyr Gly Asp Ser Asn Trp Phe Asp Pro
1               5                   10

<210> SEQ ID NO 70
<211> LENGTH: 10
<212> TYPE: PRT
<213> ORGANISM: Homo sapiens

<400> SEQUENCE: 70

Gly Gly Ser Ile Ser Ser Gly Gly Tyr Tyr
1               5                   10

<210> SEQ ID NO 71
<211> LENGTH: 8
<212> TYPE: PRT
<213> ORGANISM: Homo sapiens

<400> SEQUENCE: 71

Tyr Ile Tyr Tyr Ser Gly Thr Thr
1               5

<210> SEQ ID NO 72
<211> LENGTH: 11
<212> TYPE: PRT
<213> ORGANISM: Homo sapiens

<400> SEQUENCE: 72

Ser Leu Lys Leu Ser Ser Val Thr Ala Ala Asp
1               5                   10

<210> SEQ ID NO 73
<211> LENGTH: 8
<212> TYPE: PRT
<213> ORGANISM: Homo sapiens

<400> SEQUENCE: 73

Gly Phe Thr Phe Ser Gly Ser Ala
1               5

<210> SEQ ID NO 74
<211> LENGTH: 11
<212> TYPE: PRT
<213> ORGANISM: Homo sapiens

<400> SEQUENCE: 74

Arg Ile Arg Thr Lys Ala Asn Asn Tyr Ala Thr
1               5                   10

<210> SEQ ID NO 75
<211> LENGTH: 12
<212> TYPE: PRT
<213> ORGANISM: Homo sapiens

<400> SEQUENCE: 75

Thr Arg His Glu Trp Arg Gly Lys Glu Gly Asp Tyr
1               5                   10

<210> SEQ ID NO 76
<211> LENGTH: 8
<212> TYPE: PRT
<213> ORGANISM: Homo sapiens

<400> SEQUENCE: 76

Gly Phe Thr Phe Asp Asp Tyr Ala
1               5

<210> SEQ ID NO 77
<211> LENGTH: 9
<212> TYPE: PRT
<213> ORGANISM: Homo sapiens

<400> SEQUENCE: 77

Gly Thr Ser Trp Asn Ser Ala Thr Ile
1               5

<210> SEQ ID NO 78
<211> LENGTH: 14
<212> TYPE: PRT
<213> ORGANISM: Homo sapiens

<400> SEQUENCE: 78

Ala Arg Asp Met Gly Ser Gly Trp Phe Thr Ala Phe His Ile
1               5                   10

<210> SEQ ID NO 79
<211> LENGTH: 8
<212> TYPE: PRT
<213> ORGANISM: Homo sapiens

<400> SEQUENCE: 79

Val Thr Pro Leu Pro Ala Leu Ile
1               5

<210> SEQ ID NO 80
<211> LENGTH: 8
<212> TYPE: PRT
<213> ORGANISM: Homo sapiens

<400> SEQUENCE: 80

Ile Ser Ala Tyr Lys Gly Asn Thr
1               5

<210> SEQ ID NO 81
<211> LENGTH: 12
<212> TYPE: PRT
<213> ORGANISM: Homo sapiens

<400> SEQUENCE: 81

Ala Arg Glu Pro Met Thr Thr Val Thr Val Asp Tyr

```
<210> SEQ ID NO 82
<211> LENGTH: 8
<212> TYPE: PRT
<213> ORGANISM: Homo sapiens

<400> SEQUENCE: 82

Gly Phe Thr Phe Ser Asn Tyr Ala
1               5

<210> SEQ ID NO 83
<211> LENGTH: 9
<212> TYPE: PRT
<213> ORGANISM: Homo sapiens

<400> SEQUENCE: 83

Gly Ile Ser Gly Ser Gly His Ser Thr
1               5

<210> SEQ ID NO 84
<211> LENGTH: 21
<212> TYPE: PRT
<213> ORGANISM: Homo sapiens

<400> SEQUENCE: 84

Ala Lys Ser Glu Arg Ala Val Thr Val Ile Leu Val Val Ile Thr Gly
1               5                   10                  15

Val Tyr Phe Asp Tyr
            20

<210> SEQ ID NO 85
<211> LENGTH: 8
<212> TYPE: PRT
<213> ORGANISM: Homo sapiens

<400> SEQUENCE: 85

Gly Phe Ser Phe Ser Asn Ser Gly
1               5

<210> SEQ ID NO 86
<211> LENGTH: 9
<212> TYPE: PRT
<213> ORGANISM: Homo sapiens

<400> SEQUENCE: 86

Leu Leu Ser Tyr Asp Gly Val Ser Lys
1               5

<210> SEQ ID NO 87
<211> LENGTH: 18
<212> TYPE: PRT
<213> ORGANISM: Homo sapiens

<400> SEQUENCE: 87

Ala Thr Asp Arg Ala Arg Gly Tyr Tyr Asp Ser Gly Gly Ala Tyr Phe
1               5                   10                  15

Asp Tyr

<210> SEQ ID NO 88
<211> LENGTH: 250
<212> TYPE: PRT
<213> ORGANISM: Artificial sequence
<220> FEATURE:
```

<223> OTHER INFORMATION: bouganin

<400> SEQUENCE: 88

```
Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
                100                 105                 110

Ser Tyr Gln Lys Leu Val Asn Ala Ala Lys Ala Asp Arg Lys Ala Leu
            115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250
```